(12) United States Patent  
Steinhagen et al.

(10) Patent No.: US 11,828,758 B2  
(45) Date of Patent: Nov. 28, 2023

(54) IMMUNOASSAY FOR THE DIAGNOSIS OF VIRAL INFECTIONS

(71) Applicant: EUROIMMUN Medizinische Labordiagnostika AG, Lübeck (DE)

(72) Inventors: Katja Steinhagen, Gross Groenau (DE); Andrea Deerberg, Gross Groenau (DE); Erik Lattwein, Luebeck (DE); Christiane Radzimski, Reinfeld (DE); Jana Böthfür, Schlagsdorf (DE)

(73) Assignee: EUROIMMUN Medizinische Labordiagnostika AG, Lübeck (DE)

( * ) Notice: Subject to any disclaimer, the term of this patent is extended or adjusted under 35 U.S.C. 154(b) by 401 days.

(21) Appl. No.: 16/948,825

(22) Filed: Oct. 1, 2020

(65) Prior Publication Data

US 2021/0033609 A1     Feb. 4, 2021

Related U.S. Application Data

(62) Division of application No. 16/077,757, filed as application No. PCT/EP2017/000249 on Feb. 22, 2017, now Pat. No. 10,837,963.

(30) Foreign Application Priority Data

Feb. 22, 2016 (EP) .................................. 16000422  
Feb. 24, 2016 (EP) .................................. 16000442

(Continued)

(51) Int. Cl.  
*G01N 33/569*     (2006.01)  
*C07K 14/005*     (2006.01)  
*A61K 39/00*       (2006.01)

(52) U.S. Cl.  
CPC ..... *G01N 33/56983* (2013.01); *C07K 14/005* (2013.01); *A61K 39/00* (2013.01);  
(Continued)

(58) Field of Classification Search  
None  
See application file for complete search history.

(56) References Cited

U.S. PATENT DOCUMENTS 6,870,032 B1    3/2005  Flamand et al.  
2015/0301035 A1  10/2015  Meyer et al.

FOREIGN PATENT DOCUMENTS

EP   2 980 099    2/2016  
WO   1988/03032   5/1988  
(Continued)

OTHER PUBLICATIONS

Shu PY, Chen LK, Chang SF, Yueh YY, Chow L, Chien LJ, Chin C, Lin TH, Huang JH. Dengue NS1-specific antibody responses: isotype distribution and serotyping in patients with Dengue fever and Dengue hemorrhagic fever. J Med Virol. Oct. 2000;62(2):224-32. (Year: 2000).*

(Continued)

*Primary Examiner* — Michelle S Horning  
(74) *Attorney, Agent, or Firm* — Grüneberg and Myers, PLLC

(57) ABSTRACT

A recombinant polypeptide can be used in the diagnosis of the presence of a Zika virus in a patient. The recombinant polypeptide includes SEQ ID NO: 1 or a variant thereof. The recombinant peptide may be a monomer, a dimer, or a hexamer.

10 Claims, 18 Drawing Sheets

Specification includes a Sequence Listing.

(30) Foreign Application Priority Data

Feb. 25, 2016 (EP) .................................. 16000454
Mar. 31, 2016 (EP) .................................. 16000747

(52) U.S. Cl.
CPC ............ *C12N 2770/24122* (2013.01); *C12N 2770/24134* (2013.01); *G01N 2333/185* (2013.01); *G01N 2469/20* (2013.01); *G01N 2800/26* (2013.01)

(56) References Cited

FOREIGN PATENT DOCUMENTS

| WO | 2007/133167 | 11/2007 |
|---|---|---|
| WO | 2013/041540 | 3/2013 |
| WO | 2015/095735 | 6/2015 |
| WO | 2016/022071 | 2/2016 |
| WO | 2017/009873 | 1/2017 |

OTHER PUBLICATIONS

Hornbeck P, Fleisher TA, Papadopoulos NM. Isotype determination of antibodies. Curr Protoc Immunol. May 2001;Chapter 2:Unit 2.2. doi: 10.1002/0471142735.im0202s01. PMID: 18432767. (Year: 2001).*
Written Opinion dated Jan. 20, 2020 in Singaporean Application 11201805496P, 6 pages.
Office Action dated Apr. 20, 2020 in European Application No. 17 707 171.9.
GenBank: ABI54475.1: polyprotein [Zika virus] (Year: 2009).
Akey et al., "Flavivirus NS1 crystal structures reveal a surface for membrane association and regions of interaction with the immune system," Science. Feb. 21, 2014; 343(6173): 881-885.doi:10.1126/science.1247749., pp. 1-10.
Anonymous, UniProtKB—C8XPB1 (C8XPB1_ZIKV) UniProt, Genome Polyprotein—Zike virus (strain Mr 766) (ZIKV), IBNSDOCID: <XP_55276732A_I_>t/C8XPB1, pp. 1-12.
Charrel et al. "State of knowledge on Zika virus for an adequate laboratory response," Bull World Health Organ, 2016, pp. 1-29, XP055276698 retrieved from https://www.researchgate.net/profile/Chantal_Reusken/publication/293950559_State_of_knowledge_on_Zika_ virus_for_an_adequate_laboratory_response/links/5ae78cb0aca2725dabb33f06/ State-of- knowledge-on-Zika-virus- for-an-adequate-laboratory-response.pdf on Jun. 22, 2018.
Euroimmun Medizinische Labordiagnostika AG, "Anti-Zika Virus ELISA (IgM) Test Instruction," EI 2668-9601 M a Uk C01.doc, Version Sep. 2, 2016 (8 pages).
Huzly, et al., "High specificity of a novel Zika virus ELISA in European patients after exposure to different flaviviruses" Euro Surveill. 2016;21(16):pii=30203. DOI: http://dx.doi.org/10.2807/1560-7917.ES.2016.21.16.30203. pp. 1-4.
Raoult, et al., "The line blot: an immunoassay for monoclonal and other antibodies—Its application to the serotyping of Gram-negative bacteria", Journal of Immunological Methods, 125 (1989), pp. 57-65.
Steinhagen, et al., "Serodiagnosis of Zika virus (ZIKV) infections by a novel NS1-based ELISA devoid of cross-reactivity with dengue virus antibodies: a multicohort study of assay performance, 2015 to 2016," Euro Surveill. 2016;21(50):pii=30426. DOI: http://dx.doi.org/10.2807/1560-7917.ES.2016.21.50.30426, pp. 1-16.
Xu, et al.,"Contribution of intertwined loop to membrane association revealed by Zika virus full-length NS1 structure", The EMBO Journal, vol. 35, No. 20, 2016. pp. 2170-2178.
Allgemeine Virologie, edited by Tobler, et al., "Zellabwehr und Wirtsabwehr" Haupt, Chapter 9, 2016, pp. 207, 227-229, with partial translation.
Clinical and Diagnostic Virology, edited by Kudessia and Wreghitt, "Arboviruses and haemorrhagic fever viruses", Cambridge University Press, Chapter 2, 2009, 6 pages.
Clinical and Diagnostic Virology, edited by Kudesia and Wreghitt, "Serological techniques", Cambridge University Press, Chapter 47, 2009, pp. 204-210.
Lyler R. Petersersen et al., Clinical Virology, edited by Douglas D. Richman et al., "Arthropod-borne Flaviviruses", ASM Press, Chapter 53, 2016, pp. 1267, 1291-1311.
Clinical Virology Manual, edited by Richard L. Hodinka, et al., "Arboviruses" ASM Press, Chapter 35, 2016, pp. 493-514.
Lexikon der Medizinischen Labordiagnostik, edited by Gressner and Arndt, "Viren", Springer, 2013, pp. 1387, with English translation.
Modrow et al., Molekulare Virologie, 3. Auflage, "B-Lymphocyten und Antikörper", Spektrum, Chapter 7.2.2, 2010, pp. 68-71, with English translation.
Public Health Ontario, "Labstract, Dec. 2008", Dec. 2008, pp. 1-3, https://www.publichealthontario.ca/-/media/documents/lab/lab-sd-044-interpretation-viral-igm-igg-serology.pdf?la=en.
Virology, edited by Korsman, et al., "The laboratory diagnosis of viral infections—introduction and principles", Elsevier, 2017, pp. 26-29.
Sequence alignment DENV vs ZIKV NS1, "Dengue (DENV) Type 2 NS1 (*NS1—Nonstructural protein 1—Dengue virus type 2* | *UniProtKB* | *UniProt*) vs SEQ ID No. 1 of U.S. Appl. No. 16/948,825", 2023, 3 pages.

* cited by examiner

Figure 1

Anti-Zika Virus IgM and IgG

| ZIKV patients (n=29) | | Anti-ZIKV IgM | | |
|---|---|---|---|---|
| | | Positive | Borderline | Negative |
| Anti-ZIKV IgG | Positive | 16 | 2 | 2 |
| | Borderline | 2 | 0 | 0 |
| | Negative | 6 | 0 | 1 |

| | Anti-ZIKV ELISA reactivity | | |
|---|---|---|---|
| | IgM | IgG | IgM / IgG |
| n (positive/total) | 24/29 | 20/29 | 28/29 |
| Sensitivity | 82.2% | 69.0% | 96.6% |
| 95% CI | 65.0-92.9% | 50.6-82.9% | 84.1-100% |

Time course analysis

Fig. 9D

SEQUENCE LISTING

```
<160> NUMBER OF SEQ ID NOS: 27

<210> SEQ ID NO 1
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide; Zika virus NS1 antigen
```

<400> SEQUENCE: 1

```
Asp Val Gly Cys Ser Val Asp Phe Ser Lys Lys Glu Thr Arg Cys Gly
1               5                   10                  15

Thr Gly Val Phe Val Tyr Asn Asp Val Glu Ala Trp Arg Asp Arg Tyr
            20                  25                  30

Lys Tyr His Pro Asp Ser Pro Arg Arg Leu Ala Ala Ala Val Lys Gln
        35                  40                  45

Ala Trp Glu Glu Gly Ile Cys Gly Ile Ser Ser Val Ser Arg Met Glu
50                  55                  60

Asn Ile Met Trp Lys Ser Val Glu Gly Glu Leu Asn Ala Ile Leu Glu
65                  70                  75                  80

Glu Asn Gly Val Gln Leu Thr Val Val Gly Ser Val Lys Asn Pro
                85                  90                  95

Met Trp Arg Gly Pro Gln Arg Leu Pro Val Pro Val Asn Glu Leu Pro
            100                 105                 110

His Gly Trp Lys Ala Trp Gly Lys Ser Tyr Phe Val Arg Ala Ala Lys
        115                 120                 125

Thr Asn Asn Ser Phe Val Val Asp Gly Asp Thr Leu Lys Glu Cys Pro
130                 135                 140

Leu Lys His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
                165                 170                 175

Leu Glu Cys Asp Pro Ala Val Ile Gly Thr Ala Val Lys Gly Lys Glu
            180                 185                 190

Ala Ala His Ser Asp Leu Gly Tyr Trp Ile Glu Ser Glu Lys Asn Asp
        195                 200                 205

Thr Trp Arg Leu Lys Arg Ala His Leu Ile Glu Met Lys Thr Cys Glu
210                 215                 220

Trp Pro Lys Ser His Thr Leu Trp Thr Asp Gly Val Glu Glu Ser Asp
225                 230                 235                 240

Leu Ile Ile Pro Lys Ser Leu Ala Gly Pro Leu Ser His His Asn Thr
                245                 250                 255

Arg Glu Gly Tyr Arg Thr Gln Val Lys Gly Pro Trp His Ser Glu Glu
            260                 265                 270

Leu Glu Ile Arg Phe Glu Glu Cys Pro Gly Thr Lys Val His Val Glu
        275                 280                 285

Glu Thr Cys Gly Thr Arg Gly Pro Ser Leu Arg Ser Thr Thr Ala Ser
290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Met Val Thr Ala
            340                 345                 350
```

<210> SEQ ID NO 2
<211> LENGTH: 352
<212> TYPE: PRT
<213> ORGANISM: Artificial Sequence
<220> FEATURE:
<223> OTHER INFORMATION: Description of Artificial Sequence: Synthetic polypeptide; Dengue virus 1 NS1 antigen

<400> SEQUENCE: 2

Asp Ser Gly Cys Val Ile Asn Trp Lys Gly Arg Glu Leu Lys Cys Gly
1               5                   10                  15

Ser Gly Ile Phe Val Thr Asn Glu Val His Thr Trp Thr Glu Gln Tyr
            20                  25                  30

Lys Phe Gln Ala Asp Ser Pro Lys Arg Leu Ser Ala Ala Ile Gly Lys
        35                  40                  45

Ala Trp Glu Glu Gly Val Cys Gly Ile Arg Ser Ala Thr Arg Leu Glu
50                  55                  60

Asn Ile Met Trp Lys Gln Ile Ser Asn Glu Leu Asn His Ile Leu Leu
65                  70                  75                  80

Glu Asn Asp Met Lys Phe Thr Val Val Gly Asp Ala Ser Gly Ile
                85                  90                  95

Leu Ala Gln Gly Lys Lys Met Ile Arg Pro Gln Pro Met Glu His Lys
            100                 105                 110

Tyr Ser Trp Lys Ser Trp Gly Lys Ala Lys Ile Ile Gly Ala Asp Ile
        115                 120                 125

Gln Asn Thr Thr Phe Ile Ile Asp Gly Pro Asp Thr Pro Glu Cys Ser
130                 135                 140

Asp Asp Gln Arg Ala Trp Asn Ile Trp Glu Val Glu Asp Tyr Gly Phe
145                 150                 155                 160

Gly Ile Phe Thr Thr Asn Ile Trp Leu Lys Leu Arg Asp Ser Tyr Thr
                165                 170                 175

Gln Met Cys Asp His Arg Leu Met Ser Ala Ala Ile Lys Asp Ser Lys
            180                 185                 190

Ala Val His Ala Asp Met Gly Tyr Trp Ile Glu Ser Glu Lys Asn Glu
        195                 200                 205

Thr Trp Lys Leu Ala Arg Ala Ser Phe Ile Glu Val Lys Thr Cys Ile
210                 215                 220

Trp Pro Lys Ser His Thr Leu Trp Ser Asn Gly Val Leu Glu Ser Glu
225                 230                 235                 240

Met Ile Ile Pro Lys Ile Tyr Gly Gly Pro Ile Ser Gln His Asn Tyr
                245                 250                 255

Arg Pro Gly Tyr Phe Thr Gln Thr Ala Gly Pro Trp His Leu Gly Lys
            260                 265                 270

Leu Glu Leu Asp Phe Asp Leu Cys Glu Gly Thr Thr Val Ile Val Asp
        275                 280                 285

Glu His Cys Gly Asn Arg Gly Pro Ser Leu Arg Thr Thr Thr Val Thr
290                 295                 300

Gly Lys Ile Ile His Glu Trp Cys Cys Arg Ser Cys Thr Leu Pro Pro
305                 310                 315                 320

Leu Arg Phe Arg Gly Glu Asp Gly Cys Trp Tyr Gly Met Glu Ile Arg
                325                 330                 335

Pro Val Lys Glu Lys Glu Glu Asn Leu Val Lys Ser Met Val Ser Ala
            340                 345                 350

<210> SEQ ID NO 3
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide; Dengue virus 2 NS1 antigen

<400> SEQUENCE: 3

Asp Ser Gly Cys Val Val Ser Trp Lys Asn Lys Glu Leu Lys Cys Gly

```
1               5                   10                  15
Ser Gly Ile Phe Ile Thr Asp Asn Val His Thr Trp Thr Glu Gln Tyr
            20                  25                  30
Lys Phe Gln Pro Glu Ser Pro Ser Lys Leu Ala Ser Ala Ile Gln Lys
            35                  40                  45
Ala Gln Glu Glu Gly Ile Cys Gly Ile Arg Ser Val Thr Arg Leu Glu
            50                  55                  60
Asn Leu Met Trp Lys Gln Ile Thr Pro Glu Leu Asn His Ile Leu Ala
65                  70                  75                  80
Glu Asn Glu Val Lys Leu Thr Ile Met Thr Gly Asp Ile Lys Gly Ile
                85                  90                  95
Met Gln Ala Gly Lys Arg Ser Leu Arg Pro Gln Pro Thr Glu Leu Lys
            100                 105                 110
Tyr Ser Trp Lys Thr Trp Gly Lys Ala Lys Met Leu Ser Thr Glu Ser
            115                 120                 125
His Asn Gln Thr Phe Leu Ile Asp Gly Pro Glu Thr Ala Glu Cys Pro
            130                 135                 140
Asn Thr Asn Arg Ala Trp Asn Ser Leu Glu Val Glu Asp Tyr Gly Phe
145                 150                 155                 160
Gly Val Phe Thr Thr Asn Ile Trp Leu Lys Leu Lys Glu Lys Gln Asp
                165                 170                 175
Ala Phe Cys Asp Ser Lys Leu Met Ser Ala Ala Ile Lys Asp Asn Arg
            180                 185                 190
Ala Val His Ala Asp Met Gly Tyr Trp Ile Glu Ser Ala Leu Asn Asp
            195                 200                 205
Thr Trp Lys Ile Glu Lys Ala Ser Phe Ile Glu Val Lys Asn Cys His
            210                 215                 220
Trp Pro Lys Ser His Thr Leu Trp Ser Asn Gly Val Leu Glu Ser Glu
225                 230                 235                 240
Met Ile Ile Pro Lys Asn Leu Ala Gly Pro Val Ser Gln His Asn Tyr
                245                 250                 255
Arg Pro Gly Tyr His Thr Gln Ile Ala Gly Pro Trp His Leu Gly Lys
            260                 265                 270
Leu Glu Met Asp Phe Asp Phe Cys Asp Gly Thr Thr Val Val Val Thr
            275                 280                 285
Glu Asp Cys Gly Asn Arg Gly Pro Ser Leu Arg Thr Thr Thr Ala Ser
            290                 295                 300
Gly Lys Leu Ile Thr Glu Trp Cys Cys Arg Ser Cys Thr Leu Pro Pro
305                 310                 315                 320
Leu Arg Tyr Arg Gly Glu Asp Gly Cys Trp Tyr Gly Met Glu Ile Arg
                325                 330                 335
Pro Leu Lys Glu Lys Glu Glu Asn Leu Val Asn Ser Leu Val Thr Ala
            340                 345                 350
```

<210> SEQ ID NO 4
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide; Dengue virus 3 NS1 antigen

<400> SEQUENCE: 4

```
Asp Met Gly Cys Val Ile Asn Trp Lys Gly Lys Glu Leu Lys Cys Gly
1               5                   10                  15
```

Ser Gly Ile Phe Val Thr Asn Glu Val His Thr Trp Thr Glu Gln Tyr
            20                  25                  30

Lys Phe Gln Ala Asp Ser Pro Lys Arg Leu Ala Thr Ala Ile Ala Gly
        35                  40                  45

Ala Trp Glu Asn Gly Val Cys Gly Ile Arg Ser Thr Thr Arg Met Glu
    50                  55                  60

Asn Leu Leu Trp Lys Gln Ile Ala Asn Glu Leu Asn His Ile Leu Trp
65                  70                  75                  80

Glu Asn Asn Ile Lys Leu Thr Val Val Gly Asp Ile Ile Gly Val
                85                  90                  95

Leu Glu Gln Gly Lys Arg Thr Leu Thr Pro Gln Pro Met Glu Leu Lys
                100                 105                 110

Tyr Ser Trp Lys Ile Trp Gly Lys Ala Lys Ile Val Thr Ala Glu Thr
            115                 120                 125

Gln Asn Ser Ser Phe Ile Ile Asp Gly Pro Asn Thr Pro Glu Cys Pro
        130                 135                 140

Ser Ala Ser Arg Ala Trp Asn Val Trp Glu Val Glu Asp Tyr Gly Phe
145                 150                 155                 160

Gly Val Phe Thr Thr Asn Ile Trp Leu Lys Leu Arg Glu Val Tyr Thr
                165                 170                 175

Gln Ser Cys Asp His Arg Leu Met Ser Ala Ala Ile Lys Asp Glu Arg
            180                 185                 190

Ala Val His Ala Asp Met Gly Tyr Trp Ile Glu Ser Gln Lys Asn Gly
        195                 200                 205

Ser Trp Lys Leu Glu Lys Ala Ser Leu Ile Glu Val Lys Thr Cys Thr
210                 215                 220

Trp Pro Lys Ser His Thr Leu Trp Ser Asn Gly Val Leu Glu Ser Asp
225                 230                 235                 240

Met Ile Ile Pro Lys Ser Leu Ala Gly Pro Ile Ser Gln His Asn His
                245                 250                 255

Arg Pro Gly Tyr His Thr Gln Thr Ala Gly Pro Trp His Leu Gly Lys
            260                 265                 270

Leu Glu Leu Asp Phe Asn Tyr Cys Glu Gly Thr Thr Val Val Ile Thr
        275                 280                 285

Glu Asn Cys Gly Thr Arg Gly Pro Ser Leu Arg Thr Thr Thr Val Ser
    290                 295                 300

Gly Lys Leu Ile His Glu Trp Cys Cys Arg Ser Cys Thr Leu Pro Pro
305                 310                 315                 320

Leu Arg Tyr Met Gly Glu Asp Gly Cys Trp Tyr Gly Met Glu Ile Arg
                325                 330                 335

Pro Ile Asn Glu Lys Glu Glu Asn Met Val Lys Ser Leu Ala Ser Ala
            340                 345                 350

<210> SEQ ID NO 5
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide; Dengue virus 4 NS1 antigen

<400> SEQUENCE: 5

Asp Thr Gly Cys Ala Val Ser Trp Ser Gly Lys Glu Leu Lys Cys Gly
1               5                   10                  15

Ser Gly Ile Phe Val Val Asp Asn Val His Thr Trp Thr Glu Gln Tyr
            20                  25                  30

```
Lys Phe Gln Pro Glu Ser Pro Ala Arg Leu Ala Ser Ala Ile Leu Asn
            35                  40                  45

Ala His Lys Asp Gly Val Cys Gly Ile Arg Ser Thr Thr Arg Leu Glu
 50                  55                  60

Asn Val Met Trp Lys Gln Ile Thr Asn Glu Leu Asn Tyr Val Leu Trp
 65                  70                  75                  80

Glu Gly Gly His Asp Leu Thr Val Val Ala Gly Asp Val Lys Gly Val
                 85                  90                  95

Leu Thr Lys Gly Lys Arg Ala Leu Thr Pro Pro Val Asn Asp Leu Lys
            100                 105                 110

Tyr Ser Trp Lys Thr Trp Gly Lys Ala Lys Ile Phe Thr Pro Glu Ala
            115                 120                 125

Arg Asn Ser Thr Phe Leu Ile Asp Gly Pro Asp Thr Ser Glu Cys Pro
130                 135                 140

Asn Glu Arg Arg Ala Trp Asn Ser Leu Glu Val Glu Asp Tyr Gly Phe
145                 150                 155                 160

Gly Met Phe Thr Thr Asn Ile Trp Met Lys Phe Arg Glu Gly Ser Ser
                165                 170                 175

Glu Val Cys Asp His Arg Leu Met Ser Ala Ala Ile Lys Asp Gln Lys
            180                 185                 190

Ala Val His Ala Asp Met Gly Tyr Trp Ile Glu Ser Ser Lys Asn Gln
            195                 200                 205

Thr Trp Gln Ile Glu Lys Ala Ser Leu Ile Glu Val Lys Thr Cys Leu
            210                 215                 220

Trp Pro Lys Thr His Thr Leu Trp Ser Asn Gly Val Leu Glu Ser Gln
225                 230                 235                 240

Met Leu Ile Pro Lys Ser Tyr Ala Gly Pro Phe Ser Gln His Asn Tyr
                245                 250                 255

Arg Gln Gly Tyr Ala Thr Gln Thr Val Gly Pro Trp His Leu Gly Lys
            260                 265                 270

Leu Glu Ile Asp Phe Gly Glu Cys Pro Gly Thr Thr Val Thr Ile Gln
            275                 280                 285

Glu Asp Cys Asp His Arg Gly Pro Ser Leu Arg Thr Thr Thr Ala Ser
290                 295                 300

Gly Lys Leu Val Thr Gln Trp Cys Cys Arg Ser Cys Thr Met Pro Pro
305                 310                 315                 320

Leu Arg Phe Leu Gly Glu Asp Gly Cys Trp Tyr Gly Met Glu Ile Arg
                325                 330                 335

Pro Leu Ser Glu Lys Glu Glu Asn Met Val Lys Ser Gln Val Ser Ala
            340                 345                 350

<210> SEQ ID NO 6
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide; West Nile virus NS1 antigen

<400> SEQUENCE: 6

Asp Thr Gly Cys Ala Ile Asp Ile Gly Arg Gln Glu Leu Arg Cys Gly
1               5                   10                  15

Ser Gly Val Phe Ile His Asn Asp Val Glu Ala Trp Met Asp Arg Tyr
            20                  25                  30

Lys Phe Tyr Pro Glu Thr Pro Gln Gly Leu Ala Lys Ile Ile Gln Lys
```

```
                  35                  40                  45

Ala His Ala Glu Gly Val Cys Gly Leu Arg Ser Val Ser Arg Leu Glu
     50                  55                  60

His Gln Met Trp Glu Ala Ile Lys Asp Glu Leu Asn Thr Leu Leu Lys
 65                  70                  75                  80

Glu Asn Gly Val Asp Leu Ser Val Val Glu Lys Gln Asn Gly Met
                 85                  90                  95

Tyr Lys Ala Ala Pro Lys Arg Leu Ala Ala Thr Thr Glu Lys Leu Glu
             100                 105                 110

Met Gly Trp Lys Ala Trp Gly Lys Ser Ile Ile Phe Ala Pro Glu Leu
         115                 120                 125

Ala Asn Asn Thr Phe Val Ile Asp Gly Pro Glu Thr Glu Glu Cys Pro
     130                 135                 140

Thr Ala Asn Arg Ala Trp Asn Ser Met Glu Val Glu Asp Phe Gly Phe
145                 150                 155                 160

Gly Leu Thr Ser Thr Arg Met Phe Leu Arg Ile Arg Glu Thr Asn Thr
                 165                 170                 175

Thr Glu Cys Asp Ser Lys Ile Ile Gly Thr Ala Val Lys Asn Asn Met
             180                 185                 190

Ala Val His Ser Asp Leu Ser Tyr Trp Ile Glu Ser Gly Leu Asn Asp
         195                 200                 205

Thr Trp Lys Leu Glu Arg Ala Val Leu Gly Val Lys Ser Cys Thr
     210                 215                 220

Trp Pro Glu Thr His Thr Leu Trp Gly Asp Gly Val Leu Glu Ser Asp
225                 230                 235                 240

Leu Ile Ile Pro Ile Thr Leu Ala Gly Pro Arg Ser Asn His Asn Arg
                 245                 250                 255

Arg Pro Gly Tyr Lys Thr Gln Asn Gln Gly Pro Trp Asp Glu Gly Arg
             260                 265                 270

Val Glu Ile Asp Phe Asp Tyr Cys Pro Gly Thr Thr Val Thr Ile Ser
         275                 280                 285

Asp Ser Cys Glu His Arg Gly Pro Ala Ala Arg Thr Thr Thr Glu Ser
     290                 295                 300

Gly Lys Leu Ile Thr Asp Trp Cys Cys Arg Ser Cys Thr Leu Pro Pro
305                 310                 315                 320

Leu Arg Phe Gln Thr Glu Asn Gly Cys Trp Tyr Gly Met Glu Ile Arg
                 325                 330                 335

Pro Thr Arg His Asp Glu Lys Thr Leu Val Gln Ser Arg Val Asn Ala
             340                 345                 350

<210> SEQ ID NO 7
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide; Tick-borne encephalitis virus NS1 antigen

<400> SEQUENCE: 7

Asp Val Gly Cys Ala Val Asp Thr Glu Arg Met Glu Leu Arg Cys Gly
1               5                  10                  15

Glu Gly Leu Val Val Trp Arg Glu Val Ser Glu Trp Tyr Asp Asn Tyr
             20                  25                  30

Ala Tyr Tyr Pro Glu Thr Pro Gly Ala Leu Ala Ser Ala Ile Lys Glu
         35                  40                  45
```

-continued

```
Thr Phe Glu Glu Gly Thr Cys Gly Ile Val Pro Gln Asn Arg Leu Glu
 50                  55                  60

Met Ala Met Trp Arg Ser Ser Ala Thr Glu Leu Asn Leu Ala Leu Ala
 65                  70                  75                  80

Glu Gly Asp Ala Asn Leu Thr Val Val Asp Lys Leu Asp Pro Thr
                 85                  90                  95

Asp Tyr Arg Gly Gly Ile Pro Gly Leu Leu Lys Lys Gly Lys Asp Ile
            100                 105                 110

Lys Val Ser Trp Lys Ser Trp Gly His Ser Met Ile Trp Ser Ile Pro
            115                 120                 125

Glu Ala Pro Arg Arg Phe Met Val Gly Thr Glu Gly Ser Ser Glu Cys
130                 135                 140

Pro Leu Glu Arg Arg Lys Thr Gly Val Phe Thr Val Ala Glu Phe Gly
145                 150                 155                 160

Val Gly Leu Arg Thr Lys Val Phe Leu Asp Phe Arg Gln Glu Ser Thr
                165                 170                 175

His Glu Cys Asp Thr Gly Val Met Gly Ala Ala Val Lys Asn Gly Met
            180                 185                 190

Ala Val His Thr Asp Gln Ser Leu Trp Met Lys Ser Val Arg Asn Asp
            195                 200                 205

Thr Gly Thr Tyr Ile Val Glu Leu Leu Val Thr Asp Leu Arg Asn Cys
            210                 215                 220

Ser Trp Pro Ala Ser His Thr Ile Asp Asn Ala Glu Val Val Asp Ser
225                 230                 235                 240

Glu Leu Phe Leu Pro Ala Ser Leu Ala Gly Pro Arg Ser Trp Tyr Asn
                245                 250                 255

Arg Ile Pro Gly Tyr Ser Glu Gln Val Lys Gly Pro Trp Lys Tyr Ser
            260                 265                 270

Pro Ile Arg Val Thr Arg Glu Glu Cys Pro Gly Thr Arg Val Thr Ile
            275                 280                 285

Asn Ala Asp Cys Asp Lys Arg Gly Ala Ser Val Arg Ser Thr Thr Glu
290                 295                 300

Ser Gly Lys Val Ile Pro Glu Trp Cys Cys Arg Thr Cys Thr Leu Pro
305                 310                 315                 320

Pro Val Thr Phe Arg Thr Gly Thr Asp Cys Trp Tyr Ala Met Glu Ile
                325                 330                 335

Arg Pro Val His Asp Gln Gly Gly Leu Val Arg Ser Met Val Val Ala
            340                 345                 350
```

<210> SEQ ID NO 8
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide; Japanese encephalitis virus NS1 antigen

<400> SEQUENCE: 8

```
Asp Thr Gly Cys Ala Ile Asp Ile Thr Arg Lys Glu Met Arg Cys Gly
 1               5                  10                  15

Ser Gly Ile Phe Val His Asn Asp Val Glu Ala Trp Val Asp Arg Tyr
                 20                  25                  30

Lys Tyr Leu Pro Glu Thr Pro Arg Ser Leu Ala Lys Ile Val His Lys
            35                  40                  45

Ala His Gln Glu Gly Val Cys Gly Val Arg Ser Val Thr Arg Leu Glu
 50                  55                  60
```

His Gln Met Trp Glu Ser Val Arg Asp Glu Leu Asn Val Leu Leu Lys
65                  70                  75                  80

Glu Asn Ala Val Asp Leu Ser Val Val Asn Lys Pro Val Gly Arg
            85                  90                  95

Tyr Arg Ser Ala Pro Lys Arg Leu Ser Met Thr Gln Glu Lys Phe Glu
            100                 105                 110

Met Gly Trp Lys Ala Trp Gly Lys Ser Ile Leu Phe Ala Pro Glu Leu
            115                 120                 125

Ala Asn Ser Thr Phe Val Val Asp Gly Pro Glu Thr Lys Glu Cys Pro
130                 135                 140

Asp Glu Arg Arg Ala Trp Asn Ser Met Gln Ile Glu Asp Phe Gly Phe
145                 150                 155                 160

Gly Ile Thr Ser Thr Arg Val Trp Leu Lys Ile Arg Glu Glu Asn Thr
                165                 170                 175

Asp Glu Cys Asp Gly Ala Ile Ile Gly Thr Ala Val Lys Gly His Val
            180                 185                 190

Ala Val His Ser Asp Leu Ser Tyr Trp Ile Glu Ser Arg Leu Asn Asp
            195                 200                 205

Thr Trp Lys Leu Glu Arg Ala Val Phe Gly Glu Val Lys Ser Cys Thr
210                 215                 220

Trp Pro Glu Thr His Thr Leu Trp Gly Asp Gly Val Glu Glu Ser Glu
225                 230                 235                 240

Leu Ile Ile Pro His Thr Ile Ala Gly Pro Arg Ser Lys His Asn Arg
                245                 250                 255

Arg Glu Gly Tyr Lys Thr Gln Asn Gln Gly Pro Trp Asp Glu Asn Gly
            260                 265                 270

Ile Val Leu Asp Phe Asp Tyr Cys Pro Gly Thr Lys Val Thr Ile Thr
            275                 280                 285

Glu Asp Cys Gly Lys Arg Gly Pro Ser Ile Arg Thr Thr Thr Asp Ser
290                 295                 300

Gly Lys Leu Ile Thr Asp Trp Cys Cys Arg Ser Cys Ser Leu Pro Pro
305                 310                 315                 320

Leu Arg Phe Arg Thr Glu Asn Gly Cys Trp Tyr Gly Met Glu Ile Arg
                325                 330                 335

Pro Val Arg His Asp Glu Thr Thr Leu Val Arg Ser Gln Val Asp Ala
            340                 345                 350

<210> SEQ ID NO 9
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide; Yellow fever virus NS1 antigen

<400> SEQUENCE: 9

Asp Gln Gly Cys Ala Ile Asn Phe Gly Lys Arg Glu Leu Lys Cys Gly
1               5                   10                  15

Asp Gly Ile Phe Ile Phe Arg Asp Ser Asp Asp Trp Leu Asn Lys Tyr
            20                  25                  30

Ser Tyr Tyr Pro Glu Asp Pro Val Lys Leu Ala Ser Ile Val Lys Ala
            35                  40                  45

Ser Phe Glu Glu Gly Lys Cys Gly Leu Asn Ser Val Asp Ser Leu Glu
50                  55                  60

His Glu Met Trp Arg Ser Arg Ala Asp Glu Ile Asn Ala Ile Leu Glu

```
                65                  70                  75                  80
        Glu Asn Glu Val Asp Ile Ser Val Val Gln Asp Pro Lys Asn Val
                            85                  90                  95
        Tyr Gln Arg Gly Thr His Pro Phe Ser Arg Ile Arg Asp Gly Leu Gln
                        100                 105                 110
        Tyr Gly Trp Lys Thr Trp Gly Lys Asn Leu Val Phe Ser Pro Gly Arg
                    115                 120                 125
        Lys Asn Gly Ser Phe Ile Ile Asp Gly Lys Ser Arg Lys Glu Cys Pro
                130                 135                 140
        Phe Ser Asn Arg Val Trp Asn Ser Phe Gln Ile Glu Glu Phe Gly Thr
        145                 150                 155                 160
        Gly Val Phe Thr Thr Arg Val Tyr Met Asp Ala Val Phe Glu Tyr Thr
                            165                 170                 175
        Ile Asp Cys Asp Gly Ser Ile Leu Gly Ala Ala Val Asn Gly Lys Lys
                        180                 185                 190
        Ser Ala His Gly Ser Pro Thr Phe Trp Met Gly Ser His Glu Val Asn
                    195                 200                 205
        Gly Thr Trp Met Ile His Thr Leu Glu Ala Leu Asp Tyr Lys Glu Cys
                210                 215                 220
        Glu Trp Pro Pro Thr His Thr Ile Gly Thr Ser Val Glu Glu Ser Glu
        225                 230                 235                 240
        Met Phe Met Pro Arg Ser Ile Gly Gly Pro Val Ser His Asn His
                            245                 250                 255
        Ile Pro Gly Tyr Lys Val Gln Thr Asn Gly Pro Trp Met Gln Val Pro
                        260                 265                 270
        Leu Glu Val Lys Arg Glu Ala Cys Pro Gly Thr Ser Val Ile Ile Asp
                    275                 280                 285
        Gly Asn Cys Asp Gly Arg Gly Lys Ser Thr Arg Ser Thr Thr Asp Ser
                290                 295                 300
        Gly Lys Ile Ile Pro Glu Trp Cys Cys Arg Ser Cys Thr Met Pro Pro
        305                 310                 315                 320
        Val Ser Phe His Gly Ser Asp Gly Cys Trp Tyr Pro Met Glu Ile Arg
                            325                 330                 335
        Pro Arg Lys Thr His Glu Ser His Leu Val Arg Ser Trp Val Thr Ala
                        340                 345                 350

<210> SEQ ID NO 10
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide; Zika virus NS1 antigen with C-terminal His tag

<400> SEQUENCE: 10

Asp Val Gly Cys Ser Val Asp Phe Ser Lys Lys Glu Thr Arg Cys Gly
        1               5                   10                  15
        Thr Gly Val Phe Val Tyr Asn Asp Val Glu Ala Trp Arg Asp Arg Tyr
                            20                  25                  30
        Lys Tyr His Pro Asp Ser Pro Arg Arg Leu Ala Ala Ala Val Lys Gln
                        35                  40                  45
        Ala Trp Glu Glu Gly Ile Cys Gly Ile Ser Ser Val Ser Arg Met Glu
                    50                  55                  60
        Asn Ile Met Trp Lys Ser Val Glu Gly Glu Leu Asn Ala Ile Leu Glu
        65                  70                  75                  80
```

```
Glu Asn Gly Val Gln Leu Thr Val Val Val Gly Ser Val Lys Asn Pro
                85                  90                  95

Met Trp Arg Gly Pro Gln Arg Leu Pro Val Pro Val Asn Glu Leu Pro
            100                 105                 110

His Gly Trp Lys Ala Trp Gly Lys Ser Tyr Phe Val Arg Ala Ala Lys
            115                 120                 125

Thr Asn Asn Ser Phe Val Val Asp Gly Asp Thr Leu Lys Glu Cys Pro
            130                 135                 140

Leu Lys His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
                165                 170                 175

Leu Glu Cys Asp Pro Ala Val Ile Gly Thr Ala Val Lys Gly Lys Glu
            180                 185                 190

Ala Ala His Ser Asp Leu Gly Tyr Trp Ile Glu Ser Glu Lys Asn Asp
            195                 200                 205

Thr Trp Arg Leu Lys Arg Ala His Leu Ile Glu Met Lys Thr Cys Glu
            210                 215                 220

Trp Pro Lys Ser His Thr Leu Trp Thr Asp Gly Val Glu Glu Ser Asp
225                 230                 235                 240

Leu Ile Ile Pro Lys Ser Leu Ala Gly Pro Leu Ser His His Asn Thr
                245                 250                 255

Arg Glu Gly Tyr Arg Thr Gln Val Lys Gly Pro Trp His Ser Glu Glu
            260                 265                 270

Leu Glu Ile Arg Phe Glu Glu Cys Pro Gly Thr Lys Val His Val Glu
            275                 280                 285

Glu Thr Cys Gly Thr Arg Gly Pro Ser Leu Arg Ser Thr Thr Ala Ser
            290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Met Val Thr Ala
            340                 345                 350

Leu Glu His His His His His His His His
            355                 360

<210> SEQ ID NO 11
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide; Zika virus envelope glycoprotein

<400> SEQUENCE: 11

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
        50                  55                  60

Ile Ser Asp Met Ala Ser Asp Ser Arg Cys Pro Thr Gln Gly Glu Ala
65              70                  75                  80
```

```
Tyr Leu Asp Lys Gln Ser Asp Thr Gln Tyr Val Cys Lys Arg Thr Leu
             85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
            115                 120                 125

Ser Ile Gln Pro Glu Asn Leu Glu Tyr Arg Ile Met Leu Ser Val His
        130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175

Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
        210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
        290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
            340                 345                 350

Arg Leu Ile Thr Ala Asn Pro Val Ile Thr Glu Ser Thr Glu Asn Ser
        355                 360                 365

Lys Met Met Leu Glu Leu Asp Pro Pro Phe Gly Asp Ser Tyr Ile Val
        370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
            420                 425                 430

Val Phe Asn Ser Leu Gly Lys Gly Ile His Gln Ile Phe Gly Ala Ala
        435                 440                 445

Phe Lys Ser Leu Phe Gly Gly Met Ser Trp Phe Ser Gln Ile Leu Ile
        450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495
```

Ala Val Ser Ala
            500

<210> SEQ ID NO 12
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide; Dengue virus 1 envelope glycoprotein

<400> SEQUENCE: 12

Met Arg Cys Val Gly Ile Gly Ser Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Leu Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Thr Gln Asp Glu Lys Gly Val Thr Gln Asn Arg Leu Ile Thr
            340                 345                 350

Ala Asn Pro Ile Val Thr Asp Lys Glu Lys Pro Val Asn Ile Glu Thr
          355                 360                 365

Glu Pro Pro Phe Gly Glu Ser Tyr Ile Val Val Gly Ala Gly Glu Lys
          370                 375                 380

Ala Leu Lys Gln Cys Trp Phe Lys Lys Gly Ser Ser Ile Gly Lys Met
385                 390                 395                 400

Phe Glu Ala Thr Ala Arg Gly Ala Arg Arg Met Ala Ile Leu Gly Asp
              405                 410                 415

Thr Ala Trp Asp Phe Gly Ser Ile Gly Gly Val Phe Thr Ser Val Gly
              420                 425                 430

Lys Leu Val His Gln Val Phe Gly Thr Ala Tyr Gly Val Leu Phe Ser
              435                 440                 445

Gly Val Ser Trp Thr Met Lys Ile Gly Ile Gly Ile Leu Leu Thr Trp
              450                 455                 460

Leu Gly Leu Asn Ser Arg Ser Thr Ser Leu Ser Met Thr Cys Ile Ala
465                 470                 475                 480

Val Gly Met Val Thr Leu Tyr Leu Gly Val Met Val Gln Ala
              485                 490

<210> SEQ ID NO 13
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide; Dengue virus 2 envelope glycoprotein

<400> SEQUENCE: 13

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
              20                  25                  30

Thr Met Ala Lys Asn Lys Pro Thr Leu Asp Phe Glu Leu Ile Glu Thr
          35                  40                  45

Glu Ala Lys Gln Pro Ala Thr Leu Arg Lys Tyr Cys Ile Glu Ala Lys
      50                  55                  60

Leu Thr Asn Thr Thr Thr Asp Ser Arg Cys Pro Thr Gln Gly Glu Pro
65                  70                  75                  80

Ser Leu Asn Glu Glu Gln Asp Lys Arg Phe Val Cys Lys His Ser Met
                  85                  90                  95

Val Asp Arg Gly Trp Gly Asn Gly Cys Gly Leu Phe Gly Lys Gly Gly
              100                 105                 110

Ile Val Thr Cys Ala Met Phe Thr Cys Lys Lys Asn Met Lys Gly Lys
          115                 120                 125

Val Val Gln Pro Glu Asn Leu Glu Tyr Thr Ile Val Ile Thr Pro His
      130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                  165                 170                 175

Gly Tyr Gly Thr Val Thr Met Glu Cys Ser Pro Arg Thr Gly Leu Asp
              180                 185                 190

Phe Asn Glu Met Val Leu Leu Gln Met Glu Asn Lys Ala Trp Leu Val
          195                 200                 205

His Arg Gln Trp Phe Leu Asp Leu Pro Leu Pro Trp Leu Pro Gly Ala

```
                    210                 215                 220
Asp Thr Gln Gly Ser Asn Trp Ile Gln Lys Glu Thr Leu Val Thr Phe
225                 230                 235                 240

Lys Asn Pro His Ala Lys Lys Gln Asp Val Val Leu Gly Ser Gln
                245                 250                 255

Glu Gly Ala Met His Thr Ala Leu Thr Gly Ala Thr Glu Ile Gln Met
                260                 265                 270

Ser Ser Gly Asn Leu Leu Phe Thr Gly His Leu Lys Cys Arg Leu Arg
            275                 280                 285

Met Asp Lys Leu Gln Leu Lys Gly Met Ser Tyr Ser Met Cys Thr Gly
        290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
                340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Ile Gly Val Glu Pro
        370                 375                 380

Gly Gln Leu Lys Leu Asn Trp Phe Lys Lys Gly Ser Ser Ile Gly Gln
385                 390                 395                 400

Met Ile Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
                420                 425                 430

Gly Lys Ala Leu His Gln Val Phe Gly Ala Ile Tyr Gly Ala Ala Phe
            435                 440                 445

Ser Gly Val Ser Trp Ile Met Lys Ile Leu Ile Gly Val Ile Ile Thr
        450                 455                 460

Trp Ile Gly Met Asn Ser Arg Ser Thr Ser Leu Ser Val Ser Leu Val
465                 470                 475                 480

Leu Val Gly Val Val Thr Leu Tyr Leu Gly Val Met Val Gln Ala
                485                 490                 495

<210> SEQ ID NO 14
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide; Dengue virus 3 envelope glycoprotein

<400> SEQUENCE: 14

Met Arg Cys Val Gly Val Gly Asn Arg Asp Phe Val Glu Gly Leu Ser
1               5                   10                  15

Gly Ala Thr Trp Val Asp Val Val Leu Glu His Gly Gly Cys Val Thr
                20                  25                  30

Thr Met Ala Lys Asn Lys Pro Thr Leu Asp Ile Glu Leu Gln Lys Thr
            35                  40                  45

Glu Ala Thr Gln Leu Ala Thr Leu Arg Lys Leu Cys Ile Glu Gly Lys
        50                  55                  60

Ile Thr Asn Ile Thr Thr Asp Ser Arg Cys Pro Thr Gln Gly Glu Ala
65                  70                  75                  80
```

```
Ile Leu Pro Glu Glu Gln Asp Gln Asn Tyr Val Cys Lys His Thr Tyr
                85                  90                  95
Val Asp Arg Gly Trp Gly Asn Gly Cys Gly Leu Phe Gly Lys Gly Ser
            100                 105                 110
Leu Val Thr Cys Ala Lys Phe Gln Cys Leu Glu Ser Ile Glu Gly Lys
        115                 120                 125
Val Val Gln His Glu Asn Leu Lys Tyr Thr Val Ile Thr Val His
130                 135                 140
Thr Gly Asp Gln His Gln Val Gly Asn Glu Thr Gln Gly Val Thr Ala
145                 150                 155                 160
Glu Ile Thr Ser Gln Ala Ser Thr Ala Glu Ala Ile Leu Pro Glu Tyr
                165                 170                 175
Gly Thr Leu Gly Leu Glu Cys Ser Pro Arg Thr Gly Leu Asp Phe Asn
            180                 185                 190
Glu Met Ile Leu Leu Thr Met Lys Asn Lys Ala Trp Met Val His Arg
        195                 200                 205
Gln Trp Phe Phe Asp Leu Pro Leu Pro Trp Thr Ser Gly Ala Thr Thr
    210                 215                 220
Lys Thr Pro Thr Trp Asn Arg Lys Glu Leu Leu Val Thr Phe Lys Asn
225                 230                 235                 240
Ala His Ala Lys Lys Gln Glu Val Val Val Leu Gly Ser Gln Glu Gly
                245                 250                 255
Ala Met His Thr Ala Leu Thr Gly Ala Thr Glu Ile Gln Thr Ser Gly
            260                 265                 270
Gly Thr Ser Ile Phe Ala Gly His Leu Lys Cys Arg Leu Lys Met Asp
        275                 280                 285
Lys Leu Lys Leu Lys Gly Met Ser Tyr Ala Met Cys Leu Asn Thr Phe
    290                 295                 300
Val Leu Lys Lys Glu Val Ser Glu Thr Gln His Gly Thr Ile Leu Ile
305                 310                 315                 320
Lys Val Glu Tyr Lys Gly Glu Asp Ala Pro Cys Lys Ile Pro Phe Ser
                325                 330                 335
Thr Glu Asp Gly Gln Gly Lys Ala His Asn Gly Arg Leu Ile Thr Ala
            340                 345                 350
Asn Pro Val Val Thr Lys Lys Glu Glu Pro Val Asn Ile Glu Ala Glu
        355                 360                 365
Pro Pro Phe Gly Glu Ser Asn Ile Val Ile Gly Ile Gly Asp Lys Ala
    370                 375                 380
Leu Lys Ile Asn Trp Tyr Arg Lys Gly Ser Ser Ile Gly Lys Met Phe
385                 390                 395                 400
Glu Ala Thr Ala Arg Gly Ala Arg Arg Met Ala Ile Leu Gly Asp Thr
                405                 410                 415
Ala Trp Asp Phe Gly Ser Val Gly Gly Val Leu Asn Ser Leu Gly Lys
            420                 425                 430
Met Val His Gln Ile Phe Gly Ser Ala Tyr Thr Ala Leu Phe Ser Gly
        435                 440                 445
Val Ser Trp Ile Met Lys Ile Gly Ile Gly Val Leu Leu Thr Trp Ile
    450                 455                 460
Gly Leu Asn Ser Lys Asn Thr Ser Met Ser Phe Ser Cys Ile Ala Ile
465                 470                 475                 480
Gly Ile Ile Thr Leu Tyr Leu Gly Val Val Gln Ala
                485                 490
```

```
<210> SEQ ID NO 15
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide; Dengue virus 4 envelope glycoprotein

<400> SEQUENCE: 15

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Thr Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Thr Val His
    130                 135                 140

Asn Gly Asp Thr His Ala Val Gly Asn Asp Thr Ser Asn His Gly Val
145                 150                 155                 160

Thr Ala Met Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Asp Gly Asn His Met Phe Ala Gly His Leu Lys Cys Lys Val Arg
        275                 280                 285

Met Glu Lys Leu Arg Ile Lys Gly Met Ser Tyr Thr Met Cys Ser Gly
    290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
            340                 345                 350

Ser Ser Thr Pro Leu Ala Glu Asn Thr Asn Ser Val Thr Asn Ile Glu
        355                 360                 365
```

```
Leu Glu Pro Pro Phe Gly Asp Ser Tyr Ile Val Ile Gly Val Gly Asn
        370                 375                 380

Ser Ala Leu Thr Leu His Trp Phe Arg Lys Gly Ser Ser Ile Gly Lys
385                 390                 395                 400

Met Phe Glu Ser Thr Tyr Arg Gly Ala Lys Arg Met Ala Ile Leu Gly
                405                 410                 415

Glu Thr Ala Trp Asp Phe Gly Ser Val Gly Gly Leu Phe Thr Ser Leu
            420                 425                 430

Gly Lys Ala Val His Gln Val Phe Gly Ser Val Tyr Thr Thr Met Phe
                435                 440                 445

Gly Gly Val Ser Trp Met Ile Arg Ile Leu Ile Gly Phe Leu Val Leu
            450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
                485                 490                 495

<210> SEQ ID NO 16
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide; West Nile virus envelope glycoprotein

<400> SEQUENCE: 16

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Asp Val Arg Ser Tyr Cys Tyr Leu Ala Ser
    50                  55                  60

Val Ser Asp Leu Ser Thr Arg Ala Ala Cys Pro Thr Met Gly Glu Ala
65                  70                  75                  80

His Asn Glu Lys Arg Ala Asp Pro Ala Phe Val Cys Lys Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Thr Thr Lys Ala Thr Gly Trp
        115                 120                 125

Ile Ile Gln Lys Glu Asn Ile Lys Tyr Glu Val Ala Ile Phe Val His
130                 135                 140

Gly Pro Thr Thr Val Glu Ser His Gly Lys Ile Gly Ala Thr Gln Ala
145                 150                 155                 160

Gly Arg Phe Ser Ile Thr Pro Ser Ala Pro Ser Tyr Thr Leu Lys Leu
                165                 170                 175

Gly Glu Tyr Gly Glu Val Thr Val Asp Cys Glu Pro Arg Ser Gly Ile
            180                 185                 190

Asp Thr Ser Ala Tyr Tyr Val Met Ser Val Gly Glu Lys Ser Phe Leu
        195                 200                 205

Val His Arg Glu Trp Phe Met Asp Leu Asn Leu Pro Trp Ser Ser Ala
    210                 215                 220

Gly Ser Thr Thr Trp Arg Asn Arg Glu Thr Leu Met Glu Phe Glu Glu
225                 230                 235                 240
```

-continued

Pro His Ala Thr Lys Gln Ser Val Val Ala Leu Gly Ser Gln Glu Gly
                245                 250                 255

Ala Leu His Gln Ala Leu Ala Gly Ala Ile Pro Val Glu Phe Ser Ser
            260                 265                 270

Asn Thr Val Lys Leu Thr Ser Gly His Leu Lys Cys Arg Val Lys Met
        275                 280                 285

Glu Lys Leu Gln Leu Lys Gly Thr Thr Tyr Gly Val Cys Ser Lys Ala
    290                 295                 300

Phe Lys Phe Ala Arg Thr Pro Ala Asp Thr Gly His Gly Thr Val Val
305                 310                 315                 320

Leu Glu Leu Gln Tyr Thr Gly Thr Asp Gly Pro Cys Lys Val Pro Ile
                325                 330                 335

Ser Ser Val Ala Ser Leu Asn Asp Leu Thr Pro Val Gly Arg Leu Val
            340                 345                 350

Thr Val Asn Pro Phe Val Ser Val Ala Thr Ala Asn Ser Lys Val Leu
        355                 360                 365

Ile Glu Leu Glu Pro Pro Phe Gly Asp Ser Tyr Ile Val Val Gly Arg
    370                 375                 380

Gly Glu Gln Gln Ile Asn His His Trp His Lys Ser Gly Ser Ser Ile
385                 390                 395                 400

Gly Lys Ala Phe Thr Thr Thr Leu Arg Gly Ala Gln Arg Leu Ala Ala
                405                 410                 415

Leu Gly Asp Thr Ala Trp Asp Phe Gly Ser Val Gly Gly Val Phe Thr
            420                 425                 430

Ser Val Gly Lys Ala Ile His Gln Val Phe Gly Ala Phe Arg Ser
        435                 440                 445

Leu Phe Gly Gly Met Ser Trp Ile Thr Gln Gly Leu Leu Gly Ala Leu
    450                 455                 460

Leu Leu Trp Met Gly Ile Asn Ala Arg Asp Arg Ser Ile Ala Met Thr
465                 470                 475                 480

Phe Leu Ala Val Gly Gly Val Leu Leu Phe Leu Ser Val Asn Val His
                485                 490                 495

Ala

<210> SEQ ID NO 17
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide; Tick-borne encephalitis virus envelope glycoprotein

<400> SEQUENCE: 17

Ser Arg Cys Thr His Leu Glu Asn Arg Asp Phe Val Thr Gly Thr Gln
1               5                   10                  15

Gly Thr Thr Arg Val Thr Leu Val Leu Glu Leu Gly Gly Cys Val Thr
            20                  25                  30

Ile Thr Ala Glu Gly Lys Pro Ser Met Asp Val Trp Leu Asp Ala Ile
        35                  40                  45

Tyr Gln Glu Lys Pro Ala Lys Thr Arg Glu Tyr Cys Leu His Ala Lys
    50                  55                  60

Leu Ser Asp Thr Lys Val Ala Ala Arg Cys Pro Thr Met Gly Pro Ala
65                  70                  75                  80

Thr Leu Thr Glu Glu His Gln Gly Gly Thr Val Cys Lys Arg Asp Gln
                85                  90                  95

Ser Asp Arg Gly Trp Gly Asn His Cys Gly Leu Phe Gly Lys Gly Ser
                100                 105                 110

Ile Val Ala Cys Val Lys Ala Ala Cys Glu Ala Lys Lys Lys Ala Thr
            115                 120                 125

Gly His Val Tyr Asp Ala Asn Arg Ile Val Tyr Thr Val Lys Val Glu
        130                 135                 140

Pro His Thr Gly Asp Tyr Val Ala Ala Asn Glu Thr His Ser Gly Arg
145                 150                 155                 160

Lys Thr Ala Ser Phe Thr Val Ser Ser Glu Lys Thr Ile Leu Thr Met
                165                 170                 175

Gly Glu Tyr Gly Asp Val Ser Leu Leu Cys Arg Val Ala Ser Gly Val
            180                 185                 190

Asp Leu Ala Gln Thr Val Ile Leu Glu Leu Asp Lys Thr Val Glu His
        195                 200                 205

Leu Pro Thr Ala Trp Gln Val His Arg Asp Trp Phe Asn Asp Leu Ala
210                 215                 220

Leu Pro Trp Lys His Glu Gly Ala Gln Asn Trp Asn Asn Ala Glu Arg
225                 230                 235                 240

Leu Val Glu Phe Gly Ala Pro His Ala Val Lys Met Asp Val Tyr Asn
                245                 250                 255

Leu Gly Asp Gln Thr Gly Val Leu Leu Lys Ala Leu Ala Gly Val Pro
            260                 265                 270

Val Ala His Ile Glu Gly Thr Lys Tyr His Leu Lys Ser Gly His Val
        275                 280                 285

Thr Cys Glu Val Gly Leu Glu Lys Leu Lys Met Lys Gly Leu Thr Tyr
290                 295                 300

Thr Met Cys Asp Lys Thr Lys Phe Thr Trp Lys Arg Ala Pro Thr Asp
305                 310                 315                 320

Ser Gly His Asp Thr Val Val Met Glu Val Thr Phe Ser Gly Thr Lys
                325                 330                 335

Pro Cys Arg Ile Pro Val Arg Ala Val Ala His Gly Ser Pro Asp Val
            340                 345                 350

Asn Val Ala Met Leu Ile Thr Pro Asn Pro Thr Ile Glu Asn Asn Gly
        355                 360                 365

Gly Gly Phe Ile Glu Met Gln Leu Pro Pro Gly Asp Asn Ile Ile Tyr
370                 375                 380

Val Gly Glu Leu Ser His Gln Trp Phe Gln Lys Gly Ser Ser Ile Gly
385                 390                 395                 400

Arg Val Phe Gln Lys Thr Lys Lys Gly Ile Glu Arg Leu Thr Val Ile
                405                 410                 415

Gly Glu His Ala Trp Asp Phe Gly Ser Ala Gly Gly Phe Leu Ser Ser
            420                 425                 430

Ile Gly Lys Ala Val His Thr Val Leu Gly Gly Ala Phe Asn Ser Ile
        435                 440                 445

Phe Gly Gly Val Gly Phe Leu Pro Lys Leu Leu Leu Gly Val Ala Leu
450                 455                 460

Ala Trp Leu Gly Leu Asn Met Arg Asn Pro Thr Met Ser Met Ser Phe
465                 470                 475                 480

Leu Leu Ala Gly Gly Leu Val Leu Ala Met Thr Leu Gly Val Gly Ala
                485                 490                 495

<210> SEQ ID NO 18
<211> LENGTH: 500

<212> TYPE: PRT
<213> ORGANISM: Artificial Sequence
<220> FEATURE:
<223> OTHER INFORMATION: Description of Artificial Sequence: Synthetic
polypeptide; Japanese encephalitis virus envelope glycoprotein

<400> SEQUENCE: 18

```
Phe Asn Cys Leu Gly Met Gly Asn Arg Asp Phe Ile Glu Gly Ala Ser
1               5                   10                  15

Gly Ala Thr Trp Val Asp Leu Val Leu Glu Gly Asp Ser Cys Leu Thr
            20                  25                  30

Ile Met Ala Asn Asp Lys Pro Thr Leu Asp Val Arg Met Ile Asn Ile
        35                  40                  45

Glu Ala Ser Gln Leu Ala Glu Val Arg Ser Tyr Cys Tyr His Ala Ser
    50                  55                  60

Val Thr Asp Ile Ser Thr Val Ala Arg Cys Pro Thr Thr Gly Glu Ala
65                  70                  75                  80

His Asn Glu Lys Arg Ala Asp Ser Ser Tyr Val Cys Lys Gln Gly Phe
                85                  90                  95

Thr Asp Arg Gly Trp Gly Asn Gly Cys Gly Leu Phe Gly Lys Gly Ser
            100                 105                 110

Ile Asp Thr Cys Ala Lys Phe Ser Cys Thr Ser Lys Ala Ile Gly Arg
        115                 120                 125

Thr Ile Gln Pro Glu Asn Ile Lys Tyr Glu Val Gly Ile Phe Val His
    130                 135                 140

Gly Thr Thr Thr Ser Glu Asn His Gly Asn Tyr Ser Ala Gln Val Gly
145                 150                 155                 160

Ala Ser Gln Ala Ala Lys Phe Thr Val Thr Pro Asn Ala Pro Ser Ile
                165                 170                 175

Thr Leu Lys Leu Gly Asp Tyr Gly Glu Val Thr Leu Asp Cys Glu Pro
            180                 185                 190

Arg Ser Gly Leu Asn Thr Glu Ala Phe Tyr Val Met Thr Val Gly Ser
        195                 200                 205

Lys Ser Phe Leu Val His Arg Glu Trp Phe His Asp Leu Ala Leu Pro
    210                 215                 220

Trp Thr Ser Pro Ser Ser Thr Ala Trp Arg Asn Arg Glu Leu Leu Met
225                 230                 235                 240

Glu Phe Glu Glu Ala His Ala Thr Lys Gln Ser Val Val Ala Leu Gly
                245                 250                 255

Ser Gln Glu Gly Gly Leu His Gln Ala Leu Ala Gly Ala Ile Val Val
            260                 265                 270

Glu Tyr Ser Ser Ser Val Lys Leu Thr Ser Gly His Leu Lys Cys Arg
        275                 280                 285

Leu Lys Met Asp Lys Leu Ala Leu Lys Gly Thr Thr Tyr Gly Met Cys
    290                 295                 300

Thr Glu Lys Phe Ser Phe Ala Lys Asn Pro Ala Asp Thr Gly His Gly
305                 310                 315                 320

Thr Val Val Ile Glu Leu Ser Tyr Ser Gly Ser Asp Gly Pro Cys Lys
                325                 330                 335

Ile Pro Ile Val Ser Val Ala Ser Leu Asn Asp Met Thr Pro Val Gly
            340                 345                 350

Arg Leu Val Thr Val Asn Pro Phe Val Ala Thr Ser Ser Ala Asn Ser
        355                 360                 365

Lys Val Leu Val Glu Met Glu Pro Pro Phe Gly Asp Ser Tyr Ile Val
    370                 375                 380
```

```
Val Gly Arg Gly Asp Lys Gln Ile Asn His His Trp His Lys Ala Gly
385                 390                 395                 400

Ser Thr Leu Gly Lys Ala Phe Ser Thr Thr Leu Lys Gly Ala Gln Arg
                405                 410                 415

Leu Ala Ala Leu Gly Asp Thr Ala Trp Asp Phe Gly Ser Ile Gly Gly
                420                 425                 430

Val Phe Asn Ser Ile Gly Lys Ala Val His Gln Val Phe Gly Gly Ala
                435                 440                 445

Phe Arg Thr Leu Phe Gly Gly Met Ser Trp Ile Thr Gln Gly Leu Met
            450                 455                 460

Gly Ala Leu Leu Leu Trp Met Gly Val Asn Ala Arg Asp Arg Ser Ile
465                 470                 475                 480

Ala Leu Ala Phe Leu Ala Thr Gly Gly Val Leu Val Phe Leu Ala Thr
                485                 490                 495

Asn Val His Ala
            500

<210> SEQ ID NO 19
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide; Powassan virus NS1 antigen

<400> SEQUENCE: 19

Asp Tyr Gly Cys Ala Ile Asp Pro Glu Arg Met Glu Ile Arg Cys Gly
1               5                   10                  15

Glu Gly Leu Val Val Trp Lys Glu Val Ser Glu Trp Tyr Asp Gly Tyr
                20                  25                  30

Ala Tyr His Pro Glu Ser Pro Asp Thr Leu Ala Gln Ala Leu Arg Glu
            35                  40                  45

Ala Phe Glu Arg Gly Val Cys Gly Val Val Pro Gln Asn Arg Leu Glu
        50                  55                  60

Met Ala Met Trp Arg Ser Thr Ala Pro Glu Leu Asn Leu Val Leu Ser
65                  70                  75                  80

Glu Gly Glu Ala Asn Leu Thr Ile Val Val Asp Lys Thr Asp Pro Ala
                85                  90                  95

Asp Tyr Arg Gly Gly Thr Pro Met Val Leu Lys Lys Thr Gly Lys Glu
            100                 105                 110

Ser Lys Val Ser Trp Lys Ser Trp Gly Lys Ser Ile Leu Trp Ser Val
        115                 120                 125

Pro Asp Ser Pro Arg Arg Met Met Gly Val Asp Gly Val Gly Glu
130                 135                 140

Cys Pro Leu Tyr Arg Arg Ala Thr Gly Val Phe Thr Val Ala Glu Phe
145                 150                 155                 160

Gly Val Gly Leu Arg Thr Lys Val Phe Leu Asp Leu Arg Gly Glu Ala
                165                 170                 175

Ser Lys Glu Cys Asp Thr Gly Val Met Gly Ala Ala Val Lys Asn Gly
            180                 185                 190

Lys Ala Ile His Thr Asp Gln Ser Met Trp Met Ser Ser Phe Arg Asn
        195                 200                 205

Asp Thr Gly Thr Tyr Ile His Glu Leu Ile Leu Thr Asp Leu Arg Asn
    210                 215                 220

Cys Thr Trp Pro Ala Ser His Thr Ile Asp Asn Asp Gly Val Leu Asp
```

```
                225                 230                 235                 240
Ser His Leu Phe Leu Pro Val Thr Leu Ala Gly Pro Arg Ser Lys Tyr
                    245                 250                 255

Asn Arg Ile Pro Gly Tyr Ser Glu Gln Val Arg Gly Pro Trp Asp Gln
                    260                 265                 270

Thr Pro Leu Arg Val Val Arg Asp His Cys Pro Gly Thr Ser Val Arg
                    275                 280                 285

Ile Asp Ser His Cys Asp Lys Arg Gly Ala Ser Val Arg Ser Thr Thr
                290                 295                 300

Glu Ser Gly Lys Ile Ile Pro Glu Trp Cys Cys Arg Ala Cys Glu Leu
305                 310                 315                 320

Pro Pro Val Thr Phe Arg Ser Gly Thr Asp Cys Trp Tyr Ala Met Glu
                    325                 330                 335

Ile Arg Pro Val His Ser Gln Gly Gly Leu Val Arg Ser Met Val Val
                340                 345                 350

Ala

<210> SEQ ID NO 20
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide; Zika virus NS1 antigen with C-terminal His tag and
      additional fused peptide

<400> SEQUENCE: 20

Met Lys His Leu Trp Phe Phe Leu Leu Leu Val Ala Ala Pro Arg Trp
1               5                   10                  15

Val Leu Ser Gly Pro Met Asp Val Gly Cys Ser Val Asp Phe Ser Lys
                20                  25                  30

Lys Glu Thr Arg Cys Gly Thr Gly Val Phe Val Tyr Asn Asp Val Glu
            35                  40                  45

Ala Trp Arg Asp Arg Tyr Lys Tyr His Pro Asp Ser Pro Arg Arg Leu
        50                  55                  60

Ala Ala Ala Val Lys Gln Ala Trp Glu Glu Gly Ile Cys Gly Ile Ser
65                  70                  75                  80

Ser Val Ser Arg Met Glu Asn Ile Met Trp Lys Ser Val Glu Gly Glu
                85                  90                  95

Leu Asn Ala Ile Leu Glu Glu Asn Gly Val Gln Leu Thr Val Val Val
            100                 105                 110

Gly Ser Val Lys Asn Pro Met Trp Arg Gly Pro Gln Arg Leu Pro Val
        115                 120                 125

Pro Val Asn Glu Leu Pro His Gly Trp Lys Ala Trp Gly Lys Ser Tyr
    130                 135                 140

Phe Val Arg Ala Ala Lys Thr Asn Asn Ser Phe Val Val Asp Gly Asp
145                 150                 155                 160

Thr Leu Lys Glu Cys Pro Leu Lys His Arg Ala Trp Asn Ser Phe Leu
                165                 170                 175

Val Glu Asp His Gly Phe Gly Val Phe His Thr Ser Val Trp Leu Lys
            180                 185                 190

Val Arg Glu Asp Tyr Ser Leu Glu Cys Asp Pro Ala Val Ile Gly Thr
        195                 200                 205

Ala Val Lys Gly Lys Glu Ala Ala His Ser Asp Leu Gly Tyr Trp Ile
    210                 215                 220
```

```
Glu Ser Glu Lys Asn Asp Thr Trp Arg Leu Lys Arg Ala His Leu Ile
225                 230                 235                 240

Glu Met Lys Thr Cys Glu Trp Pro Lys Ser His Thr Leu Trp Thr Asp
            245                 250                 255

Gly Val Glu Glu Ser Asp Leu Ile Ile Pro Lys Ser Leu Ala Gly Pro
        260                 265                 270

Leu Ser His His Asn Thr Arg Glu Gly Tyr Arg Thr Gln Val Lys Gly
    275                 280                 285

Pro Trp His Ser Glu Glu Leu Glu Ile Arg Phe Glu Glu Cys Pro Gly
290                 295                 300

Thr Lys Val His Val Glu Glu Thr Cys Gly Thr Arg Gly Pro Ser Leu
305                 310                 315                 320

Arg Ser Thr Thr Ala Ser Gly Arg Val Ile Glu Glu Trp Cys Cys Arg
            325                 330                 335

Glu Cys Thr Met Pro Pro Leu Ser Phe Arg Ala Lys Asp Gly Cys Trp
            340                 345                 350

Tyr Gly Met Glu Ile Arg Pro Arg Lys Glu Pro Glu Ser Asn Leu Val
        355                 360                 365

Arg Ser Met Val Thr Ala Leu Glu His His His His His His His
    370                 375                 380
```

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide; Zika virus NS1 epitope

<400> SEQUENCE: 21

```
Arg Met Glu Asn Ile Met Trp Lys Ser Val Glu Gly
1               5                   10
```

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide; Zika virus NS1 epitope

<400> SEQUENCE: 22

```
Gln Arg Leu Pro Val Pro Val Asn Glu
1               5
```

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide; Zika virus NS1 epitope

<400> SEQUENCE: 23

```
Ser Tyr Phe Val Arg Ala Ala Lys Thr
1               5
```

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic

```
               peptide; Zika virus NS1 epitope

<400> SEQUENCE: 24

Asp Thr Leu Lys
1

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide; Zika virus NS1 epitope

<400> SEQUENCE: 25

Asp Tyr Ser Leu Glu
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide; Zika virus NS1 epitope

<400> SEQUENCE: 26

Ser Phe Arg Ala Lys
1               5

<210> SEQ ID NO 27
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide; Yellow fever virus envelope glycoprotein

<400> SEQUENCE: 27

Ala His Cys Ile Gly Ile Thr Asp Arg Asp Phe Ile Glu Gly Val His
1               5                   10                  15

Gly Gly Thr Trp Val Ser Ala Thr Leu Glu Gln Asp Lys Cys Val Thr
            20                  25                  30

Val Met Ala Pro Asp Lys Pro Ser Leu Asp Ile Ser Leu Glu Thr Val
        35                  40                  45

Ala Ile Asp Gly Pro Ala Glu Ala Arg Lys Val Cys Tyr Asn Ala Val
    50                  55                  60

Leu Thr His Val Lys Ile Asn Asp Lys Cys Pro Ser Thr Gly Glu Ala
65                  70                  75                  80

His Leu Ala Glu Glu Asn Glu Gly Asp Asn Ala Cys Lys Arg Thr Tyr
                85                  90                  95

Ser Asp Arg Gly Trp Gly Asn Gly Cys Gly Leu Phe Gly Lys Gly Ser
            100                 105                 110

Ile Val Ala Cys Ala Lys Phe Thr Cys Ala Lys Ser Met Ser Leu Phe
        115                 120                 125

Glu Val Asp Gln Thr Lys Ile Gln Tyr Val Ile Arg Ala Gln Leu His
    130                 135                 140

Val Gly Ala Lys Gln Glu Asn Trp Asn Thr Asp Ile Lys Thr Leu Lys
145                 150                 155                 160

Phe Asp Ala Leu Ser Gly Ser Gln Glu Ala Glu Phe Thr Gly Tyr Gly
                165                 170                 175
```

```
Lys Ala Thr Leu Glu Cys Gln Val Gln Thr Ala Val Asp Phe Gly Asn
            180                 185                 190
Ser Tyr Ile Ala Glu Met Glu Lys Glu Ser Trp Ile Val Asp Arg Gln
        195                 200                 205
Trp Ala Gln Asp Leu Thr Leu Pro Trp Gln Ser Gly Ser Gly Gly Val
        210                 215                 220
Trp Arg Glu Met His His Leu Val Glu Phe Glu Pro Pro His Ala Ala
225                 230                 235                 240
Thr Ile Arg Val Leu Ala Leu Gly Asn Gln Glu Gly Ser Leu Lys Thr
                245                 250                 255
Ala Leu Thr Gly Ala Met Arg Val Thr Lys Asp Thr Asn Asp Asn Asn
            260                 265                 270
Leu Tyr Lys Leu His Gly Gly His Val Ser Cys Arg Val Lys Leu Ser
        275                 280                 285
Ala Leu Thr Leu Lys Gly Thr Ser Tyr Lys Met Cys Thr Asp Lys Met
        290                 295                 300
Ser Phe Val Lys Asn Pro Thr Asp Thr Gly His Gly Thr Val Val Met
305                 310                 315                 320
Gln Val Lys Val Pro Lys Gly Ala Pro Cys Lys Ile Pro Val Ile Val
                325                 330                 335
Ala Asp Asp Leu Thr Ala Ala Ile Asn Lys Gly Ile Leu Val Thr Val
            340                 345                 350
Asn Pro Ile Ala Ser Thr Asn Asp Asp Glu Val Leu Ile Glu Val Asn
        355                 360                 365
Pro Pro Phe Gly Asp Ser Tyr Ile Ile Val Gly Thr Gly Asp Ser Arg
        370                 375                 380
Leu Thr Tyr Gln Trp His Lys Glu Gly Ser Ser Ile Gly Lys Leu Phe
385                 390                 395                 400
Thr Gln Thr Met Lys Gly Ala Glu Arg Leu Ala Val Met Gly Asp Ala
                405                 410                 415
Ala Trp Asp Phe Ser Ser Ala Gly Gly Phe Phe Thr Ser Val Gly Lys
            420                 425                 430
Gly Ile His Thr Val Phe Gly Ser Ala Phe Gln Gly Leu Phe Gly Gly
        435                 440                 445
Leu Asn Trp Ile Thr Lys Val Ile Met Gly Ala Val Leu Ile Trp Val
        450                 455                 460
Gly Ile Asn Thr Arg Asn Met Thr Met Ser Met Ser Met Ile Leu Val
465                 470                 475                 480
Gly Val Ile Met Met Phe Leu Ser Leu Gly Val Gly Ala
                485                 490
```

IMMUNOASSAY FOR THE DIAGNOSIS OF VIRAL INFECTIONS

CROSS-REFERENCE TO RELATED APPLICATIONS

This application is a divisional application of U.S. application Ser. No. 16/077,757, filed on Aug. 14, 2018, which is a National Stage entry under § 371 of International App. No. PCT/EP2017/000249, filed on Feb. 22, 2017, and which claims the benefit of European App. No. 16000422.2, filed on Feb. 22, 2016; European App. No. 16000442.0, filed on Feb. 24, 2016; European App. No. 16000454.5 filed on Feb. 25, 2016; and European App. No. 16000747.2 filed on Mar. 31, 2016. The content of each of these applications is hereby incorporated by reference in its entirety.

REFERENCE TO A SEQUENCE LISTING

The present application is accompanied by an ASCII text file as a computer readable form containing the sequence listing, titled "000630USDIV01_SL_ST25.txt" created on Oct. 1, 2020 with the file size of 81,920 bytes, which is incorporated by reference in its entirety.

BACKGROUND OF THE INVENTION

Field of the Invention

Aspects of the present inventions relate to a polypeptide comprising a sequence selected from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9 or a variant thereof, preferably SEQ ID NO: 1 or a variant thereof, preferably a dimer and/or hexamer thereof, more preferably a dimer thereof, for the diagnosis of a disease, a diagnostically useful carrier comprising a means for specifically capturing an antibody to SEQ ID NO: 1 in a sample from a subject, a kit comprising the diagnostically useful carrier, and a method, preferably for diagnosing a disease, comprising the step detecting in a sample from a subject the presence or absence of an antibody to SEQ ID NO: 1.

Description of the Related Art

Zika virus (ZIKV) is an emerging mosquito-transmitted flavivirus currently causing large epidemics in South and Central America as well as in the Caribbean. It is closely related to other human pathogenic members of the flavivirus family like dengue (DENV), West Nile (WNV), Powassan virus (PWV), Japanese encephalitis (JEV), Usutsu and Yellow Fever (YFV) virus. Besides their structural resemblance, most of these viruses share a partially overlapping geographical distribution, tropical and sub-tropical regions representing the favorable environment of the main vector, mosquitos of the genus *Aedes*.

Clinically, Zika fever resembles dengue fever, but is generally less severe. As over 80% of infections are asymptomatic, most cases remain unnoticed. The symptoms comprise fever, rash, arthralgia and conjunctivitis and infections are normally self-limiting. In contrast, in 5% of DENV infections, severe complications lead to the dengue shock syndrome or dengue hemorrhagic fever with high mortality rates. The current ZIKV epidemic, in particular in Brazil, has hardened the suspicion about two potential severe complications in ZIKV infections initially suspected during the 2007 outbreak in Micronesia. Firstly, a significant raise in cases of the rare Guillain-Barré syndrome (GBS), an autoimmune disease resulting in damage of the peripheral nerve myelin, was triggered by infections. Secondly, a 20-fold increase in microcephaly cases in newborns from the highly endemic regions in Brazil, followed by the first reports of ZIKV genome detection in the amniotic fluid of two pregnant women, carrying fetuses with microcephaly, and in the brain of a fetus aborted after the intrauterine diagnosis of microcephaly, provided a strong causative link between fetal abnormalities and ZIKV infection during early pregnancy.

Besides the two representatives from the flavivirus family, chikungunya virus (CHIKV), a member of the Alphavirus family, should also be considered in the differential diagnosis. CHIKV is transmitted by the same mosquito vector and is endemic in the same regions. The common distribution and similar clinical presentation in combination with high varieties in disease outcome and the necessity of differentiated treatment of ZIKV, DENV and CHIKV infected patients substantiate the need for specific and reliable diagnostic possibilities.

At present, diagnosis of ZIKV infections is challenging, because the only specific tool is direct proof of viraemia using nucleic acid-based testing, but the viraemic phase usually lasts only up to seven days after symptom onset. Thus, methods such as RT-PCR may already give negative results by the time a patient consults their doctor. Plaque-reduction neutralization tests (PRNT) can measure virus-specific neutralizing antibodies and discriminate between cross-reacting antibodies. This is highly relevant in regions where two or more flaviviruses co-occur. However, PRNT is time-consuming, difficult to perform and not amenable to testing large numbers of sera. In contrast, ELISA-based measurement of virus-specific antibody response is a rapid, scalable and technically mature approach. As reported, IgM antibodies are produced starting four to seven days after symptom onset and IgG antibodies appear a few days later.

A major limitation of conventional serological assays for diagnosing flaviviral infections, for example those based on glycoprotein E (gpE), is their extensive cross-reactivity within the flavivirus genus.

Another limitation is the fact that a range of patients, particular with a background of past flavivirus infections, appear to be deficient in IgM, which is an antibody class that may emerge at the early stage of flavirus infection, prior to detectable levels of IgG class antibodies. In such patients, the results of IgM-based diagnostic tests, as frequently used for the diagnosis of flavivirus infections, give a false-negative result, with severe implications for the health of the patients and, if they are pregnant, their babies.

Another limitation, which concerns research into the field of flavivirus such as Zika virus infections, for example the diagnosis or therapy of flavivirus infections or any basic research, is that sera from patients with confirmed Zika infections are in short supply. Quite often not only one sample is required, but several samples taken from a range of time points following infection or the onset of symptoms, for example if the kinetics of the disease is investigated or control samples are required for studies related to a therapeutic invention at an early stage of the infection.

BRIEF SUMMARY OF THE INVENTION

Therefore, the problem underlying the present invention is to provide a diagnostic assay overcoming any shortcomings associated with state of the art assays for the diagnosis of flaviviruses such as the Zika virus, in particular those based on the detection of antibodies to flaviviral antigens.

Another problem underlying the present invention is to provide an assay that allows for the specific diagnosis of an infection, preferably a flaviviral infection, more preferably a Zika virus infection, more specifically a distinction between infections with the Zika virus and related flaviviruses such as those selected from the group comprising dengue virus, Yellow fever virus, Tick-borne encephalitis virus, Usutu virus, West Nile virus and Japanese encephalitis virus, preferably dengue virus.

Another problem underlying the present invention is to provide an assay and reagents for the detection of a flavivirus infection, wherein the sensitivity and/or specificity is improved compared to state of the art assays, in particular regarding the early phase of an infection.

Another problem underlying the present invention is to provide a vaccine against a flavivirus, preferably Zika virus infection.

Another problem underlying the present invention is to provide a resource-efficient, yet diagnostically reliable test for distinguishing a flavivirus infection from another disease.

Another problem underlying the present invention is to provide a test providing a longer time window for the diagnosis.

Another problem underlying the present invention is to provide a test that requires a lower amount of patient sample.

Another problem underlying the present invention is to provide an assay for distinguishing an acute infection by Flaviruses, in particular Zika virus, from a vaccination or a previous infection by the same or another Flavivirus, preferably dengue virus.

Another problem underlying the present invention is to provide a vaccine against a flavivirus, preferably Zika virus infection.

Another problem underlying the present invention is to provide a resource-efficient, yet diagnostically reliable test for distinguishing a flavivirus infection from another disease.

Another problem underlying the present invention is to provide a test that may be used during a longer time window between the initial exposure or the onset of symptoms and the day the sample for the diagnosis is obtained.

Another problem underlying the present invention is to provide a test for distinguishing between a primary Flavivirus infection, preferably with a Flavivirus other than the Zika virus, and a secondary Flavivirus infection, preferably Zika infection, which method is diagnostically more reliable than state of the art methods, in particular with regard to avoiding false positive or negative results, and may ideally be applied to samples from patients having an IgM deficiency.

The problem underlying the present invention is solved by the subject-matter of the attached independent and dependent claims.

In a first aspect, the problem underlying the present invention is solved by a polypeptide comprising a sequence selected from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9 or a variant thereof, preferably SEQ ID NO: 1 or a variant thereof, preferably a dimer and/or hexamer, more preferably a dimer, for the diagnosis of a disease.

In a second aspect, the problem is solved by a diagnostically useful carrier comprising a means for specifically capturing an antibody to SEQ ID NO: 1 in a sample from a subject.

In a preferred embodiment, the carrier further comprises one or more than one means, which means is for specifically capturing an antibody to an antigen from the group comprising SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9.

In a preferred embodiment, the carrier is selected from the group comprising a bead, preferably a paramagnetic particle, a test strip, a microtiter plate, a blot, preferably from the group comprising western blot, line blot and dot blot, lateral flow test, a glass surface, a slide, a biochip and a membrane, and is preferably a bead a line blot or microtiter plate, more preferably a microtiter plate.

In a third aspect, the problem is solved by a kit comprising the diagnostically useful carrier according to the present invention, optionally as well as a means for specifically detecting a captured antibody.

In a preferred embodiment, the kit comprises the diagnostically useful carrier which further comprises one or more means, which means is for specifically capturing an antibody to one or more further antigens from the group comprising SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9,
  wherein the means for specifically capturing an antibody to SEQ ID NO: 1 and the means for specifically capturing an antibody to one or more further antigens are coated on, preferably covalently linked to separate carriers.

In a preferred embodiment, the kit comprises the diagnostically useful carrier which further comprises one or more means, which means is for specifically capturing an antibody to one or more further antigens from the group SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9, wherein the means for specifically capturing an antibody to SEQ ID NO: 1 and the means for specifically capturing an antibody to one or more further antigens are coated on one, preferably covalently linked to one carrier.

In a $4^{th}$ aspect, the problem is solved by a method, preferably for diagnosing a disease, comprising the step detecting in a sample from a subject the presence or absence of an antibody to SEQ ID NO: 1.

In a preferred embodiment, the method further comprises the step detecting in a sample, preferably blood or CSF sample, from a subject the presence or absence of an antibody to one or more further antigens from the group comprising SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9.

In a preferred embodiment, the presence or absence of an antibody to SEQ ID NO: 1 and the presence or absence of an antibody to one or more further antigens from the group comprising SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9 is detected simultaneously.

In a preferred embodiment, the presence or absence of an antibody to SEQ ID NO: 1 and the presence or absence of an antibody to one or more further antigens is detected in spatially separate binding reactions.

In a preferred embodiment, the presence or absence of an antibody to SEQ ID NO: 1 and the presence or absence of an antibody to one or more further antigens is detected in a one-pot reaction.

In a preferred embodiment, the method comprises the step contacting the diagnostically useful carrier according to the present invention with a sample from the subject.

In a preferred embodiment, the subject suffers from or is suspected of suffering from an infectious disease, preferably a viral infection, more preferably an infection by a flavivirus, preferably from the group comprising Zika, dengue, Yellow fever, TBEV, Usutu, Powassan, West Nile and JEV, preferably Zika.

In a preferred embodiment, the antibody is a mammalian, preferably human antibody, more preferably a human IgA, IgM or IgG class antibody, preferably IgG.

In a $5^{th}$ aspect, the problem underlying the present invention is solved by diagnostically useful carrier configured for capturing an IgA class antibody to NS1 from a flavivirus, preferably the Zika virus, in a sample from a subject,
    preferably for diagnosing a Flavivirus infection, more preferably for distinguishing a primary from a secondary Flavivirus, preferably Zika virus infection.

In a preferred embodiment, the carrier is in addition configured for capturing and specifically detecting an IgM and/or IgG class antibody, preferably an IgM class antibody, to NS1 from said Flavivirus
    and/or is in addition configured for capturing an antibody to an envelope glycoprotein of a Flavivirus.

In another preferred embodiment the diagnostically useful carrier is in complex with an IgA class antibody to NS1 from a Flavivirus.

In another preferred embodiment said complex further comprises the NS1 from a Flavivirus or a variant thereof, and preferably further comprises a detection label which is more preferably associated with an antibody to be detected or the NS1 from a Flavivirus or variant thereof.

In another preferred embodiment, the diagnostically useful carrier comprises a dimer or hexamer of the NS1 of said Flavivirus.

In a $6^{th}$ aspect, the problem is solved by a kit comprising the diagnostically useful carrier according to the present invention.

In a $7^{th}$ aspect, the problem is solved by a method for diagnosing a Flavivirus infection, preferably for distinguishing a primary from a secondary Flavivirus infection, comprising the step
    a) detecting in a first sample from a subject an IgA class antibody to NS1 of said Flavivirus.

In another preferred embodiment, the diagnostically useful carrier according to the present invention is used.

In another preferred embodiment, the method further comprises the step
    b) detecting in a second sample from said subject an IgA class antibody to NS1 of said Flavivirus,
        wherein the second sample was obtained from said subject at least three days later than the first sample.

In another preferred embodiment, in addition an IgM class antibody to NS1 of said Flavivirus is detected as part of step a) and/or step b), preferably step a).

In another preferred embodiment, an IgG class antibody to NS1 of said Flavivirus is detected in addition in step a) and/or step b), preferably step a).

In another preferred embodiment, in addition in step a) and/or step b), preferably step a), at least one class of antibody to an envelope glycoprotein of said Flavivirus is detected,
    wherein preferably the at least one class of antibody to an envelope glycoprotein of said Flavivirus is selected from the group comprising IgG, IgM and IgA, preferably IgA and IgM, or IgA and IgG, or IgM and IgG, more preferably IgA.

In another preferred embodiment, each antibody is detected in spatially separate binding reactions, separated according to antigen and antibody class to be detected.

In another preferred embodiment, the Flavivirus is selected from the group comprising Zika virus, dengue virus, Yellow fever virus, Tick-borne encephalitis virus, Usutu virus, West Nile virus and Japanese encephalitis virus, preferably Zika virus.

In an $8^{th}$ aspect, the problem is solved by a use of an IgA class antibody to NS1 from a Flavivirus, preferably the Zika virus, or a diagnostically useful carrier for immobilizing and optionally detecting said antibody, for distinguishing a primary from a secondary Flavivirus infection, preferably Zika virus infection.

In a $9^{th}$ aspect, the problem is solved by a use of an IgA class antibody to NS1 from a Flavivirus, preferably the Zika virus, or a diagnostically useful carrier for immobilizing and optionally detecting said antibody, for diagnosing a flaviviral infection, preferably a Zika virus infection, in an IgM-deficient subject.

In a $10^{th}$ aspect, the problem is solved by a use of an IgA class antibody to NS1 from a Flavivirus, preferably the Zika virus, or a diagnostically useful carrier for immobilizing and optionally detecting said antibody, for increasing the diagnostic reliability, preferably sensitivity, of a diagnostic assay for diagnosing a flaviviral infection, preferably a Zika infection, more preferably at the early stages of an infection.

BRIEF DESCRIPTION OF THE SEVERAL VIEWS OF THE DRAWINGS

Figure 1:
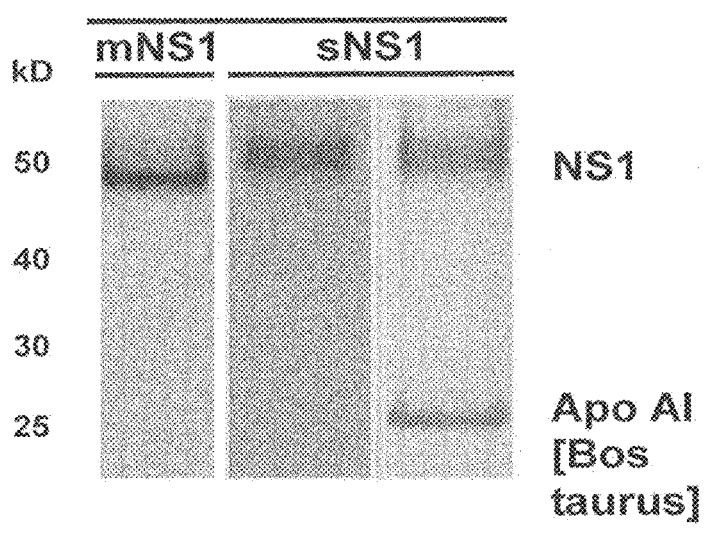

FIG. 1 shows SDS-PAGE and Coomassie staining of 1 µg purified recombinant sNS1 and mNS1, the latter pure and in complex with bovine Apolipoprotein A1. For each lane, 1 µg protein was separated on a 4-12% denaturing NuPage Bis-Tris gel, documenting high protein purity. Molecular weight markers are indicated on the left.

FIG. 2A shows the diagnostic performance for ZIKV infections (n=29) against infections or vaccinations with other flaviviruses (DENV, n=38; YFV, n=12; WNV, n=34; JEV, n=25).

FIG. 2B shows the diagnostic performance for ZIKV infections (n=29) against healthy controls (pregnant women, n=100; Argentinian blood donors, n=99; US-American blood donors, n=100; German blood donors; n=500). AUC, area under the curve.

RT-PCR: reverse transcription-PCR; US: United States; WHO: World Health Organization; ZIKV: Zika virus.

[a] Per patient, one sample was examined for anti-ZIKV IgM and IgG antibodies. Plotted data points represent ratio values (extinction$_{sample}$/extinction$_{calibrator}$). Cut-off values for borderline results (≥0.8 to <1.1) and positive results (≥1.1) are indicated by horizontal dashed lines. Positive and total cases are indicated in parentheses. Triangles indicate samples with a ratio for anti-ZIKV IgM or IgG below the cut-off (<1.1), but a corresponding positive result in IgG or IgM testing, respectively.

Figure 9A:
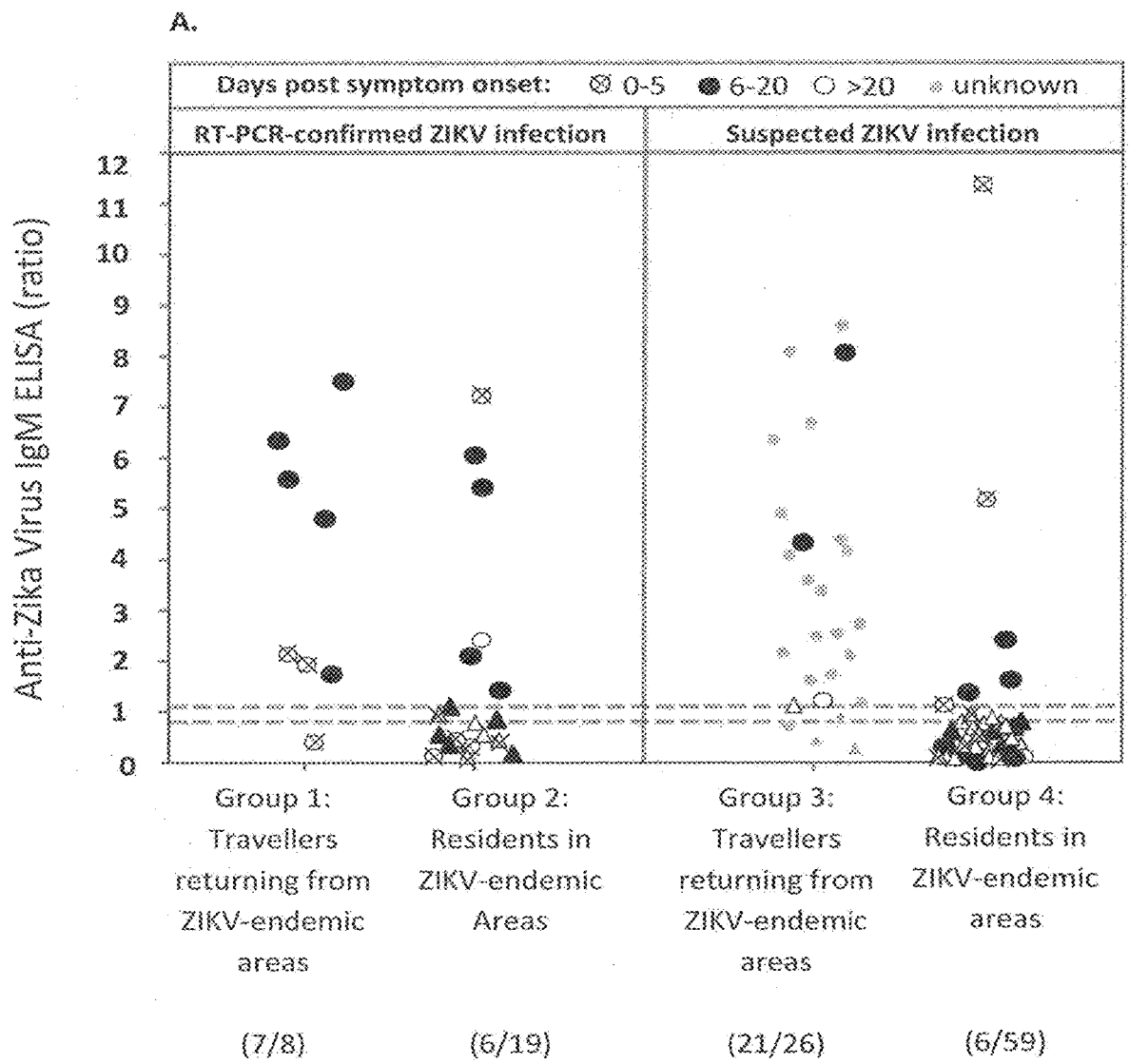
FIG. 9A shows anti-ZIKV reactivity in patients with RT-PCR-confirmed (n=27) and suspected (n=85) ZIKV infection as determined by ELISA for IgM[a].
Figure 9B:
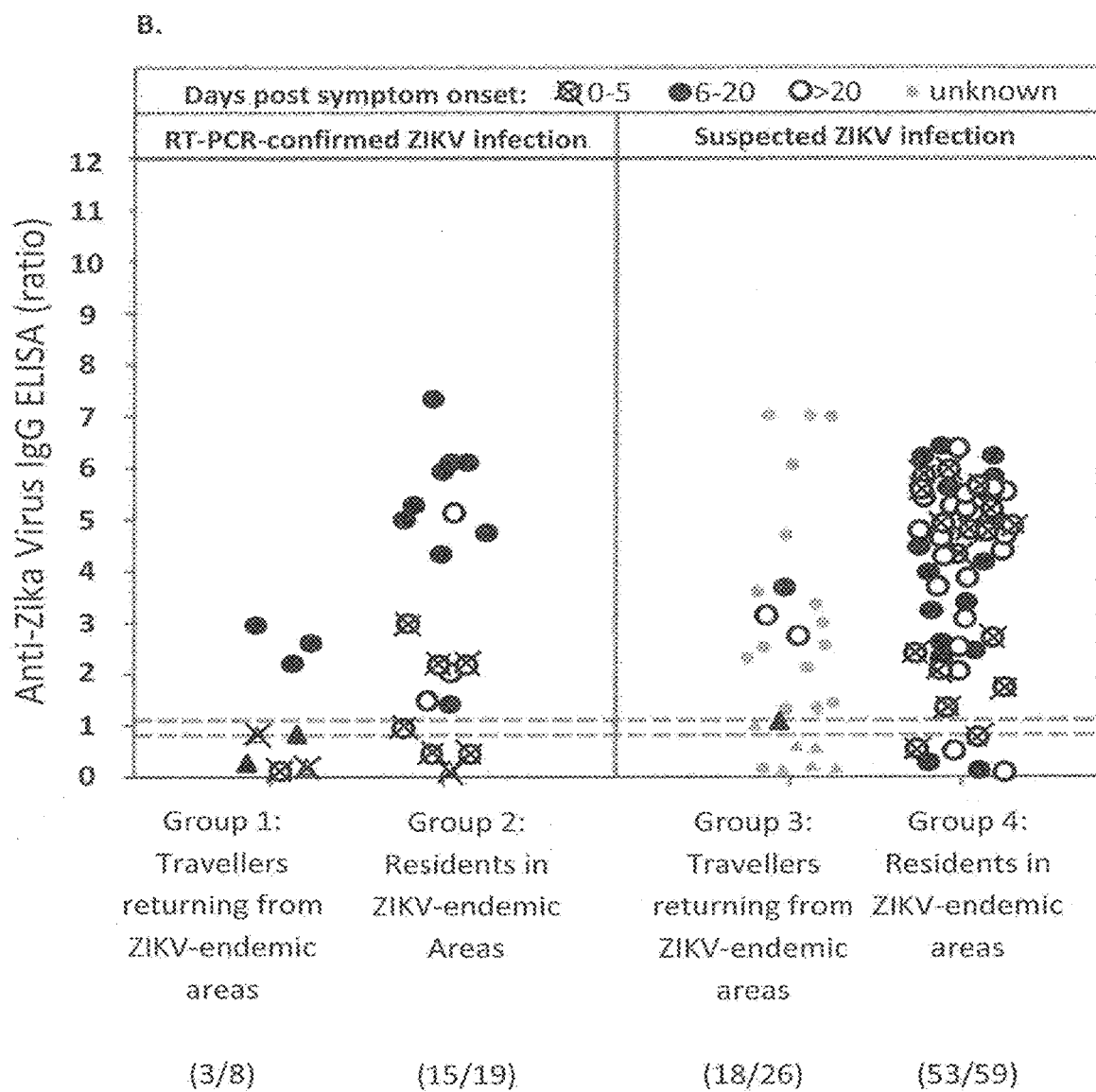

FIG. 9B shows anti-ZIKV reactivity in patients with RT-PCR-confirmed (n=27) and suspected (n=85) ZIKV infection as determined by ELISA for IgG[a].

RT-PCR: reverse transcription-PCR; US: United States; WHO: World Health Organization; ZIKV: Zika virus.

[a] Per patient, one sample was examined for anti-ZIKV IgM and IgG antibodies. Plotted data points represent ratio values (extinction$_{sample}$/extinction$_{calibrator}$). Cut-off values for borderline results (≥0.8 to <1.1) and positive results (≥1.1) are indicated by horizontal dashed lines. Positive and total cases are indicated in parentheses. Triangles indicate samples with a ratio for anti-ZIKV IgM or IgG below the cut-off (<1.1), but a corresponding positive result in IgG or IgM testing, respectively.

Figure 9C:
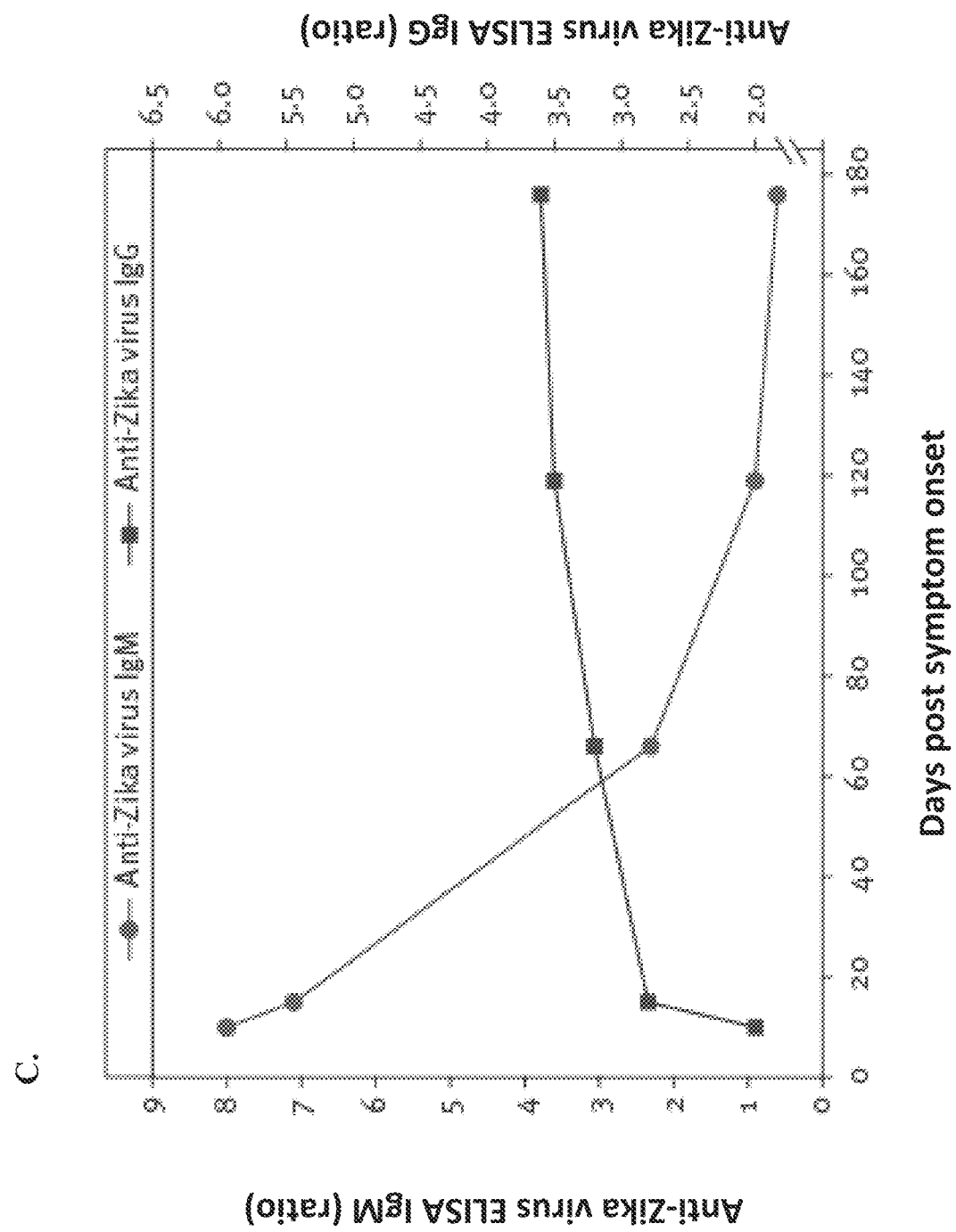

FIG. 9C shows time course analysis of anti-ZIKV antibody levels in follow-up samples from a German patient returning from Colombia (probable primary ZIKV infection)[b].

RT-PCR: reverse transcription-PCR; US: United States; WHO: World Health Organization; ZIKV: Zika virus.

[b] Samples were provided by the WHO Collaborating Centre for Arbovirus and Haemorrhagic Fever Reference and Research, Hamburg, Germany. Cut-off ratio: ≥1.1.

Figure 9D:
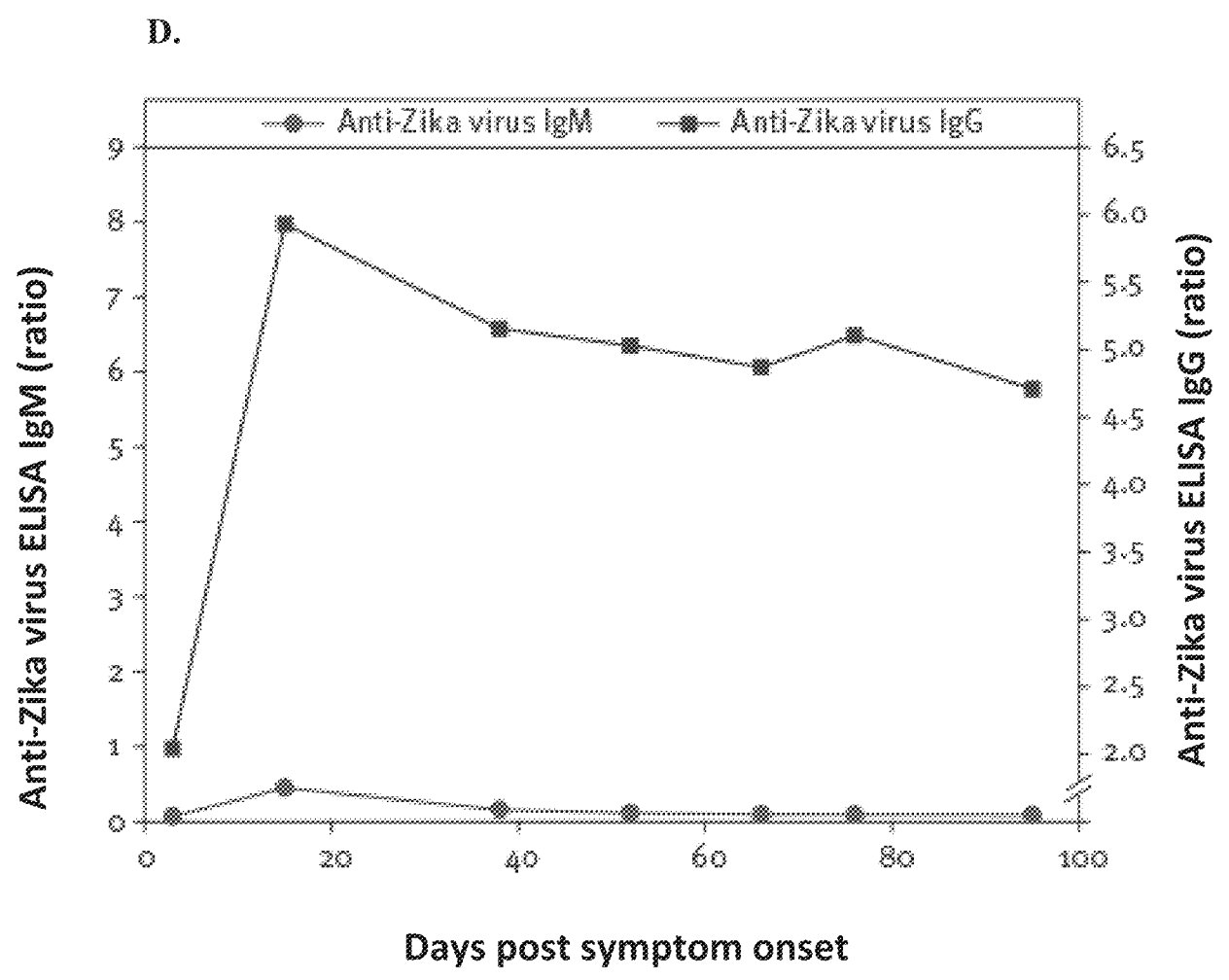

FIG. 9D shows time course analysis of anti-ZIKV antibody levels in follow-up samples from a Colombian patient with RT-PCR-confirmed ZIKV infection (probable secondary flavivirus infection)[c]

RT-PCR: reverse transcription-PCR; US: United States; WHO: World Health Organization; ZIKV: Zika virus.

[c] Samples were provided by Biomex US LLC, Coconut Creek, Florida, US. Cut-off ratio: ≥1.1.

Figure 10A:
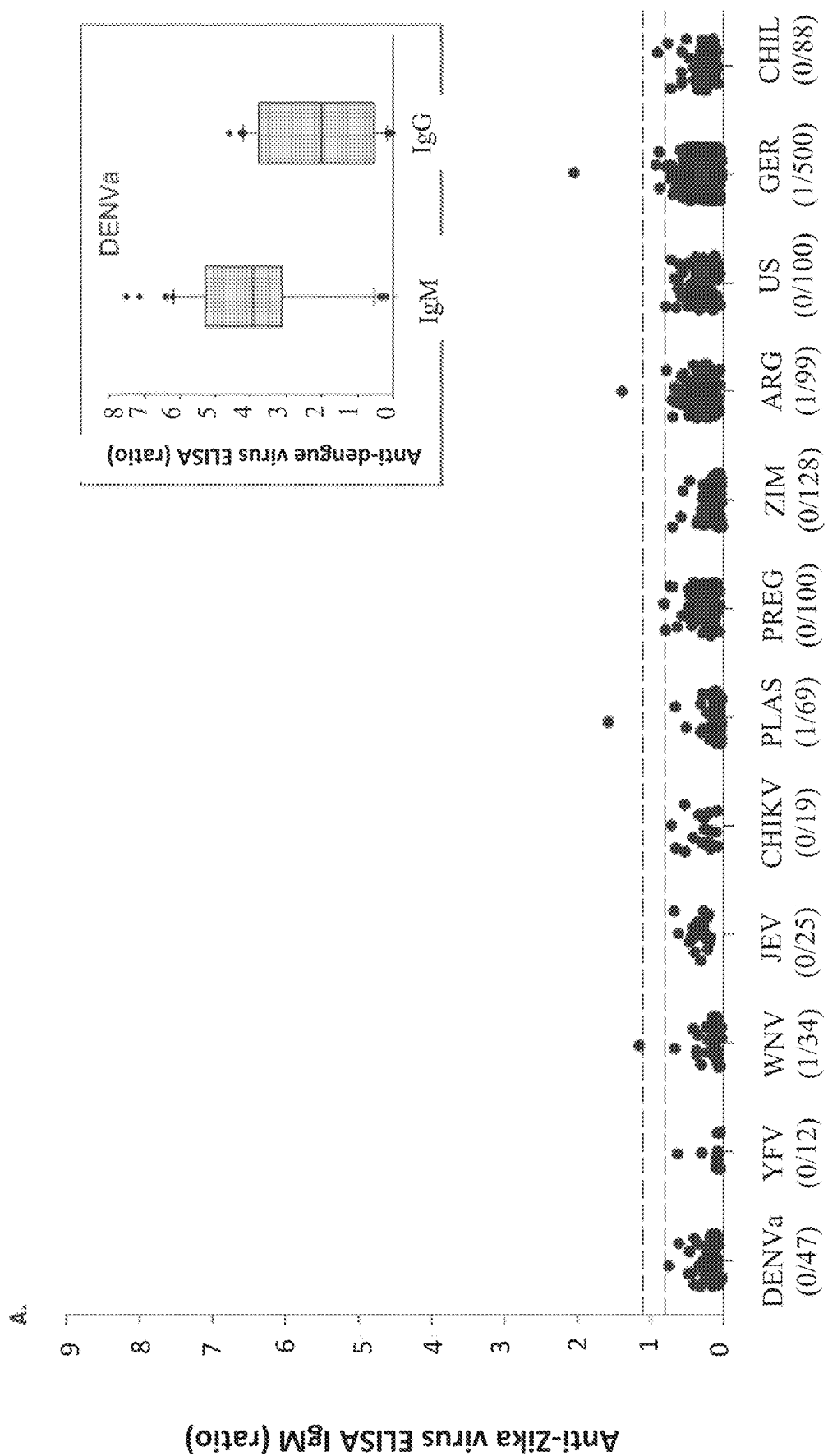

FIG. 10A shows anti-ZIKV reactivity in potentially cross-reactive samples (n=252) and healthy controls (n=1,015) as determined by ELISA for IgM[d,e], study evaluating a novel NS1-based ELISA, Germany 2016

ARG: Argentina; CHIKV: chikungunya virus; CHIL: children; DENV: dengue virus; GER: Germany; JEV: Japanese encephalitis virus; NS: non-structural protein; PLAS: *Plasmodium*; PREG: pregnant women; US: United States; WNV: West Nile virus; YFV: Yellow fever virus; ZIKV: Zika virus; ZIM: Zimbabwe.

[d] Plotted data points represent ratio values (extinction$_{sample}$/extinction$_{calibrator}$); one data point per patient. Cut-off values for borderline results (≥0.8 to <1.1) and positive results (≥1.1) are indicated by horizontal dashed lines. Positive and total cases are indicated in parentheses.

[e] To provide high levels of potentially cross-reactive anti-DENV IgM and IgG antibodies, the DENV-infected patients were divided into two groups: DENVa, high median ratio (3.9) anti-DENV IgM, anti-DENV IgM ratio ≥3.0 in 79% of cases (inset FIG. 10A); DENVb, high median ratio (3.9) anti-DENV IgG, anti-DENV IgG ratio ≥3.0 in 80% of cases (inset FIG. 10B). Cut-off ratio (anti-DENV ELISA, EUROIMMUN): ≥1.1.

Figure 10B:
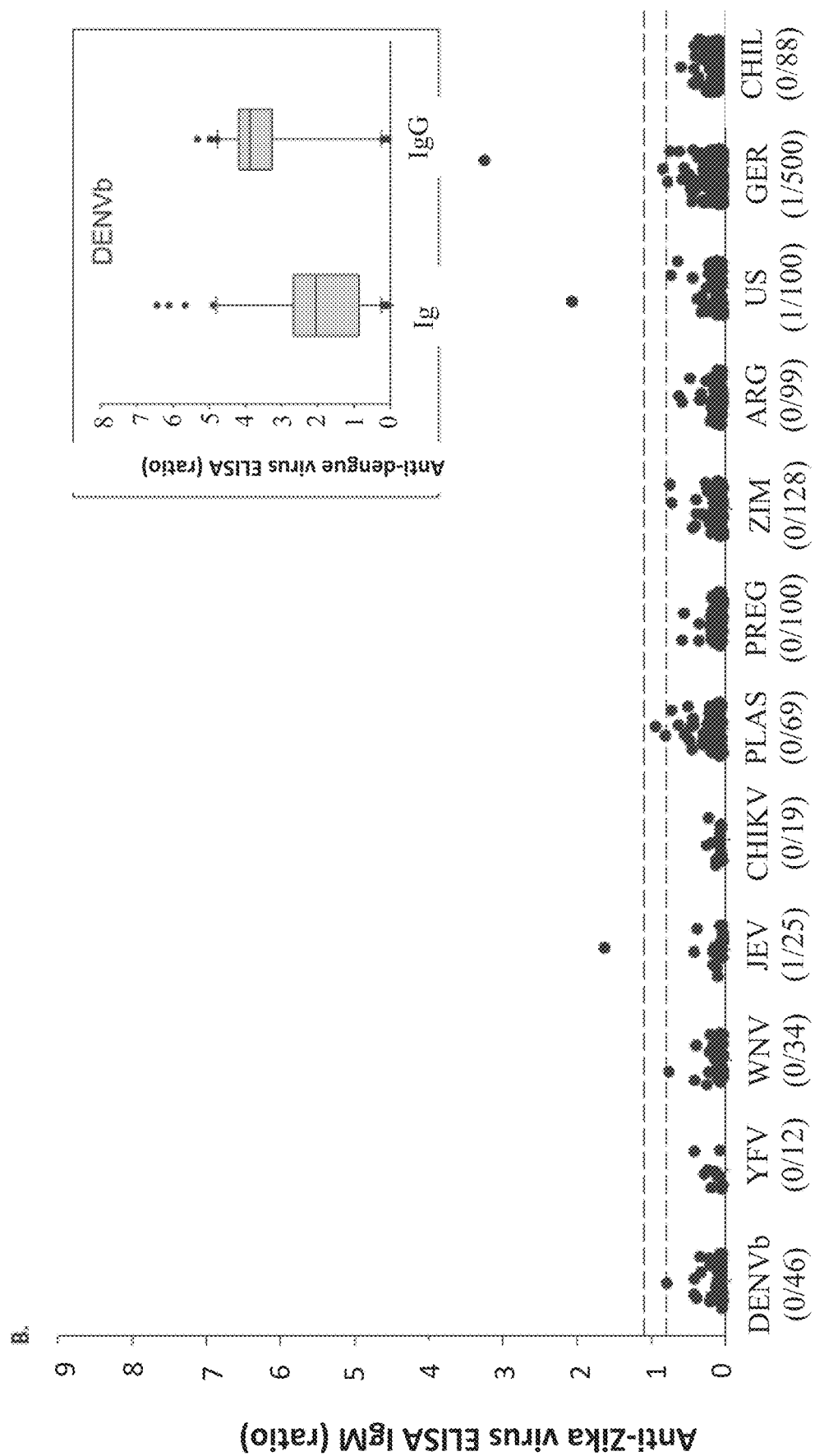

FIG. 10B shows anti-ZIKV reactivity in potentially cross-reactive samples (n=252) and healthy controls (n=1,015) as determined by ELISA for IgG[d,e], study evaluating a novel NS1-based ELISA, Germany 2016

ARG: Argentina; CHIKV: chikungunya virus; CHIL: children; DENV: dengue virus; GER: Germany; JEV: Japanese encephalitis virus; NS: non-structural protein; PLAS: *Plasmodium*; PREG: pregnant women; US: United States; WNV: West Nile virus; YFV: Yellow fever virus; ZIKV: Zika virus; ZIM: Zimbabwe.

[d] Plotted data points represent ratio values (extinction$_{sample}$/extinction$_{calibrator}$); one data point per patient. Cut-off values for borderline results (≥0.8 to <1.1) and positive results (≥1.1) are indicated by horizontal dashed lines. Positive and total cases are indicated in parentheses.

[e] To provide high levels of potentially cross-reactive anti-DENV IgM and IgG antibodies, the DENV-infected patients were divided into two groups: DENVa, high median ratio (3.9) anti-DENV IgM, anti-DENV IgM ratio ≥3.0 in 79% of cases (inset FIG. 10A); DENVb, high median ratio (3.9) anti-DENV IgG, anti-DENV IgG ratio ≥3.0 in 80% of cases (inset FIG. 10B). Cut-off ratio (anti-DENV ELISA, EUROIMMUN): ≥1.1.

Figure 11A:
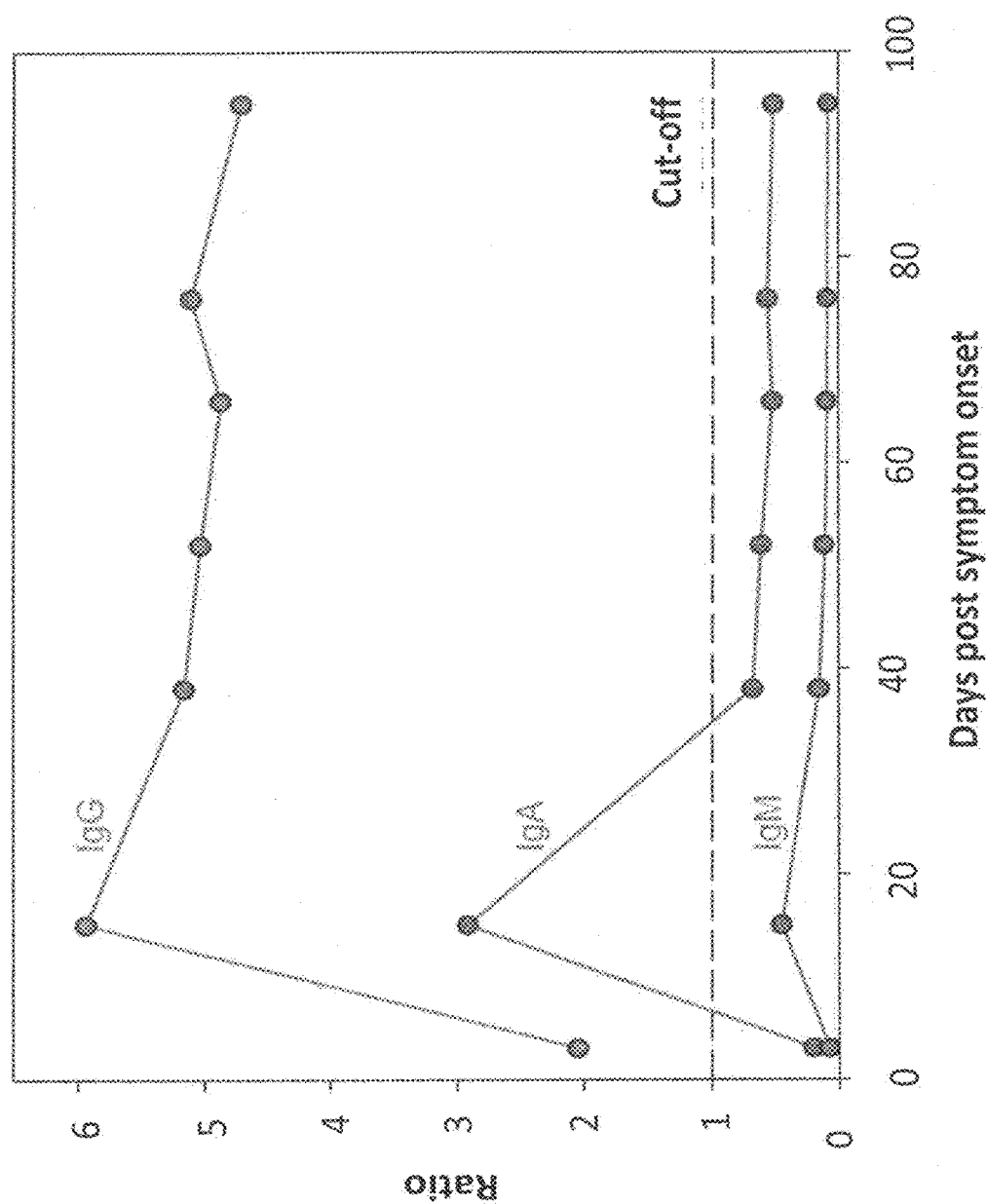

FIG. 11A shows measurements of IgG, IgA and IgM antibodies against ZIKV-NS1 antigen in the sequential samples of one of the two Colombian patients.

Figure 11B:
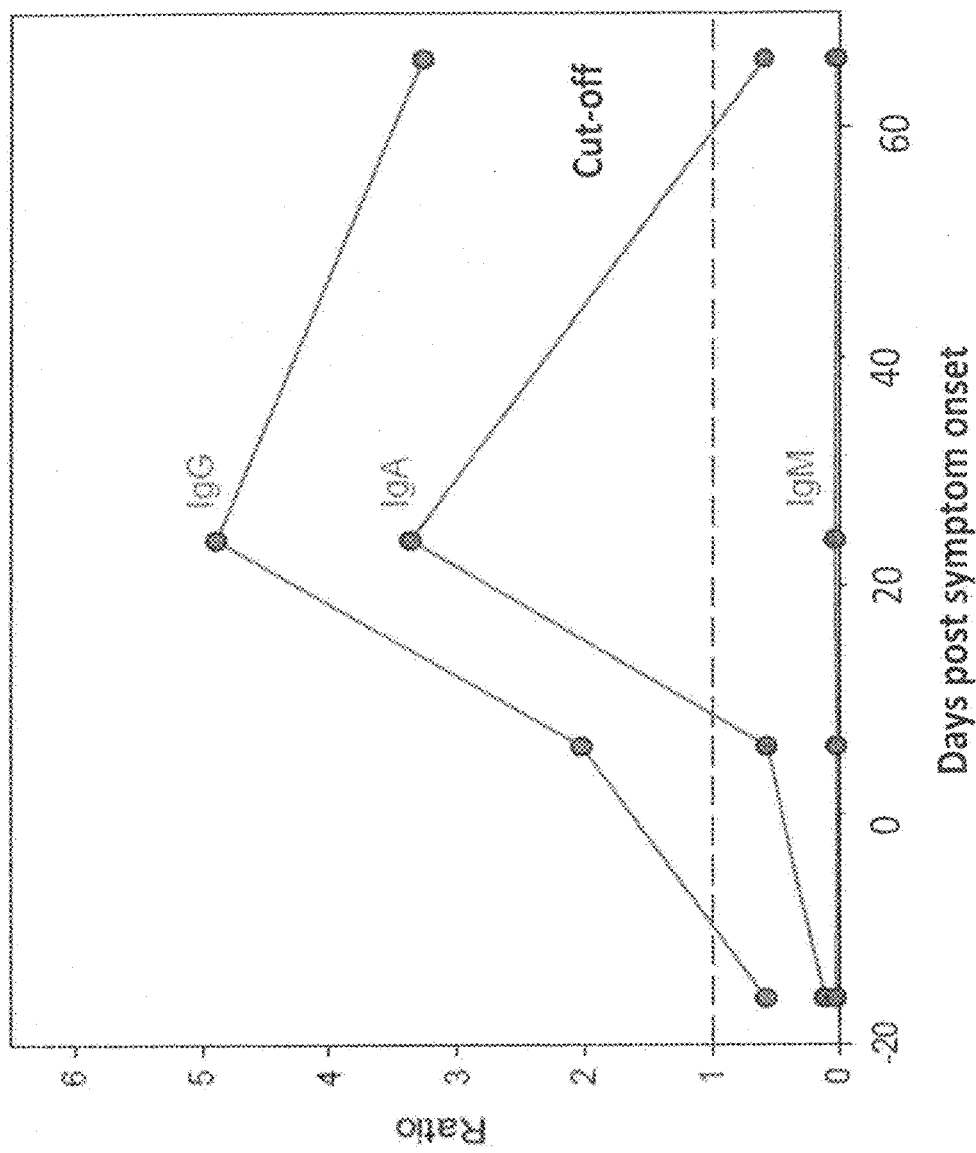

FIG. 11B shows measurements of IgG, IgA and IgM antibodies against ZIKV-NS1 antigen in the sequential samples of one of the two Colombian patients.

Figure 12:
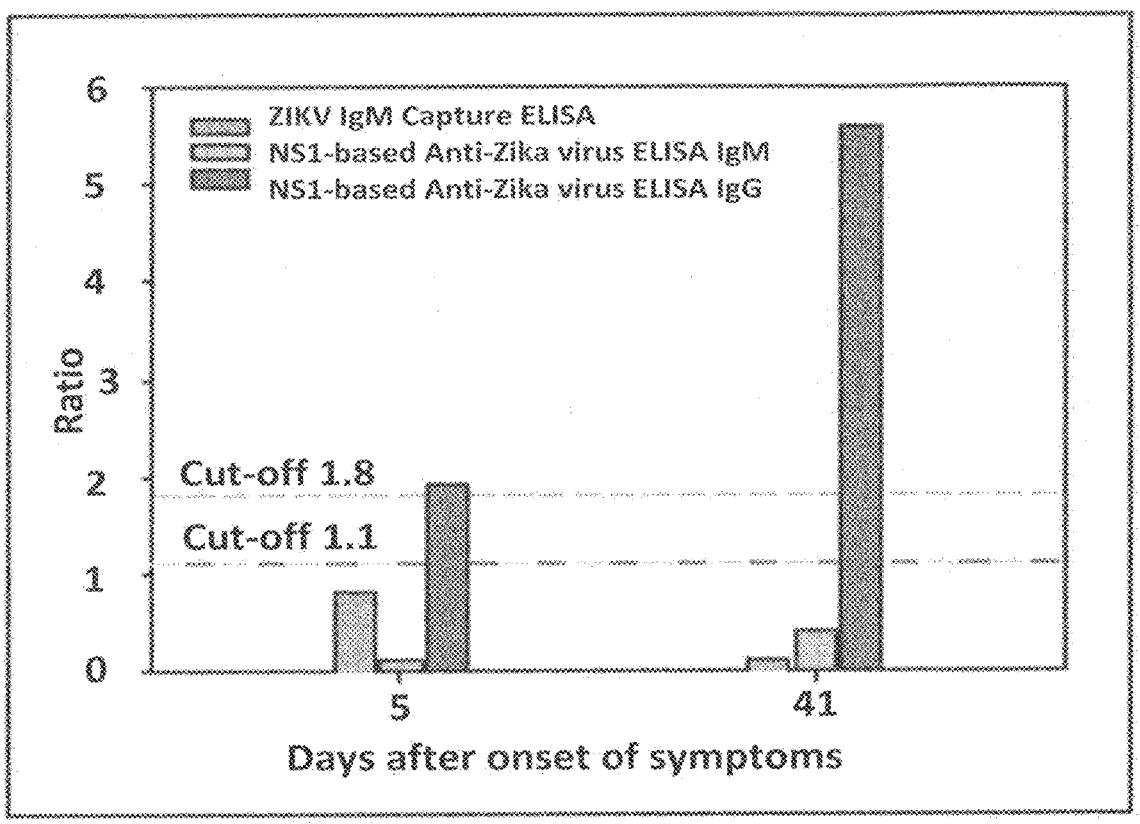

FIG. 12 shows the results of Zika IgM Capture ELISA and NS1-based Anti-Zika virus ELISA IgM and IgG.

DETAILED DESCRIPTION OF THE INVENTION

The present invention sets forth the detection of an antibody to NS1 from Zika virus (SEQ ID NO: 1) as part of a diagnostic method practiced on a sample from a patient suspected of suffering from an infection, preferably a flaviviral infection, more preferably a Zika virus infection.

The present inventors have surprisingly found that a Zika virus infection may be diagnosed and distinguished from other flaviviral infections by detecting antibodies in a sample from a patient, with a surprisingly high degree of diagnostic reliability, in particular relative to the NS1 antigens derived from other flaviviruses, with an unexpected low degree of cross reactivity.

The inventors have also surprisingly found that some patients, despite having been exposed to a Flavivirus, do not have titers of IgM that allow for the monitoring of the course of the infection, but have surprisingly dynamic titers of IgA to NS1 of said Flavivirus that may be used.

More surprisingly, these IgA antibodies do not show a degree of cross reactivity, as would have to be expected, that would make the distinction between an acute Zika virus infection and a previous Flavivirus infection, preferably with a Flavivirus other than the Zika virus, insufficiently reliable.

The inventors have also surprisingly found that Zika virus NS1 antigen exists in oligomeric forms and complexes that have surprising properties relevant for application in diagnostic assays, among them monomers, dimers and hexamers, and complexation with mammalian apolipoproteins, which, when in complex with Zika virus NS1, enhance the diagnostic reliability and stability of the antigen.

The invention relates to a diagnostically useful carrier, which is preferably a solid carrier made from an artificial material such as glass or plastic for contacting a means, which means is associated with said carrier, which means is for specifically capturing an antibody with a bodily fluid sample from a subject, preferably a mammalian subject, more preferably a human subject.

In a preferred embodiment, the term "captured" or "specifically captured", as used herein, means that the binding between the means for specifically capturing and the antibody to be captured is stronger than a binding reaction characterized by a dissociation constant of $1 \times 10^{-5}$ M, more preferably $1 \times 10^{-7}$ M, more preferably $1 \times 10^{-8}$ M, more preferably $1 \times 10^{-9}$ M, more preferably $1 \times 10^{-10}$ M, more preferably $1 \times 10^{-11}$ M, more preferably $1 \times 10^{-12}$ M, as determined by surface plasmon resonance using Biacore equipment at 25° C. in PBS buffer at pH 7. The diagnostically useful carrier may comprise one or more controls, preferably selected from a control confirming that sample has been added and/or a control confirming that a secondary antibody has been added.

In a preferred embodiment, the antibody captured specifically may be an antibody from a certain antibody class, preferably selected from IgG, IgM and IgA, more preferably IgA. In another preferred embodiment, the antibody captured specifically may be an antibody to a Flavivirus antigen, preferably selected from the group comprising NS1 and Envelope glycoprotein, preferably NS1. In a more preferred embodiment, the antibody captured specifically is an IgM or IgA, preferably IgA class antibody to SEQ ID NO: 1, preferably to an epitope from SEQ ID NO: 1 sufficiently long to be recognized by an antibody, which epitope comprises, with reference to SEQ ID NO: 1, one or more amino acids from the group comprising Arg62, Ile66, Arg 69, Glu72, Glycine73, the latter of which may be substituted with serine or alanine, preferably the peptide comprising the sequence Arg 62 to Glycine 73; one or more amino acids from the group comprising Gln102, Pro105, the latter of which could be substituted with a neutral amino acid and a short side chain such as Ser or Ala, and Glu110; preferably the peptide comprising the sequence Gln102 to Glu110; the peptide comprising residues Ser121 to Thr129, the peptide comprising residues Asp138 to Lys141, the peptide comprising residues Asp174 to Glu178 and the peptide comprising Ser322 to Lys326. In a preferred embodiment, the solid carrier is a diagnostic device, more preferably selected from the group comprising a bead, preferably a paramagnetic particle, a test strip, a microtiter plate, blot, a glass surface, a biochip and a membrane, more preferably from the group comprising a bead, a blot, a test strip and a microtiter plate.

The diagnostically useful carrier may be a microtiter plate comprising a range of wells configured for an immunoassays such as an ELISA assay. In a preferred embodiment, the term "microtiter plate" is a diagnostic device, preferably made from glass or plastic, more preferably plastic, comprising one or more, preferably more than one, more preferably at least 8 wells, in which reactions in liquid buffer may be run separately without cross-contamination. At least one of the well is coated with a polypeptide, preferably an antigenic polypeptide that may be used to specifically capture a diagnostically useful antibody. If more than one means for specifically detecting an antigen is used, then preferably each means is in a well separate from other means. The microtiter plate may be used for running several samples in parallel, preferably in an automated fashion. The wells are preferably compatible with at least one routine detection techniques such colorimetry, immunofluorescence, detection of enzymatic activity, chemiluminescence, radioactivity or the like. Suitable microtiter plates are commercially available. If the diagnostically useful carrier is a microtiter plate, it is preferred that at least 50%, 60%, 70%, 80% or 90%, preferably 50% of any Flavivirus NS1, preferably Zika virus NS1, is a hexamer or dimer, preferably dimer.

The diagnostically useful carrier may be a bead configured for an immunoassay comprising a polypeptide comprising SEQ ID NO: 1 or a variant thereof. In a more preferred embodiment, the bead is a paramagnetic microparticle which may be removed from a solution and concentrated, preferably at the surface of a vessel, by applying a magnetic field. The bead comprises an antigen linked to the bead by a covalent or non-covalent bond. If more than one bead is used, a preparation of beads may be made by covalently attaching to the beads a universal ligand which binds strongly to a tag which may be fused to one or more polypeptides according to the present invention by way of genetic engineering. The preparation of beads may then be divided into more than one batches, and each batch is contacted with a different polypeptide fused to a tag to the effect that a range of carriers, each with a different immobilized polypeptide, is produced. A mixture of beads, for example one of which carrying a polypeptide comprising SEQ ID NO: 1 or a variant thereof, and at least one more carrying a polypeptide comprising a sequence selected from the group comprising SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9 may be made. If the diagnostically useful carrier is a bead, it is preferred that at least 50%, 60%, 70%, 80% or 90%, preferably 50% of any Flavivirus NS1, preferably Zika virus NS1, is a monomer, hexamer or dimer, preferably monomer.

The diagnostically useful carrier may be a line blot (Raoult, D., and Dasch, G. A. (1989), The line blot: an immunoassay for monoclonal and other antibodies. Its application to the serotyping of gram-negative bacteria. J. Immunol. Methods, 125 (1-2), 57-65; WO2013041540). In a preferred embodiment, the term "line blot", as used herein, refers to a test strip, more preferably membrane-based, that has been coated with one or more means for capturing an antibody, preferably a polypeptide each. If two or more means are used, they are preferably spatially separated on the carrier. Preferably, the width of the bands is at least 30, more preferably 40, 50, 60, 70 or 80% of the width of the test strip. The test strip may comprise one or more control bands for confirming that it has been contacted with sample sufficiently long and under adequate conditions, in particular in the presence of human serum, antibody conjugate, or both. A multitude of line blots are commercially available, for example from EUROIMMUN AG, Lübeck, Germany. If the diagnostically useful carrier is a line blot, it is preferred that at least 50%, 60%, 70%, 80% or 90%, preferably 50% of any Flavivirus NS1, preferably Zika virus NS1, is a hexamer or dimer, preferably a hexamer.

The diagnostically useful carrier may be a glass slide coated with a cell, preferably a eukaryotic cell, more preferably an insect or mammalian cell, preferably a human cell expressing a Flavivirus NS1, preferably a polypeptide comprising SEQ ID NO: 1. The cell may be a live cell, but is preferably a fixed cell. Immunofluorescence may then be used to detect the antibody. Preferably the cell is a recombinant cell overexpressing the Flavivirus NS1. The Flavivirus NS1 may be localized at a cell membrane, preferably at the surface of the cell. If the diagnostically useful carrier is a glass slide, it is preferred that at least 50%, 60%, 70%, 80% or 90%, preferably 50% of any Flavivirus NS1, preferably Zika virus NS1, is a hexamer or dimer, preferably a dimer.

According to the present invention, the diagnostically useful carrier is configured for capturing an antibody to a Flavivirus antigen. The carrier comprises one or more means for specifically capturing an antibody, preferably one or more, more preferably two or more, more preferably three or more, more preferably four or more such means, each of them capable of specifically capturing a different antibody. Alternatively, one or more carriers, preferably two or more, three or more or four or more, each comprising a means for specifically capturing an antibody, may be used. The means for specifically capturing an antibody may be an antibody binding to all antibodies of a certain Ig glass, preferably selected from the group comprising IgG, IgM and IgA, more preferably IgA class antibodies. Said means is preferably immobilized on said carrier. In a preferred embodiment, the means for specifically capturing an antibody is a polypeptide, preferably a dimer and/or hexamer, more preferably a dimer, comprising or consisting of an antigen from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9 or a variant thereof, preferably SEQ ID NO: 1, SEQ ID NO: 6, SEQ ID NO: 7, SEQ ID NO: 8 and SEQ ID NO: 9 or a variant thereof, and at least one, most preferably one of SEQ ID NO: 2, SEQ ID NO: 3, SEQ ID NO: 4, SEQ ID NO: 5 or a variant thereof. In another preferred embodiment, a polypeptide comprising SEQ ID NO: 1, a polypeptide comprising SEQ ID NO: 6, a polypeptide comprising SEQ ID NO: 7, a polypeptide comprising SEQ ID NO: 8, and at least one polypeptide, preferably all polypeptides, from the group comprising a polypeptide comprising SEQ ID NO 2, a polypeptide comprising SEQ ID NO 3, a polypeptide comprising SEQ ID NO 4 and a polypeptide comprising SEQ ID NO 5 or a variant thereof is used. In another preferred embodiment, a polypeptide comprising SEQ ID NO: 1, a polypeptide comprising SEQ ID NO: 2, a polypeptide comprising SEQ ID NO: 3, a polypeptide comprising SEQ ID NO: 4, a polypeptide comprising SEQ ID NO: 5 and a polypeptide comprising SEQ ID NO: 6 or a variant thereof is used. Preferably at least 0.001, 0.01, 0.05, 0.1, 0.2, 0.5, 1, 5, 10 or 100 µg of polypeptide are used for each carrier as a means for specifically capturing an antibody.

In a preferred embodiment, the diagnostically useful carrier comprises one or more means for specifically capturing an antibody to a Flavivirus envelope glycoprotein, preferably a antigenic polypeptide comprising a sequence selected from the group comprising SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 27 and a variant thereof.

The diagnostically useful carrier may comprise one or more means, each for capturing an antibody to a Flavivirus antigen from the group comprising NS1 of a Flavivirus and Envelope glycoprotein of a Flavivirus, preferably comprising two means for capturing two antibodies, one to NS1 and one to envelope glycoprotein antigens from the same Flavivirus, more preferably one to NS1 from Zika virus and one to the envelope glycoprotein from Zika virus (SEQ ID NO: 1 and SEQ ID NO: 11, respectively).

Said antigen, together with the insoluble carrier to which it is attached, may be separated from a sample from a subject in a straightforward manner, for example by filtration, centrifugation, magnetism or decanting. Said antigen may be immobilized in a reversible or irreversible manner. For example, the immobilization is reversible if the molecule interacts with the carrier via ionic interactions which may be masked by addition of a high concentration of salt or if the molecule is bound via a cleavable covalent bond or a non-covalent bond. By contrast, the immobilization is irreversible if the molecule is tethered to the carrier via a covalent bond that cannot be cleaved in aqueous solution. The polypeptide may be indirectly immobilized, for example by immobilizing an antibody or other entity having affinity to the polypeptide, followed by addition of the polypeptide and formation of a polypeptide-antibody complex. A non-covalent bond may be made by chemically attaching a ligand to the carrier, preferably via a covalent bond, and fusing to the polypeptide according to the present invention a polypeptide having affinity to the ligand. In a preferred embodiment, the ligand is selected from the group comprising biotin, in which case the polypeptide having affinity may be streptavidin or a variant thereof binding to biotin, glutathione (polypeptide having affinity: glutathione-S-transferase), Nickel (polypeptide having affinity: His tag), Flag tag (polypeptide having affinity: anti-flag antibody), carbohydrate such as maltose or cellulose (polypeptide having affinity: maltose or cellulose binding protein), and is preferably biotin.

The polypeptide according to the present invention comprising SEQ ID NO: 1 or a variant thereof or, in addition a polypeptide comprising a sequence selected from the group comprising SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9 and a variant thereof, may be immobilized via the diagnostically relevant antibody to be detected, which is immobilized on the carrier via another antibody directly attached to the carrier. The other antibody may be an Ig class-specific antibody, preferably from the group comprising IgM, IgG and IgA-class specific antibody, more preferably an IgA class specific antibody. The binding site of such a class-specific antibody, which is commercially available, may be the constant region of a human antibody.

The teachings of the present invention may not only be carried out using polypeptides, for example SEQ ID NO: 1, optionally in combination with one or more further antigens such as SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9, having the exact sequences referred to in this application explicitly, for example by function, name, sequence or accession number, or implicitly, but also using variants of such polypeptides.

In a preferred embodiment, the term "variant", as used herein, may refer to at least one fragment of the full length sequence referred to, more specifically one or more amino acid or nucleic acid sequence which is, relative to the full-length sequence, truncated at one or both termini by one or more amino acids. Such a fragment comprises or encodes for a peptide having at least 10, 15, 25, 50, 75, 100, 150, 200, 250 or 300 successive amino acids of the original sequence or a variant thereof. The total length of the variant may be at 25, 30, 40, 50, 60, 70, 80, 90, 100 or more amino acids.

In another preferred embodiment, the term "variant" relates not only to at least one fragment, but also a polypeptide or a fragment thereof comprising amino acid sequences, preferably a fragment comprising at least 25, more preferably 50, more preferably 200, more preferably 300 successive amino acids, that are at least 40, 50, 60, 70, 75, 80, 85, 90, 92, 94, 95, 96, 97, 98 99, 99.4, 99.5, 99.6, 99.7, 99.8 or 99.9% identical to the reference amino acid sequence referred to or the fragment thereof, wherein amino acids other than those essential for the biological activity, for example the ability to bind specifically to an antibody of interest, or the fold or structure of the polypeptide are deleted or substituted and/or one or more such essential amino acids are replaced in a conservative manner and/or amino acids are added or deleted such that the biological activity of the polypeptide is at least partially preserved. Known methods comprise various methods that may be used to align two given nucleic acid or amino acid sequences and to calculate the degree of identity, see for example Arthur Lesk (2008), Introduction to bioinformatics, Oxford University Press, 2008, $3^{rd}$ edition. In a preferred embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007): Clustal W and Clustal X version 2.0. Bioinformatics, 23, 2947-2948) is used applying default settings.

In a preferred embodiment, variants may, in addition, comprise chemical modifications, for example isotopic labels or covalent modifications such as glycosylation, phosphorylation, acetylation, decarboxylation, citrullination, hydroxylation and the like. The person skilled in the art is familiar with methods for the modification of polypeptides. Moreover, variants may also be generated by way of fusion with other known polypeptides or variants thereof.

The variant of the polypeptide has biological activity. In a preferred embodiment, such biological activity is the ability to bind to, preferably capture specifically the respective antibody if the variant is a variant of a sequence from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO 17, SEQ ID NO: 18, SEQ ID NO: 19 and SEQ ID NO: 27, preferably SEQ ID NO: 1. For example, a variant of SEQ ID NO: 1 has the ability to bind specifically to an antibody to SEQ ID NO: 1 in a sample obtained from a subject suspected of suffering from a viral infection. Such variants have at least one epitope recognized by the antibody to be captured, for example one epitope in SEQ ID NO: 1 if an antibody to SEQ ID NO: 1 is captured. The person skilled in the art is capable of designing variants by starting from the original SEQ ID NO: 1 sequence, introducing modifications such as point mutations, truncations and the like and subsequently confirming that the variant still has biological activity by testing whether said variant binds to an antibody to SEQ ID NO: 1 in a sample obtained from a subject suffering from the disease to be diagnosed, preferably an infection, more preferably a viral infection, more preferably an infection with a Flavivirus, most preferably an infection with a Zika virus. The 3D protein structure of the Zika Virus NS1 and related Flaviviruses have been published and may be used for guidance in the design of variants and choice of the sequences that may be varied without compromising the biological activity and to distinguish them from important epitopes (for example Xu et al., Contribution of intertwined loop to membrane association revealed by Zika virus full-length NS1 structure (EMBO J., published on Aug. 30, 2016, open access; Akey et al., Flavivirus NS1 structures reveal surfaces for associations with membranes and the immune system, Science 21; 343(6173):881-5. doi: 10.1126/science; WO2015/095735). For example, with reference to SEQ ID NO: 1, regions that are unique to Zika NS1 and should not be substituted, in particular not in a non-conservative manner, include residues 62 to 73, preferably those comprising Arg62, Ile66, Arg 69, Glu72, Glycine73 (which could be substituted with a neutral amino acid); 102 to 110, preferably Gln102, Pro105 (which could be substituted with a neutral amino acid and a short side chain such as Ser or Ala) and Glu110; residues 121 to 129, residues 138 to 141, 174 to 178 and 322 to 326. The biological activity of mammalian, preferably bovine apolipoprotein provided and used according to the present invention is the ability to bind to and form a complex with a polypeptide comprising Flavivirus NS1, preferably SEQ ID NO: 1. Variants may be identified by identifying naturally occurring fragments of such apolipoproteins derived from the full-length protein or a precursor thereof, for example by purifying them using NS1 as an affinity ligand followed by N-terminal Edman sequencing and/or tryptic digest in combination with mass spectrometry, and using them to practice the invention. Conservative amino acid substitutions may be used for all variants.

If a polypeptide is used as the means for specifically capturing an antibody, said polypeptide, preferably comprising one or more sequences selected from the group comprising SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 19, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO 17, SEQ ID NO: 18, SEQ ID NO: 19 and SEQ ID NO: 27, preferably SEQ ID NO: 1, when used to carry out the teachings of the present invention, may be provided in any form and at any degree of purification, from tissues or cells comprising said polypeptide in an endogenous form, more preferably cells overexpressing the polypeptide, crude or enriched lysates of such cells, to purified and/or isolated polypeptide which may be essentially pure. In a preferred embodiment, the term "overexpressing", as used herein, means that the cell, preferably a eukaryotic, more preferably a mammalian or insect, more preferably a mammalian, more preferably a human cell, most preferably a HEK293 or HEK293T cell, has been genetically engineered such that it expresses more of the protein of interest than a non-engineered wild type cell would. In a preferred embodiment, the polypeptide is a native polypeptide, wherein the term "native polypeptide", as used herein, refers to a folded polypeptide comprising at least 15, 30, 50, 100 150, 200, 300 or 350 amino acids, preferably more than 30 amino acids, more preferably to a folded polypeptide purified from tissues or cells, more preferably from mammalian cells or tissues, optionally from non-recombinant tissues or cell. In another preferred embodiment, the polypeptide is a linear peptide having at least 7, more preferably at least 10 amino acid residues. If a native polypeptide is used, it is preferably enriched compared to its natural state. A recombinant polypeptide may comprise a C-terminal or N-terminal tag for affinity purification, immobilization or detection such as a His tag, as exemplified by SEQ ID NO: 10, or a streptavidin tag, preferably a streptavidin, which tag may preferably be removed by cleavage using a protease recognizing a protease cleavage site in a polypeptide linker between the tag and the N terminus or C-terminus, respectively, as part of the purification or method. The cleaved polypeptide may subsequently be attached to a diagnostically useful carrier to yield the diagnostically useful carrier according to the present invention. In another preferred embodiment, the means for specifically capturing an antibody is a Zika virus-infected eukaryotic, preferably human cell. Such a cell may be evaluated by fluorescence microscopy. The cells may be transiently or stably transfected, preferably transiently transfected.

According to the present invention, a nucleic acid encoding the polypeptide according to the present invention such as a polypeptide comprising SEQ ID NO: 1 or a variant thereof, optionally with an inducible promotor, which polypeptide is preferably for use for the diagnosis of a disease or the manufacture of a kit or reagent for such use, is provided. Said nucleic acid may be a vector, preferably for expressing said nucleic acid. A eukaryotic or prokaryotic, preferably eukaryotic cell comprising this vector and preferably expressing the polypeptide encoding by the vector, is also provided. The nucleic acid, the vector and the cell may be used for the manufacture of a kit for use according to the present invention such as use of an antibody to NS1, preferably IgA class antibody to NS1 from a Flavivirus, preferably the Zika virus, or a diagnostically useful carrier for immobilizing and optionally detecting said antibody, for distinguishing a primary from a secondary, preferably the Zika virus infection use of an IgA class antibody to NS1 from a Flavivirus, preferably the Zika virus, or a diagnostically useful carrier for immobilizing and optionally detecting said antibody, for diagnosing a flaviviral infection, preferably a Zika virus infection, in an IgM-deficient subject, such as use of an IgA class antibody to NS1 from a Flavivirus, preferably the Zika virus, or a diagnostically useful carrier for immobilizing and optionally detecting said antibody, for increasing the diagnostic reliability, preferably sensitivity, of a diagnostic assay for diagnosing a flaviviral infection, preferably a Zika infection, more preferably at the early stages of an infection or such as for distinguishing a primary from a secondary, preferably the Zika virus infection or such as for increasing the diagnostic reliability, preferably sensitivity, of a diagnostic assay for diagnosing a flaviviral infection, preferably a Zika infection, more preferably at the early stages of an infection. The nucleic acid may be expressed, the polypeptide encoded purified and used, preferably coated on a diagnostically useful carrier, in order to make the diagnostically useful carrier according to the present invention. In a preferred embodiment, the term "early stage" refers to the time period before the first 60, preferably first 40 days after symptom onset, wherein more preferably no increase in IgG class antibodies can be observed.

A polypeptide provided or used in a method or as part of a carrier or used in any other way according to the present invention may be glycosylated or non-glycosylated, preferably glycosylated. A glycosylated polypeptide comprising SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 19 or SEQ ID NO: 9 or a variant thereof may be obtained by purifying the polypeptide from a eukaryotic cell, preferably a HEK293 or HEK293T cell. A homogenously glycosylated polypeptide may be obtained by purifying the polypeptide from the cytosolic fraction of a eukaryotic cell, a heterogeneously glycosylated polypeptide may be obtained by purifying the polypeptide from the cell culture supernatant medium following culture of a eukaryotic cells expressing the polypeptide. A non-glycosylated polypeptide may be obtained by enzymatic deglycosylation of a polypeptide purified from a eukaryotic cell or by purification of a polypeptide expressed in a prokaryotic cell.

In a preferred embodiment, a polypeptide comprising a sequence from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9 or a variant thereof, preferably SEQ ID NO: 1 or a variant thereof, may be provided or used, as part of a diagnostically useful carrier, method or use according to the present invention in various oligomeric forms that comprise one or more than one monomer, for example 2, 3, 4, 5, 6, 7, 8, 9, 10, 11 or 12 monomers, and may be used, for example, as a means for capturing an antibody to Flavivirus N1, preferably comprising SEQ ID NO: 1 or a variant thereof, optionally an IgA class antibody to a Flavivirus NS1, in the form of a monomer, dimer or a hexamer, preferably a dimer. In a preferred embodiment said monomer, dimer or hexamer, preferably dimer, has been purified from a eukaryotic cell, preferably recombinant eukaryotic cell, such as a HEK293T or HEK293 cell, preferably from the cytoplasmic fraction, which contains the dimeric form, or the cell medium in which the cell was grown, which contains the hexameric form secreted into the medium, preferably from the cytosolic fraction. In another preferred embodiment, a mixture of oligomeric forms, preferably purified from a eukaryotic cell, is used, wherein the molar ratio of dimer to hexamer is at least 0.1:1, preferably, 0.5:1, 1:1, 1.5:1, 2:1, 5:1 or 10:1. In another preferred embodiment, a mixture of oligomeric forms, preferably purified from a eukaryotic cell, is used, wherein the molar ratio of hexamer to dimer is at least 0.1:1, preferably, 0.5:1, 1:1, 1.5:1, 2:1, 5:1 or 10:1. In a preferred embodiment, the hexamer is used as a means to capture an IgG class. In another preferred embodiment, the dimer is used to capture an IgM class antibody.

Alternatively, a prokaryotic cell or chemical synthesis may be used to express or obtain and to purify the polypeptide oligomer, preferably dimer or hexamer, optionally by chemical crosslinking and isolating the oligomer, preferably dimer or hexamer. The person skilled in the art is familiar with techniques for isolating or enriching certain oligomeric forms, for example using size-exclusion chromatography. The interface of the monomers in an oligomeric form, which causes the monomers to associate to the oligomer, is preferably made of SEQ ID NO: 1 or a variant thereof that is part of sequence of the monomers in the oligomeric form.

An oligomer comprising more than one monomer may be stabilized by a non-covalent or covalent bond, preferably covalent bond between the two or more monomers that form such oligomer. In a preferred embodiment, the oligomer is stabilized by one or more covalent bond via one or more Cysteine side chains between the monomers. The covalent bond may be a disulfide bond or comprise a linker comprising two functional groups that are reactive with thiol groups, which linker links two side chain residues following reaction of the two functional groups with two thiol groups. In a more preferred embodiment, this covalent bond is between two cysteine residues side chain that would not normally form a disulfide bond in the native, as mentioned in (Xu et al., (Contribution of intertwined loop to membrane association revealed by Zika virus full-length NS1 structure (EMBO J., published on Aug. 30, 2016, open access), natural state of the protein. In another preferred embodiment, the oligomer is stabilized by non-covalent bonds between monomers, and at least 1, 2, 3, 4, 5, 6, 7, 8, 9, 10 11 or 12 cysteine residues are oxidized, forming intermonomeric disulfide bonds.

In a preferred embodiment, the Flavivirus NS1, preferably SEQ ID NO: 1 or a variant thereof, is in complex with a lipid, which lipid is preferably derived from a cell membrane, more preferably from a Eukaryotic cell membrane such as a HEK293 cell membrane.

Oligomeric forms such as dimers or hexamers may be used, when practicing the present invention, in the form of homogenous or heterogeneous oligomers, wherein homogeneous oligomers comprise two or more different monomers, optionally derived from different flavivirus sequences from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9 or a variant thereof, preferably of SEQ ID NO: 1 or a variant thereof. For example, a heterogeneous dimer may comprise a monomer comprising SEQ ID NO: 1 and a monomer comprising SEQ ID NO: 2. By contrast, heterogeneous oligomers comprise two monomers which are both derived from the same sequence from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9 or a variant thereof, preferably of SEQ ID NO: 1 or a variant thereof, and are optionally identical.

In a preferred embodiment, the antibody to be detected may be an antibody to a monomer, dimer and/or hexamer, preferably to a dimer, of a polypeptide from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9 or a variant thereof, preferably SEQ ID1 or a variant thereof. Said antibody or an antibody binding to a polypeptide from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9 or a variant thereof, preferably SEQ ID1 or a variant thereof regardless of the oligomeric state, may be provided as an isolated and/or recombinant antibody or antibody fragment.

In another preferred embodiment, the polypeptide comprising a sequence from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9 and a variant thereof, preferably SEQ ID1 or a variant thereof, preferably a dimer and/or hexamer, preferably the hexamer, is used in a mixture with a mammalian, preferably non-human polypeptide such as a bovine polypeptide such as mammalian Apolipoprotein A-I, more preferably human (NCBI Reference Sequence: NP_000030.1) or bovine Apolipoprotein A-I (GenBank: AAI02942.1; all data base codes cited in this document refer to the entry in the respective data base at the date of priority), or human (NCBI: NP_000375.2) or bovine Apolipoprotein B-100 isoform X1 (NCBI: XP_015329038.1 or a variant thereof) most preferably bovine Apolipoprotein A-I or a variant thereof. The mixture may comprise a complex of the polypeptide comprising a sequence from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9 and a variant thereof, preferably SEQ ID NO: 1 or a variant thereof, preferably a dimer and/or hexamer, preferably the hexamer, and, as a second component of the complex, a mammalian Apolipoprotein A-I, more preferably human (NCBI Reference Sequence: NP_000030.1) or bovine Apolipoprotein A-I (GenBank: AAI02942.1), most preferably bovine Apolipoprotein A-I or a variant thereof, which complex may be used for practicing the invention, for example for the diagnosis of a disease, more specifically as a means for capturing an antibody. In the mixture, preferably the complex, the molar ratio between polypeptide monomers and the mammalian Apolipoprotein A-1 may be at least 1:1, 2:1, 5:1, 6:1, 10:1, 50:1 or 100:1.

According to the present invention, the polypeptide may be a recombinant protein, wherein the term "recombinant", as used herein, refers to a polypeptide produced using genetic engineering approaches at any stage of the production process, for example by fusing a nucleic acid encoding the polypeptide to a strong promoter for overexpression in cells or tissues or by engineering the sequence of the polypeptide itself. The person skilled in the art is familiar with methods for engineering nucleic acids and polypeptides encoded (for example, described in Sambrook, J., Fritsch, E. F. and Maniatis, T. (1989), Molecular Cloning, CSH or in Brown T. A. (1986), Gene Cloning—an introduction, Chapman & Hall) and for producing and purifying native or recombinant polypeptides (for example Handbooks "Strategies for Protein Purification", "Antibody Purification", published by GE Healthcare Life Sciences, and in Burgess, R. R., Deutscher, M. P. (2009): Guide to Protein Purification). In another preferred embodiment, the polypeptide according to the present invention and used for the various embodiments of the present invention is an isolated polypeptide, wherein the term "isolated", as used herein, means that the polypeptide has been enriched compared to its state upon production using a biotechnological or synthetic approach and is preferably pure, i.e. at least 10, 20, 30, 40, 50, 60, 70, 80, 90, 95 or 99 percent of the polypeptide in the respective sample consists of said polypeptide as judged by SDS polyacrylamide gel electrophoresis followed by Coomassie blue staining and visual inspection.

The subject according to the present invention is an organism producing antibodies, preferably IgA, IgM and/or IgG class antibodies, more preferably from a mammal, most preferably a human. According to the present invention, IgM and IgG class antibodies to SEQ ID NO: 1 may be detected in separate assay reactions, for example to determine the time when the subject was infected for the first time.

Within the scope of the present invention is a diagnostically useful carrier comprising a means for specifically capturing an antibody to an antigen such as SEQ ID NO: 1. In a preferred embodiment, the term "specifically capturing an antibody", as used herein, refers to the ability to bind specifically to the antibody of interest, preferably an IgA, IgM or IgG class antibody, to the effect that it is bound and removed from the sample, whereas other antibodies, preferably from the same class and/or to another antigen, are essentially not bound and remain in the sample. The antibody is preferably an antibody that binds to the antigen of interest only such as the one represented by SEQ ID NO: 1, but not to other homologous antigens from other viruses such as those represented by SEQ ID NO: 1, SEQ ID NO:

2, SEQ ID NO: 3, SEQ ID NO: 4, SEQ ID NO: 5, SEQ ID NO: 6, SEQ ID NO: 7, SEQ ID NO: 8 and SEQ ID NO: 9.

The diagnostically useful carrier according to the invention serves as a scaffold for the one or more means for specifically capturing an antibody, preferably a diagnostically relevant antibody to a Flavivirus antigen such as the one represented by SEQ ID NO: 1. Said carrier is suitable for carrying out a diagnostic method. By using a carrier rather than free, soluble means for specifically capturing an antibody, it is more straightforward to isolate and separate from the sample a complex comprising the means and the antibody and to wash said complex, for example for the purpose of removing any molecules binding non-specifically to the means, complex or carrier. In a preferred embodiment, the diagnostically useful carrier is a diagnostic device, preferably selected from the group comprising a bead, preferably a paramagnetic particle, a test strip, a microtiter plate, a blot and a membrane, and is preferably a line blot or microtiter plate, more preferably a microtiter plate.

In a preferred embodiment, the diagnostically useful device is a microtiter plate comprising a well coated with a means for specifically capturing an antibody to SEQ ID NO: 1, which means is preferably a polypeptide comprising SEQ ID NO: 1 or a variant thereof. In addition, said well comprises a means for detecting an antibody to at least one of SEQ ID NO: 2, SEQ ID NO: 3, SEQ ID NO: 4 and SEQ ID NO: 5, preferably all of them, preferably a polypeptide comprising at least one of SEQ ID NO: 2, SEQ ID NO: 3, SEQ ID NO: 4 and SEQ ID NO: 5 or a variant thereof. In addition, said well comprises means for specifically capturing an antibody to each of SEQ ID NO: 6, SEQ ID NO 7, SEQ ID NO: 8 and SEQ ID NO: 9, preferably a polypeptide comprising SEQ ID NO: 6 or a variant thereof, SEQ ID NO 7 or a variant thereof, SEQ ID NO 8 or a variant thereof and SEQ ID NO: 9 or a variant thereof. In addition, a separate well may include one or more antigens for detecting a chikungunya virus infection.

In a preferred embodiment, the term "specifically detecting a captured antibody", as used herein, means that the antibody binding specifically to the means for specifically capturing the antibody, preferably a polypeptide comprising SEQ ID NO: 1 or a variant thereof, following capture, is detected rather than any other antibody present in the sample. In a preferred embodiment, the term "binding specifically", as used herein, means that the binding is stronger than a binding reaction characterized by a dissociation constant of $1\times10^{-5}$ M, more preferably $1\times10^{-7}$ M, more preferably $1\times10^{-8}$ M, more preferably $1\times10^{-9}$ M, more preferably $1\times10^{-10}$ M, more preferably $1\times10^{-11}$ M, more preferably $1\times10^{-12}$ M, as determined by surface plasmon resonance using Biacore equipment at 25° C. in PBS buffer at pH 7.

In a preferred embodiment, the means for specifically capturing an antibody to SEQ ID NO 1 and the means for specifically capturing an antibody to one or more further antigens, preferably selected from the group comprising SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9, are on separate carriers. This means that the means are not attached to a single carrier, but one or more carriers that are separate and/or separable without damaging them. For example, the means for specifically capturing an antibody to SEQ ID NO 1 may be attached to a first test strip, and the means for specifically capturing an antibody to SEQ ID NO 2 is attached to another test strip which is separate from the first test strip.

In a preferred embodiment, the means for specifically capturing an antibody to SEQ ID NO 1 and the means for specifically capturing an antibody to one or more further antigens, preferably selected from the group comprising SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9, are on one, preferably covalently linked to one carrier. This means that the means are attached to one carrier which may not be disassembled, without damaging the carrier, such that the means are on separate carriers. For example, the means may be all coated on one test strip, particular in the form of a line blot.

According to the present invention, a means for specifically detecting a captured antibody is provided, optionally as part of a kit.

The inventive teachings provide a kit, preferably for diagnosing an infection, more preferably for diagnosing a flavivirus infection, most preferably a Zika virus infection. Such a kit is a container that comprises specific reagents required to practice the inventive method, in particular the diagnostically useful carrier according to the present invention, optionally in addition to one or more solutions required to practice the inventive method, preferably selected from or all from the group comprising sample dilution buffer, washing buffer and buffer comprising a means for detecting any specifically captured antibody, such as a secondary antibody and optionally a means for detecting the specifically captured antibody, which may optionally be attached to the secondary antibody, for example a fluorescent, enzymatically active, radioactive, chemiluminescent, preferably electrochemiluminescent label or a spin label. The kit may comprise a chemical solution for carrying out a detection reaction such as 3,3',5,5'-tetramethylbenzidine, p-Nitrophenyl Phosphate, 2,2'-Azinobis [3-ethylbenzothiazoline-6-sulfonic acid or o-phenylenediamine dihydrochloride for a colorimetric reaction tripropylamine for an electrochemiluminescence reaction. Furthermore, it may comprise instructions detailing how to use the kit and the inventive diagnostically useful carrier for contacting the inventive polypeptide with a bodily fluid sample from a subject, preferably a human subject, for example a line blot, wherein the inventive means for specifically capturing SEQ ID NO: 1, preferably a polypeptide comprising SEQ ID NO: 1 or a variant thereof, is immobilized on the line blot. Furthermore, the kit may comprise a positive control, for example a recombinant antibody known to bind to SEQ ID NO: 1, and a negative control, for example a protein having no detectable affinity to SEQ ID NO: 1. Finally, the kit may comprise a standard solution comprising a SEQ ID NO: 1-binding antibody for preparing a calibration curve. In a preferred embodiment, the kit comprises a device, preferably a blot-based device such as a line blot coated with a means for specifically capturing an antibody to SEQ ID NO: 1 and, optionally, an antibody to one or more further antigens such as SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and/or SEQ ID NO: 9. The kit may comprise one or more further control selected from a control confirming that sample has been added and/or a control confirming that a secondary antibody has been added.

According to the invention, a means for detecting the one or more captured antibodies may be used. The person skilled in the art is aware of many methods that may be used, which are also described in the state of the art, for example in Zane, H. D. (2001), Immunology—Theoretical & Practical Concepts in Laboratory Medicine, W. B. Saunders Company, in particular in Chapter 14. In a preferred embodiment, a secondary antibody binding to the constant region of the one or more captured antibodies, which is the corresponding primary antibody, is used, which secondary antibody may be associated with a label that is straightforward to detect. Alternatively, an antigenic polypeptide, preferably from the group of polypeptides comprising a sequence from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and SEQ ID NO: 9 and a variant thereof, preferably SEQ ID NO: 1, or a variant thereof may be used to detect the diagnostically relevant antibody, preferably following its immobilization, wherein said polypeptide preferably comprises a label that is straightforward to detect. Such antigenic polypeptide may bind to any immobilized diagnostically useful antibody to allow the specific detection. The label that is straightforward to detect may be selected from the group comprising label that is straightforward to detect, for example a fluorescent, chemiluminescent such as electrochemiluminescent, radioactive label, spin label or enzymatically active label, the latter of which may catalyze a chemiluminescent reaction, or it may bring about the generation of a molecule detectable or a signal such as a photon using colorimetry, fluorescence detection such as fluorescence microscopy, photomultiplication or spectroscopy or another analytical method.

In a preferred embodiment, the term "diagnosis", as used herein, refers to any kind of procedure aiming to obtain information instrumental in the assessment whether a patient suffers or is likely or more likely than the average or a comparative subject, the latter preferably having similar symptoms, to suffer from a certain disease or disorder in the past, at the time of the diagnosis or in the future, to find out how the disease is progressing or is likely to progress in the future or to evaluate the responsiveness of a patient with regard to a certain treatment, for example the administration of suitable drugs such as drugs for the desensitization of allergic patients. In other words, the term "diagnosis" comprises not only diagnosing, but also prognosticating and/or monitoring the course of a disease or disorder.

Therefore, the term "diagnosis" does preferably not imply that the diagnostic methods or agents according to the present invention will be definitive and sufficient to finalize the diagnosis on the basis of a single test, let alone parameter, but may refer to a contribution to what is referred to as a "differential diagnosis", i.e. a systematic diagnostic procedure considering the likelihood of a range of possible conditions on the basis of a range of diagnostic parameters. The term "diagnosis" may also refer to a method or agent used to choose the most promising treatment regime for a patient. In other words, the method or agent may relate to selecting a treatment regimen for a subject.

The present invention relates to a method comprising the step detecting in a sample from a subject the presence or absence of an antibody to an antigenic polypeptide such as a polypeptide comprising a SEQ ID NO: 1 or a variant thereof. This method preferably comprises immobilizing said antibody followed by specific detection of said antibody, for example by way of the steps a) providing a sample from a subject, b) contacting the sample with the diagnostically useful carrier according to the present invention under conditions compatible with the formation of a complex comprising the diagnostically useful carrier and the antibody, more specifically the means for specifically capturing the antibody and the antibody, c) isolating any said complex, for example by removing the sample, d) optionally washing said complex, and e) optionally detecting said complex. The method is preferably an in vitro method. The detection of the complex for the prognosis, diagnosis, methods or test kit according to the present invention comprises the use of a method selected from the group comprising immunodiffusion techniques, immunoelectrophoretic techniques, light scattering immunoassays, agglutination techniques, labeled immunoassays such as those from the group comprising radiolabeled immunoassay, enzyme immunoassays such as colorimetric assays, chemiluminescence, preferably electrochemiluminescence, immunoassays and immunofluorescence techniques. The person skilled in the art is familiar with these methods, which are also described in the state of the art, for example in Zane, H. D. (2001): Immunology—Theoretical & Practical Concepts in Laboratory Medicine, W. B. Saunders Company, in particular in Chapter 14. The method may further involve testing the avidity of antibodies to SEQ ID NO: 1 in the sample, preferably of antibodies to SEQ ID NO: 1.

A product obtained when practicing the inventive method is a diagnostically useful carrier comprising a means for specifically detecting an antibody to SEQ ID NO: 1 in complex with the antibody to SEQ ID NO: 1 and optionally a means for specifically detecting the antibody to SEQ ID NO: 1 such as a secondary antibody. If the antibody to SEQ ID NO: 1 is an IgM class antibody, the secondary antibody is a labeled antibody binding to a constant region of IgM class antibodies. If the antibody to SEQ ID NO: 1 is an IgG class antibody, the secondary antibody is a labeled antibody binding to a constant region of IgG class antibodies. If the antibody to SEQ ID NO: 1 is an IgA class antibody, the secondary antibody is a labeled antibody binding to a constant region of IgA class antibodies. The diagnostically useful carrier may be a microtiter plate with one or more than one wells, one well comprising a means for specifically capturing an antibody to SEQ ID NO: 1, and at least one or more, two or more, three or more, for or more wells each comprising a means for specifically capturing an antibody to a sequence from the group comprising SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and/or SEQ ID NO: 9.

In many cases, detecting the absence or presence of an antibody, optionally meaning determining whether the concentration of the antibody is beyond a certain threshold, often suggested by the detection limit, in the sample, is sufficient for the diagnosis. If the antibody can be detected, this could be information used for clinician's diagnosis and indicates an increased likelihood that the patient suffers from a disease. In a preferred embodiment, the relative concentration of the antibody in serum, compared to the level that may be found in an average healthy subject, may be determined. In a preferred embodiment, the term "detecting the presence or absence", as used herein, means that it is sufficient to check whether a signal sufficiently beyond any background level may be detected using a suitable complex detection method that indicates that the antibody of interest is present or more antibody of interest is present than would be in a healthy subject. In a more preferred embodiment, this may involve determining whether the concentration is at least 0.1, preferably 0.2, 0.5, 1, 2, 5, 10, 20, 25, 50, 100, 200, 500, 1000, 10000 or 100000 times higher than the concentration of the antibody of interest found in the average healthy subject.

The disease to be diagnosed is an infection, preferably a viral, more preferably Flavivirus, most preferably Zika virus infection. Preferably, a Zika virus infection may be distinguished from another Flavivirus infection, more preferably from an infection with a Flavivirus selected from the group comprising dengue virus, Yellow fever virus, Tick-borne encephalitis virus, Usutu virus, West Nile virus and Japanese encephalitis virus or all of them, preferably from the dengue virus.

The invention may be used to provide a prognosis whether a pregnant woman's newborn child is likely to suffer from a deformity if the sample from the pregnant woman is tested. Preferably, the pregnant woman may have symptoms suggesting that she may suffer from a flaviviral infection or may very actually suffer from an infection.

The invention may be used to diagnose whether deformities in a child, such as microcephaly, are a result of a previous Zika virus infection or not.

The invention may be used to diagnose whether a subject is suffering or likely to suffer, following onset of the infection, from an autoimmune disease such as the Guillan Barré syndrome. More specifically, if antibodies to SEQ ID NO: 1 are detected in a sample from a subject, said subject is more likely to suffer from an autoimmune disease than a subject having no antibodies to SEQ ID NO: 1.

The invention may be used to test samples comprising autoimmune antibodies such as ANA autoantibodies which may obscure results obtained using conventional assays and so may be used in combination with a method comprising the step detecting in a sample from a subject ANA autoantibodies. Commercially available kits may be used for detecting ANAs for example EUROPLUS ANA Mosaic 20A, ANA screen 11, ANA Profile 3 or Anti-ENA Profile-Plus. This may allow distinguishing an autoimmune disease from a viral infection or an antibody relating to an autoimmune disease and those relating to a viral infection.

The invention may be used to distinguish Flavivirus infections from other viral infections, preferably alphavirus infections, more preferably a chikungunya virus infection.

The invention may be used to screen blood given by blood donors for previous infections.

In a preferred embodiment, the absence or presence of one or more antibodies, such as an antibody to SEQ ID NO: 1, is detected simultaneously, i.e. at the same time. This is convenient in terms of efficient diagnostic procedures, as a maximum of diagnostic information is obtained in a given period of time. Of course, a prerequisite is that sufficient capacity is available for running all reactions.

In a preferred embodiment, the absence or presence of at least two antibodies, such as an antibody to SEQ ID NO: 1 and one and more antibodies to an antigen from the group comprising SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 27, is detected in spatially separate reactions. This means that these reactions run in different reaction mixtures in separate vessels, for example separate wells of a microtiter plate or separate compartments each comprising a different bead or the same compartment used subsequently with more than one bead.

If more than one antibody is to be detected, the method may, in another preferred embodiment, be carried out in a one-pot reaction. Preferably, the term "one-pot reaction", as used herein, means that two or more, preferably all reactions carried out for the purpose of detecting the presence or absence of an antibody are carried out in the same reaction mixture in one reaction vessel, without physical barriers between the reactions, by contrast to experimental settings contemplating that at least two reactions are carried out in separate solutions and reaction vessels.

The invention provides a pharmaceutical composition or a vaccine, which composition or immunogenic composition such as a vaccine comprises a polypeptide comprising SEQ ID NO: 1 or a variant thereof, optionally in combination with one or more further antigens such as one or more selected from the group comprising SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 19 and/or SEQ ID NO: 9, preferably in addition to previously used antigens such as an Zika virus Envelope glycoprotein, preferably comprising the sequence AHL16749.1 (UNIPROT data base as online on priority date) or a variant thereof or SEQ ID NO 11, preferably SEQ ID NO 11 or a variant thereof, and/or a Zika virus. Moreover, the composition or immunogenic composition may comprise an antigen comprising a sequence selected from the group comprising SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 27 and a variant thereof or a variant thereof. An immunogenic composition or vaccine may comprise components to inactivate a virus or bacteria and stabilize the vaccine, helping to preserve the vaccine and prevent it from losing its potency overtime. Adjuvants are added to vaccines to simulate the production of antibodies against the vaccine to make it more effective. An adjuvant could be organic or inorganic. The most common inorganic adjuvants for human vaccines include aluminum phosphate and aluminum hydroxide. Organic adjuvants could be based on the organic compound squalene and an oil [squalene] in water adjuvant can be used. An immunogenic composition may comprise stabilizers that help the vaccine to maintain its effectiveness during storage, e.g., $MgCl_2$, $MgSO_4$, lactose-sorbitol, or sorbitol-gelatin, and preservatives to prevent bacterial and fungal growth, e.g., thiomersal, formaldehyde, or phenol derivatives, antibiotics. The composition is preferably suitable for administration to a subject, preferably a mammalian subject, more preferably to a human. Such a pharmaceutical composition may comprise a pharmaceutically acceptable carrier. The pharmaceutical composition may, for example, be administered orally, parenterally, by inhalation spray, topically, by eyedrops, rectally, nasally, buccally, vaginally or via an implanted reservoir, wherein the term "parentally", as used herein, comprises subcutaneous, intracutaneous, intravenous, intramuscular, intra-articular, intrasynovial, instrasternal, intrathecal, intralesional and intracranial injection or infusion techniques. The pharmaceutical composition may be provided in suitable dosage forms, for example capsules, tablets and aqueous suspensions and solutions, preferably in sterile form. It may be used in a method of treatment of a disease, which method comprises administering an effective amount of the inventive polypeptide to a subject.

The inventive method for diagnosing a Flavivirus infection, preferably for distinguishing a primary from a secondary Flavivirus infection, may comprise the step detecting in a first sample from a subject an IgA class antibody to NS1 of a Flavivirus, optionally further comprising detecting in said first sample an IgM and/or IgG class, preferably IgM class antibody to NS1 of a Flavivirus, more preferably SEQ ID NO: 1. In a preferred embodiment, the method further comprises the step detecting in a second sample obtained from said subject an IgA class antibody to NS1 of said Flavivirus, optionally further comprising detecting in said second sample an IgM and/or IgG class, preferably IgM class antibody to NS1 of a Flavivirus such as SEQ ID NO: 1, optionally further comprising detecting in said first sample an IgM and/or IgG class, preferably IgM class antibody to NS1 of a Flavivirus, more preferably SEQ ID NO: 1.

A dynamic titer of IgA or IgM, preferably IgA class antibodies to NS1 of a Flavivirus, preferably to SEQ ID NO: 1, increasing and decreasing significantly relatively to the background before emergence of IgG class antibodies (i.e. seroconversion), may indicate an acute Zika infection, which is a primary Flavivirus infection. By contrast, a parallel increase of IgA and IgG (albeit the latter at higher levels) may indicate an acute Zika infection, which is a secondary Flavivirus infection. In a preferred embodiment, the first sample is obtained at least 3, 4, 5, 6 days, 1, 2 3 or 4 weeks following the subject's exposure or suspected exposure to a Flavivirus. In a preferred embodiment, the first sample is taken in the two weeks after onset of symptoms. The presence or absence of antibodies may be determined as well as their relative levels overtime. The second sample may be obtained at least 3, 4, 5, 6 days, 1, 2, 4, 6, 8, 12, 16, 20, 24, 28 or 32 weeks later than the first sample, preferably at least 3 days, more preferably at least 7 days. A total number of at least 2, 3, 4, 5 or six samples may be taken, preferably at least 2 samples, optionally each sample at least 1 day, 3 days, one week, preferably one week after the previous sample. The total concentrations of IgG, IgM and/or IgA, preferably IgM, may be determined in addition, for example to rule out insufficiencies. This way, the titers of the respective antibodies may be monitored overtime.

In a preferred embodiment, the titer of IgM, IgG and/or IgA, preferably IgA and IgG, more preferably IgA to NS1, preferably to SEQ ID NO: 1, is monitored by detecting the presence or absence or, preferably relative level over time for a period of at least 3, 4, 5, 6, 10, 14, 21, 28, 35 or 42 days, preferably at least 6 days, with the first sample being taken at least five days, preferably at least 7 days following onset of the symptoms. Seroconversion may be detected by monitoring the presence or absence or relative level over time of IgG class antibodies to NS1, preferably SEQ ID NO: 1. This may help identify the time window in which the increase and decrease of IgM and/or IgA class antibodies would be expected or concluding that this time window has passed.

The inventive method, kit and carriers may be used to distinguish between a primary and a secondary Flavivirus infection. In a preferred embodiment, the term "primary infection", as used herein, refers to an infection of a person who has never had an infection with said Flavivirus or another Flavivirus, preferably said Flavivirus, more preferably the Zika virus, by contrast to a secondary infection in a patient who has been exposed to a virus or immunogenic compositions derived thereof before. In a preferred embodiment, this may involve distinguishing a primary Zika virus infection from a secondary infection with another Flavivirus, preferably selected from the group comprising dengue virus, Yellow fever virus, Tick-borne encephalitis virus, Usutu virus, West Nile virus and Japanese encephalitis virus, preferably dengue virus.

The present invention is further illustrated by the following examples, sequences and figures from which further features, embodiments, aspects and advantages of the present invention may be taken. All methods and materials similar or equivalent to those described herein can be used in the practice or testing of the present invention, with suitable methods and materials being described herein. All publications, patent applications, patents, and other references mentioned herein are incorporated by reference in their entirety, as are priority applications EP16000422.2, EP16000442.0, EP16000454.5 and EP16000454.5. Further, the materials, methods, and examples are illustrative only and are not intended to be limiting, unless otherwise specified.

SEQ ID NO: 1: Zika virus NS1 antigen
SEQ ID NO: 2: dengue virus 1 NS1 antigen
SEQ ID NO: 3: dengue virus 2 NS1 antigen
SEQ ID NO: 4: dengue virus 3 NS1 antigen
SEQ ID NO: 5: dengue virus 4 NS1 antigen
SEQ ID NO: 6: West Nile virus NS1 antigen
SEQ ID NO: 7: Tick-borne encephalitis virus NS1 antigen
SEQ ID NO: 8: Japanese encephalitis virus NS1 antigen
SEQ ID NO: 9: Yellow fever virus NS1 antigen
SEQ ID NO: 10: Zika virus NS1 antigen with C-terminal His tag
SEQ ID NO: 11: Zika virus envelope glycoprotein
SEQ ID NO: 12: dengue virus 1 envelope glycoprotein
SEQ ID NO: 13: dengue virus 2 envelope glycoprotein
SEQ ID NO: 14: dengue virus 3 envelope glycoprotein
SEQ ID NO: 15: dengue virus 4 envelope glycoprotein
SEQ ID NO: 16: West Nile virus envelope glycoprotein
SEQ ID NO: 17: Tick-borne encephalitis virus envelope glycoprotein
SEQ ID NO: 18: Japanese encephalitis virus envelope glycoprotein
SEQ ID NO: 19: Powassan virus NS1 antigen
SEQ ID NO: 20: Zika virus NS1 antigen with C-terminal His tag and additional fused peptide
SEQ ID NO: 21: Zika virus NS1 epitope
SEQ ID NO: 22: Zika virus NS1 epitope
SEQ ID NO: 23: Zika virus NS1 epitope
SEQ ID NO: 24: Zika virus NS1 epitope
SEQ ID NO: 25: Zika virus NS1 epitope
SEQ ID NO: 26: Zika virus NS1 epitope
SEQ ID NO: 27: Yellow fever virus envelope glycoprotein Example 1: Studying the Diagnostic Performance of Zika NS1-Based ELISA Methods
Human Serum Samples Serum samples from patients with ZIKV infection (n=29) and patients with other flaviviral or non-flaviviral infections as well as yellow fever vaccinations (n=128) were examined in this study. Sera from healthy pregnant women (n=100) and blood donors living in flavivirus endemic and non-endemic areas (n=699) served as negative controls. Follow-up samples from a German patient with clinically and serologically confirmed ZIKV infection contracted during a stay in Colombia were tested by the WHO Collaborating Centre for Arbovirus and Hemorrhagic Fever Reference and Research (Hamburg, Germany) and used for time-course analysis of anti-ZIKV antibody levels. All sera were stored at −20° C. until assayed. The samples were used anonymously to maintain confidentiality and the study protocol conformed to the recommendations of the Central Ethical Committee of Germany.

Protein Expression and Purification

Recombinant NS1[ZIKV] was expressed in HEK293T cells using standard cloning and expression methods based on the pTriEx-1 plasmid with an artificial signal sequence and a C-terminal His tag (SEQ ID NO: 20). Transfected cells were cultured at 37° C. and 8.5% $CO_2$ in Dulbecco's modified eagle's medium with 10% fetal calf serum, 100 U/ml penicillin and 0.1 mg/ml streptomycin for three to five days. Cells were harvested, resuspended in 20 mM Tris-HCl pH 7.4, 10% (w/v) sucrose, 5 mM EDTA, 1 mM PMSF and stored at −80° C. until further use.

Cells were resuspended in 20 mmol/l tris chloride pH 8.0, 600 mmol/l sodium chloride, 20 mmol/A magnesium chloride, 20 mmol/l imidazole, 1 mmol/l PMSF, 0.5 mmol/l dithiothreitol. 0.1% TRITON™ X-100, which is a non-ionic surfactant, and lysed by homogenization. Cell debris was removed by centrifugation for 60 minutes at 100,000×g, 4° C. The soluble protein fraction was applied to Nickel Rapid Run (Agarose Bead Technologies, Miami, FL, USA) equilibrated with 5 mmol/l tris chloride pH 8.0, 150 mmol/l sodium chloride, 0.015% (w/v)-TRITON™ X-100, 0.5 mmol/l dithiothreitol, 20 mmol/l imidazole and eluted by increasing the imidazole concentration to 150 mmol/l. The eluates were pooled, diluted with two volumes 20 mmol/l tris chloride pH 8.5, 5 mmol/l EDTA, 1 mmol/l PMSF, 0.015% (w/v) TRITON™ X-100, 1 mmol/l dithiothreitol and cleared by centrifugation at 100,000×g and 4° C. for 60 minutes. The supernatant was loaded onto an anion exchange chromatography column, HITRAP™ Q FF column (GE Lifesciences, Freiburg, Germany) equilibrated with 20 mmol/l tris chloride pH 8.5, 2.5 mmol/l EDTA, 1 mmol/l PMSF, 0.015% (w/v) TRITON™ X-100, 1 mmol/l dithiothreitol, 50 mmol/l sodium chloride, washed and eluted with 20 mmol/l tris chloride pH 8.5, 2.5 mmol/l EDTA, 1 mmol/l PMSF, 0.015% (w/v) TRITON™ X-100, 1 mmol/l dithiothreitol with stepwise increase of sodium chloride from 50 to 1000 mmol/l. All fractions containing NS1 [ZIKV] were pooled and concentrated by ultrafiltration (VIVASPIN™, Sartorius, Göttingen, Germany). The final preparations were stored at −80° C. until further use.

Enzyme-Linked immunosorbent Assay

NS1-coated microtiter-plates (NUNC®, Roskilde, Denmark) and standardized reagents from the commercially available Anti-Zika Virus IgG and IgM ELISA (EUROIMMUN, Lübeck, Germany) were used as recommended by the manufacturer. In brief, sera diluted 1:101 in PBS plus 0.1% (w/v) casein were added to the wells and allowed to react for 60 minutes at 37° C. In case of IgM detection, sera were pre-incubated with rheumatoid factor absorbent for 10 minutes. Bound antibodies were detected applying rabbit anti-human IgG peroxidase conjugate or goat anti-human IgM peroxidase conjugate for 30 min, followed by staining with tetramethylbenzidine for 15 min. The enzymatic reaction was stopped by addition of one volume of 0.5 mol/l sulphuric acid. Optical density was determined photometrically at 450 nm (reference 620 nm). Unless indicated otherwise, all assay procedures were carried out at room temperature.

The cut-off for positivity was validated and optimized by receiver-operating characteristics (ROC). A highly positive index patient serum was diluted to generate a cut-off calibrator that was incubated in every experiment. A ratio of the extinction value of the patient sample over the extinction value of calibrator was calculated.

Statistics

Statistical analyses were performed using GraphPad Prism 6 (GraphPad Software Inc., La Jolla, CA, USA) and SigmaPlot 13.0 analysis software (SSI, San Jose, CA, USA). Confidence intervals (CI 95%) were calculated according to the modified Wald method.

Results

Eukaryotic Expression and Purification of ZIKV-Specific NS1

ZIKV-specific NS1 was expressed in the human cell line HEK293T and purified from the cell lysate (mNS1) or culture supernatant (sNS1). When separated by SDS-PAGE, mNS1 and sNS1 migrated essentially according to their predicted molecular mass (43.9 kDa; FIG. 1).

Development of NS1-Based Anti-ZIKV ELISA

Purified recombinant mNS1 and sNS1 were used as solid phase antigens in ELISA for the detection of anti-ZIKV IgM and IgG, respectively. ROC analyses were performed based on 29 sera from patients with ZIKV infection and 908 controls, including 109 patients with flavivirus infections or vaccinations, 100 pregnant women and 699 blood donors. Areas under the curve (IgM, ≥0.979; IgG, ≥0.956) indicated excellent diagnostic performance (FIGS. 2A and 2B). The cut-off ratio [$OD_{patient\ sample}/OD_{calibrator}$] for assay positivity was set at ≥1.1 for either Ig class. This threshold exceeds the cut-off level with maximum sum of sensitivity and specificity to ensure high assay specificity. Ratios in the range of ≥0.8 to <1.1 were classified as borderline.

Diagnostic Performance of the Anti-ZIKV ELISA

Sensitivity: Out of 29 serum samples from patients with clinically and serologically confirmed ZIKV infection, 24 (82.8%) were positive for anti-ZIKV IgM, 20 (69.0%) for IgG, and 28 (96.6%) for IgM and/or IgG (FIGS. 3A and 3B). 16 sera showed positive reactivity for both IgM and IgG, while 12 sera were positive for either IgM or IgG. Accordingly, highest diagnostic sensitivity is achieved by parallel testing of both Ig classes (FIG. 3C). This approach also allows the categorization of patients by disease state (acute or past infection). For example, analysis of follow-up samples from a patient who showed clinical symptoms after returning from a stay in Colombia revealed a decrease in anti-ZIKV IgM and a significant increase in IgG levels over a period of 16 weeks, confirming acute infection (FIG. 3D).

Specificity: Among 799 healthy controls, only 1/99 (1.0%) Argentinian and 1/500 (0.2%) German blood donors were found anti-ZIKV IgM positive, while 100 healthy US-American blood donors and 100 healthy pregnant women were negative. Anti-ZIKV IgG was present in 1/100 (1.0%) US-American and 1/500 (0.2%) German blood donors, but absent in the cohorts of healthy Argentinian blood donors and pregnant women. Thus, overall specificity amounted to 99.7% for either Ig class (FIGS. 3A and 3B).

Cross-reactivity: Serum panels from 128 clinically and serologically well characterized patients or vaccinees with high titers of antibodies of class IgM and/or IgG against flaviviruses (DENV, YFV, WNV or JEV) and CHIKV were analyzed. Anti-ZIKV IgM reactivity was detectable in 1/34 (2.9%) patients infected with WNV and anti-ZIKV IgG in 1/25 (4.0%) patients infected with JEV (FIGS. 3A and 3B). In both cases, double infections cannot be excluded, so that it remains unclear if ELISA positivity was due to cross-reactions with antibodies against other flaviviruses (false-positive) or due to coinfection with ZIKV (true positive). Considering an overall positivity rate of 1/128 (0.8%) for either Ig class, cross-reactivity can almost entirely be excluded when using the NS1-based ELISA.

Example 2: Preparation of Zika NS1 Antigen

Recombinant NS1[ZIKV] was expressed in HEK293T cells using standard cloning and expression methods based on the pTriEx-1 plasmid with an artificial signal sequence and a C-terminal His tag (SEQ ID NO: 20). Transfected cells were cultured at 37° C. and 8.5% $CO_2$ in Dulbecco's modified eagle's medium with 10% fetal calf serum, 100 U/ml penicillin and 0.1 mg/ml streptomycin for three to five days. Cell culture supernatant was decanted and stored until further use. Cells were harvested, resuspended in 20 mM Tris-HCl pH 7.4, 10% (w/v) sucrose, 5 mM EDTA, 1 mM PMSF and stored at −80° C. until further use.

To prepare mNS1, cells were resuspended in 20 mmol/l tris chloride pH 8.0, 600 mmol/l sodium chloride, 20 mmol/l magnesium chloride, 20 mmol/l imidazole, I mmol/l PMSF, 0.5 mmol/l dithiothreitol, 0.1% TRITON™ X-100 and lysed by homogenization. Cell debris was removed by centrifugation for 60 minutes at 100,000×g, 4° C. The soluble protein fraction was applied to Nickel Rapid Run (Agarose Bead Technologies, Miami, FL, USA) equilibrated with 5 mmol/l tris chloride pH 8.0, 150 mmol/l sodium chloride, 0.015% (w/v) TRITON™ X-100, 0.5 mmol/l dithiothreitol, 20 mmol/l imidazole and eluted by increasing the imidazole concentration to 150 mmol/l. The eluates were pooled, diluted with two volumes 20 mmol/I tris chloride pH 8.5, 5 mmol/l EDTA, 1 mmol/I PMSF, 0.015% (w/v) TRITON™ X-100, 1 mmol/l dithiothreitol and cleared by centrifugation at 100,000×g and 4° C. for 60 minutes. The supernatant was loaded onto a HITRAP™ Q FF column (GE Lifesciences, Freiburg, Germany) equilibrated with 20 mmol/l tris chloride pH 8.5, 2.5 mmol/l EDTA, 1 mmol/l PMSF, 0.015% (w/v) TRITON™ X-100, 1 mmol/l dithiothreitol, 50 mmol/l sodium chloride, washed and eluted with 20 mmol/l tris chloride pH 8.5, 2.5 mmol/l EDTA, 1 mmol/l PMSF, 0.015% (w/v) TRITON™ X-100, 1 mmol/l dithiothreitol with stepwise increase of sodium chloride from 50 to 1000 mmol/l. All fractions containing NS1 [ZIKV] were pooled and concentrated by ultrafiltration (VIVASPIN™, Sartorius, Göttingen, Germany). The final preparations were stored at −80° C. until further use.

To prepare sNSI, cell culture supernatant was adjusted to 5 mmol/l tris chloride pH 8.0, 164 mmol/l sodium chloride, 50 mmol/I magnesium chloride, 20 mmol/l imidazole, 0.1% TRITON™ X-100, cleared by centrifugation for 30 minutes at 17,600×g, 4° C., applied to Nickel Rapid Run (Agarose Bead Technologies, Miami, FL, USA) equilibrated with 5 mmol/l tris chloride pH 8.0, 300 mmol/l sodium chloride, 20 mmol/l imidazole and eluted by increasing the imidazole concentration to 150 mmol/l. All fractions containing NSI [ZIKV] were pooled and concentrated by ultrafiltration (VIVASPIN™, Sartorius, Göttingen, Germany). The final preparations were stored at −80° C. until further use.

To prepare sNS1 in complex with bovine apolipoprotein AI, cell culture supernatant was adjusted to 5 mmol/l tris chloride pH 8.0, 164 mmol/l sodium chloride, 50 mmol/l magnesium chloride, 20 mmol/l imidazole, cleared by centrifugation for 30 minutes at 17,600×g, 4° C. applied to Nickel Rapid Run (Agarose Bead Technologies. Miami, FL, USA) equilibrated with 5 mmol/l tris chloride pH 8.0, 300 mmol/l sodium chloride, 20 mmol/l imidazole and eluted by increasing the imidazole concentration to 150 mmol/l. All fractions containing NS1 [ZIKV]/Apo AI[*Bos taurus*]-complexes were pooled and concentrated by ultrafiltration (VIVASPIN™, Sartorius, Gottingen, Germany). The final preparations were stored at −80° C. until further use.

When separated by SDS-PAGE, NS1 migrated essentially according to its predicted molecular mass (43.9 kDa). Protein identity was verified by mass spectrometry.

Example 3: Preparation of NS1 Oligomers

Protein preparations of mNS1 and sNS1 prepared as in Example 2 were analyzed by analytical gel filtration using a Superdex 200 pg column (GE Healthcare, Munich, Germany). in 20 mmol/l tris chloride pH 8.5, 2.5 mmol/l EDTA, I mmol/l PMSF, 0.015% (w/v) TRITON™ X-100, 1 mmol/l dithiothreitol, 300 mmol/l sodium chloride or 5 mmol/l tris chloride pH 8.0, 300 mmol/l sodium chloride, 150 mmol/l imidazole. Protein mixtures with known molecular weights were run separately and used as a calibrator. Retention times of individual peaks were used to calculate the molecular weight of the observed NSI populations and eluate fractions were analyzed using denaturing/non-denaturing gel electrophoresis under reducing conditions followed by silver staining.

FIG. 4 shows the results of a representative gel filtration run. The retention times of the major mNS1 and sNS1 peaks reveal a molecular weight of 212 kDa (mNS1) and 227 kDa (sNS1) which is in good agreement with hexameric populations ($Mw[NS1_{monomeric}]$=43.9 kDa). mNS1 shows an additional peak at 44 kDa, which most probably resembles its monomeric form. This interpretation is underpinned by the fraction's electrophoretic mobility: both a heat-denatured and a non-denatured aliquot migrates at the same position below 50 kDa, whereas dimeric NS1 would migrate at 70 kDa in the non-heat-denatured aliquot if present in this population.

Protein preparations of mNS1 and sNS1 were treated with or without 16 mmol/l dithiothreitol and incubated at 70° C. or at room temperature for 10 minutes, followed by SDS gel electrophoresis and Coomassie staining. FIG. 5 shows the generation of monomers and dimers (SDS resistant) under various conditions.

Dimeric mNS1 or sNS1 populations could also be generated by detergent treatment of the hexameric population, e.g. 0.1% TRITON™ X-100 or 0.2% sodium dodecylsulfate.

Analytical gel filtration clearly showed that mNS1 and sNS1 exist mainly as hexamers in vitro with a molecular mass of slightly above 200 kDa, however, only the SDS-resistant dimer. migrating with an apparent molecular mass of 70 kDa, could be visualized in an SDS-containing gel. The dimer was further converted into the monomer ($MW[_{NSmonomeric}]$=43.9 kDa) by heat denaturation. This process is independent of disulfide bonds.

Example 4: NS1 Monomers and Dimers May be Used to Detect Antibodies in Patient Serum by Way of Western Blotting Protein preparations of mNS1 and sNS1 prepared as in Example 2 were treated with or without 16 mmol/l dithiothreitol and were incubated for 10 min at 70° C. or at room temperature to achieve monomeric or oligomeric NS1. Both populations were mixed and separated using SDS electrophoresis followed by transfer to a nitrocellulose membrane. Proteins were either stained unspecifically by Ponceau S staining to demonstrate NS1 in monomeric and dimeric form or were incubated with anti-His antibody as a positive control, buffer devoid of serum as negative control and four human sera (dilution 1:51), two of them from healthy blood donors and two from patients suffering from Zika virus infection.

FIG. 6 shows that both patients' sera react with monomeric and dimeric mNS1 and sNS1, but dimeric NS1 is more sensitive. Reduction of monomeric NS1 with dithiothreitol leads to denaturation and further reduces sensitivity. As shown in a subsequent experiment, the analytical sensitivity of reduced NS1 monomers is at least 10 times less than that of non-reduced monomers in a Western blot.

Example 5: NS1 Antigen Stability is Increased in the Presence of Bovine Apolipoprotein AI The following experiment shows that a complex of a polypeptide comprising SEQ ID NO: 1 and mammalian apolipoprotein is more stable in a solution than the polypeptide by itself. Therefore, a mammalian apolipoprotein may be used to stabilize the polypeptide and devices and kits comprising it.

Protein preparations of mNS1, sNS1 and a complex consisting of sNS1 and bovine apolipoprotein A1, the latter made by preparing protein as in Example 1 followed by addition of chromatography fractions comprising the apolipoprotein, were transferred into 50 mmol/l sodium phosphate pH 7.4, 150 mmol/l sodium chloride using desalting spin columns (Zeba Spin, ThermoFisher Scientific, Waltham, USA). An aliquot of each preparation was kept on ice or at room temperature over night to allow for precipitation of non-PBS-soluble proteins. Aliquots were centrifuged for 30 min at 4° C. and 100,000×g, and supernatants and pellets (resuspended in an equivalent volume of 50 mmol/l sodium phosphate pH 7.4, 150 mmol/l sodium chloride, 8 mol/l urea) were analyzed using denaturing gel electrophoresis under reducing conditions followed by Coomassie staining.

Harsh buffer exchange conditions were chosen to provoke aggregation of potentially unstable proteins.

Figure 2A:
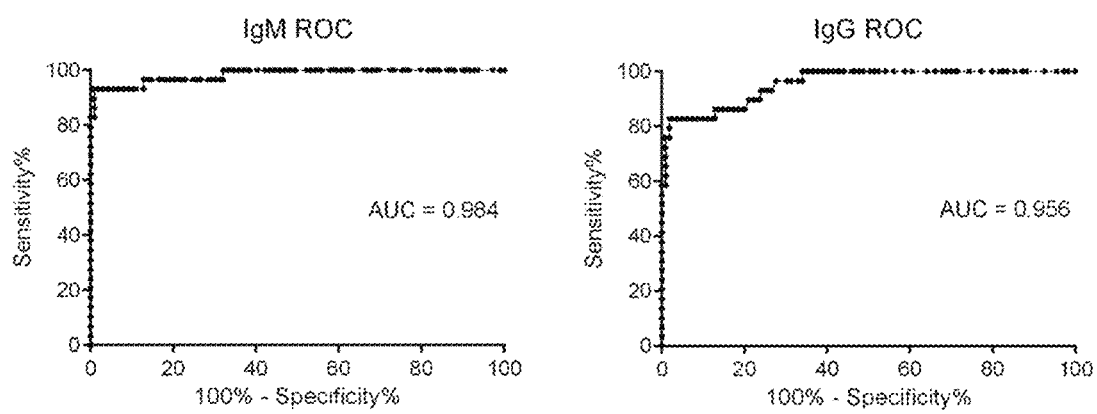
FIG. 2A shows Receiver operating characteristic (ROC) analysis of ELISA for the detection of anti-ZIKV IgM and IgG.
Figure 2B:
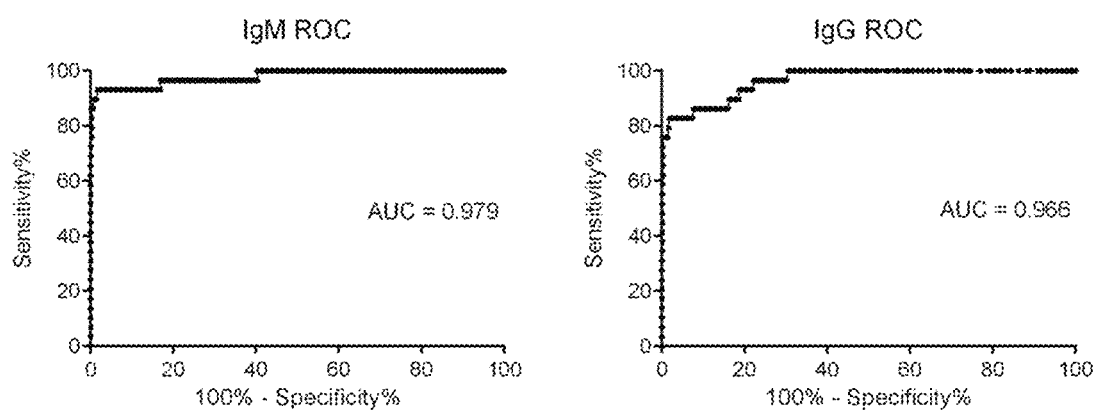
FIG. 2B shows Receiver operating characteristic (ROC) analysis of ELISA for the detection of anti-ZIKV IgM and IgG.
Figure 3A:
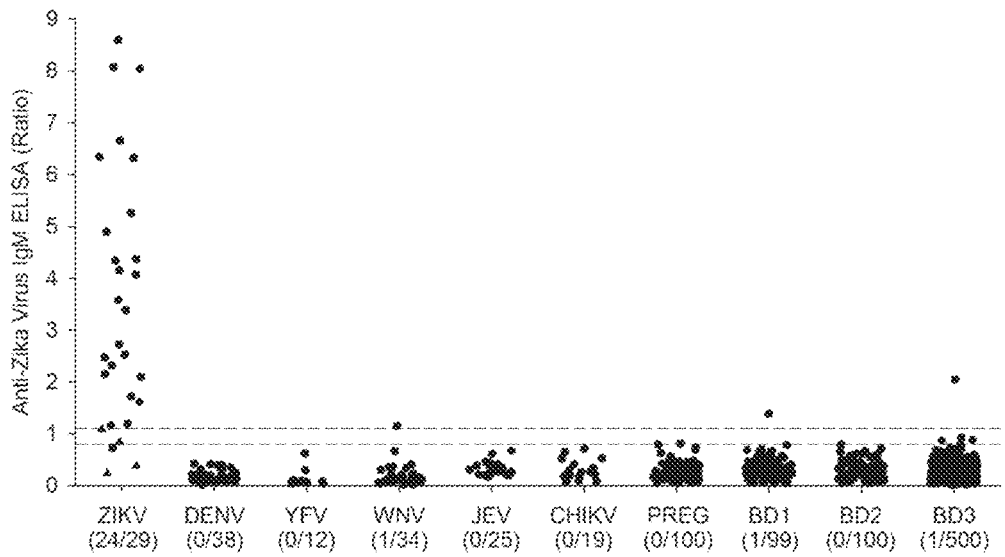
FIG. 3A shows anti-ZIKV reactivity in different cohorts as determined by ELISA. Sera from patients infected with ZIKV, DENV, WNV, JEV or CHIKV or vaccinated against YFV, as well as samples from pregnant women (PREG), Argentinian blood donors (BD1), US-American blood donors (BD2) and German blood donors (BD3) were analyzed for anti-ZIKV IgM by ELISA based on NS1 antigen. Plotted data points represent ratios (extinction of patient sample/extinction of calibrator). Cut-off values for borderline results (≥0.8) and positive results (≥1.1) are indicated by horizontal dotted lines. Positive and total cases are indicated in parentheses. Triangles indicate patients with confirmed ZIKV infection that had a ratio for anti-ZIKV IgM or IgG below the cut-off (<1.1), but a corresponding positive result in IgG or IgM testing, respectively.
Figure 3B:
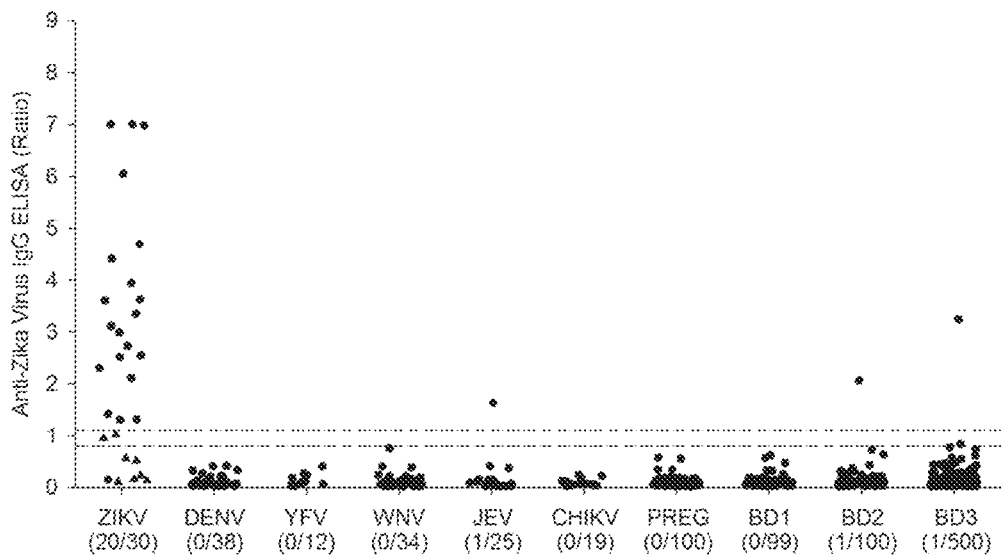
FIG. 3B shows anti-ZIKV reactivity in different cohorts as determined by ELISA. Sera from patients infected with ZIKV, DENV, WNV, JEV or CHIKV or vaccinated against YFV, as well as samples from pregnant women (PREG), Argentinian blood donors (BD1), US-American blood donors (BD2) and German blood donors (BD3) were analyzed for anti-ZIKV IgG by ELISA based on NS1 antigen. Plotted data points represent ratios (extinction of patient sample/extinction of calibrator). Cut-off values for borderline results (≥0.8) and positive results (≥1.1) are indicated by horizontal dotted lines. Positive and total cases are indicated in parentheses. Triangles indicate patients with confirmed ZIKV infection that had a ratio for anti-ZIKV IgM or IgG below the cut-off (<1.1), but a corresponding positive result in IgG or IgM testing, respectively.
Figures 3C, 3D:
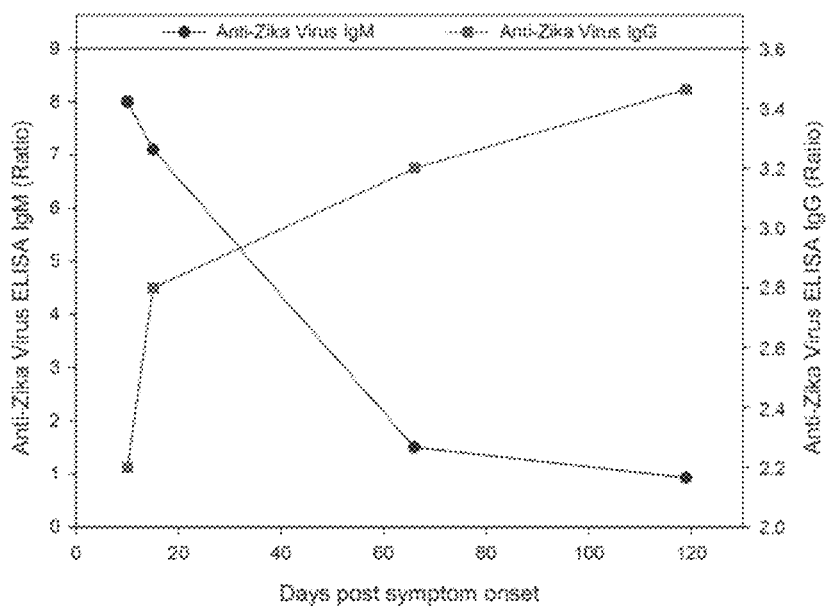
FIG. 3C shows a comparison between anti-ZIKV IgM and IgG detection in the cohort of ZIKV infected patients.
FIG. 3D depicts the time course of anti-ZIKV IgM and IgG antibody levels in the serum of a representative ZIKV-infected patient.
Figure 4:
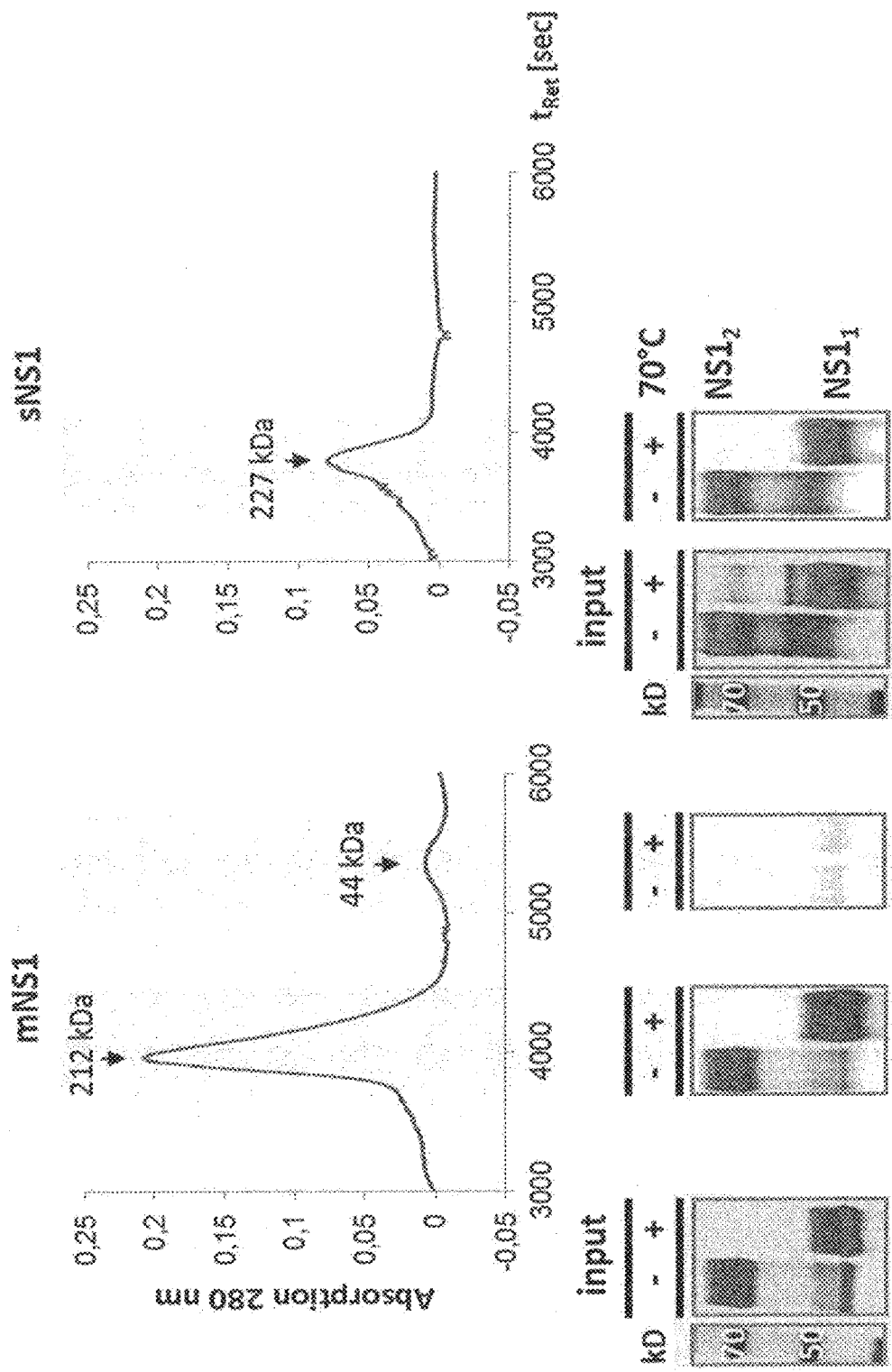
FIG. 4 shows the results of gel filtration with the aim to isolate Zika NS1 oligomers as carried out in Example 2.
Figure 5:
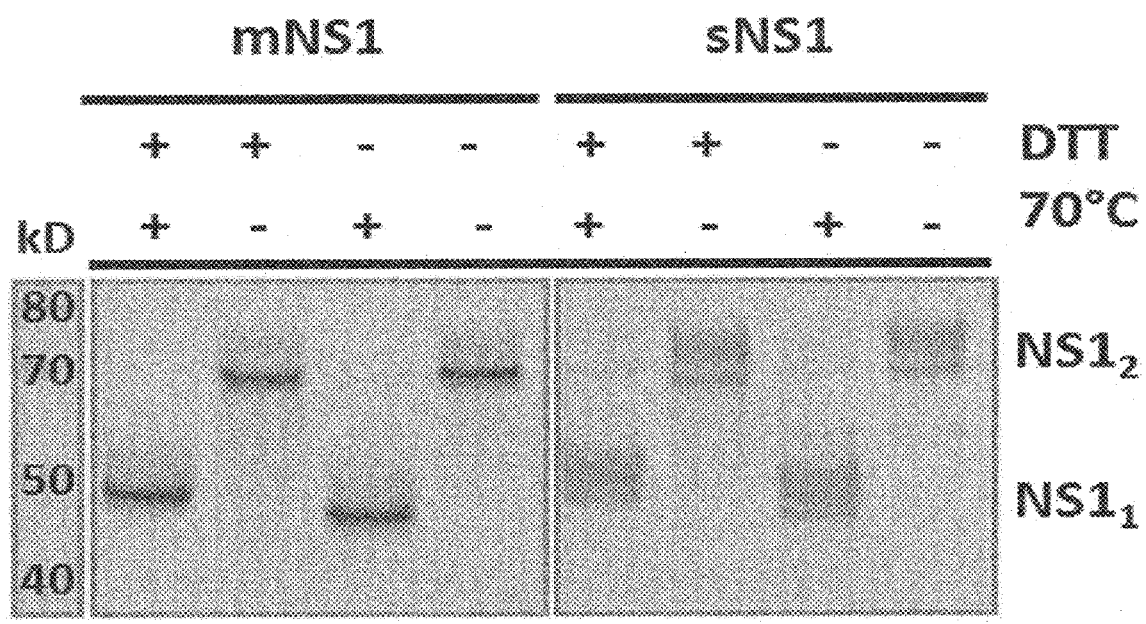
FIG. 5 shows the generation of Zika NS1 monomers and dimers (SDS resistant) under various conditions.
Figure 6:
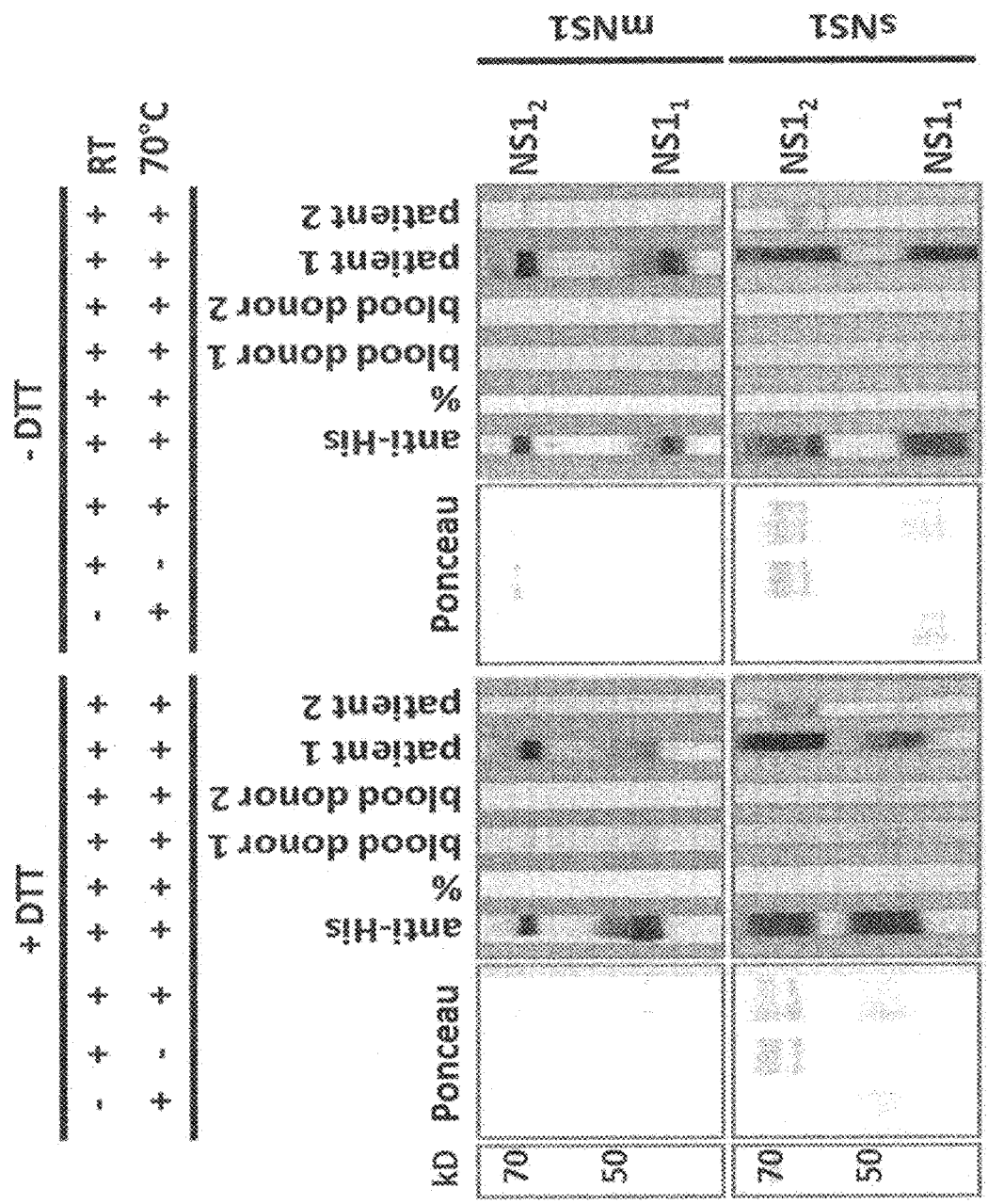
FIG. 6 shows the reaction of two patients' sera with monomeric and dimeric mNS1 and sNS1. Dimeric NS1 is shown to be more sensitive.
Figure 7:
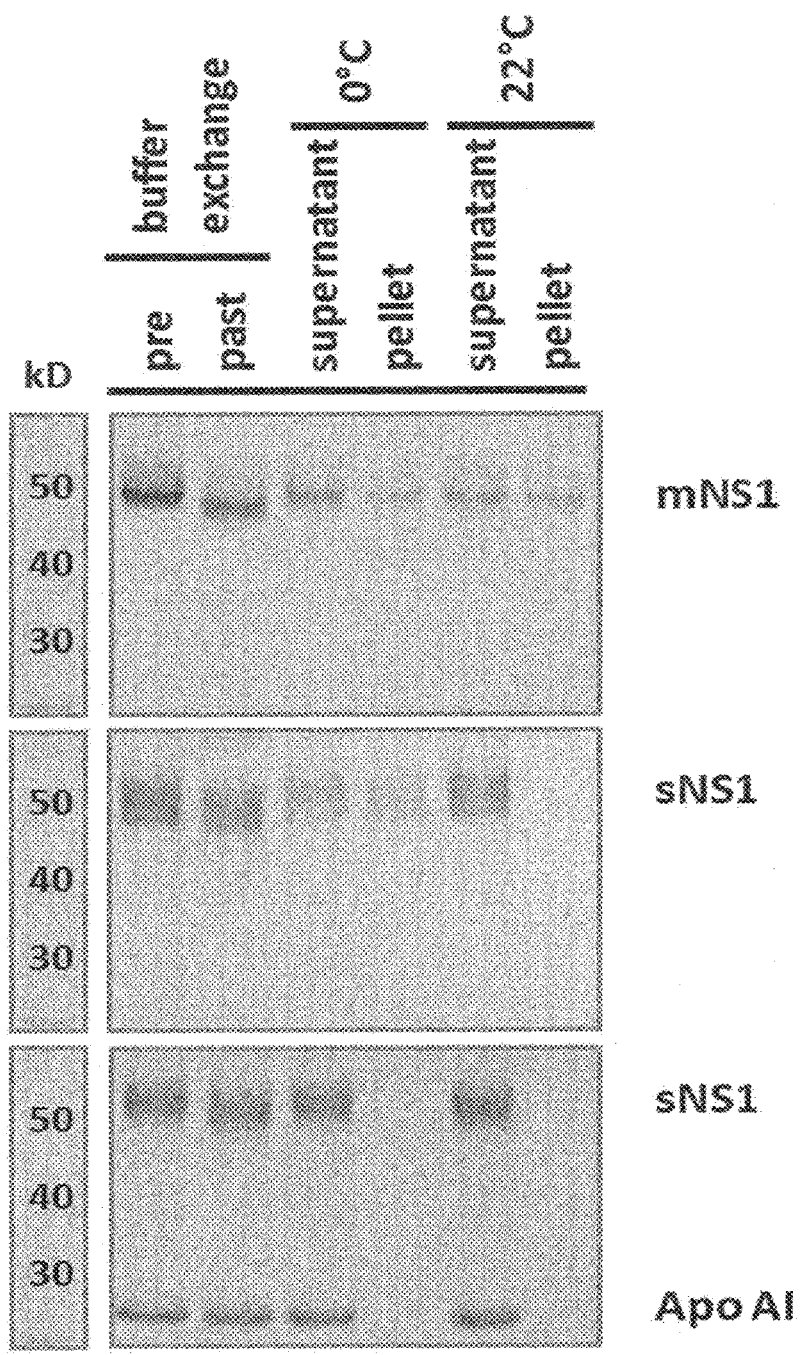
FIG. 7 shows the results of stability studies, more specifically exposure to harsh buffer exchange conditions. A complex comprising sNS1 and bovine apolipoprotein A1 is more stable than NS1 that is not part of such a complex. mNS1 and sNS1 alone can be partially pelleted after incubation on ice or at room temperature, indicating that 30-50% of total protein amount forms aggregates.
Figure 8:
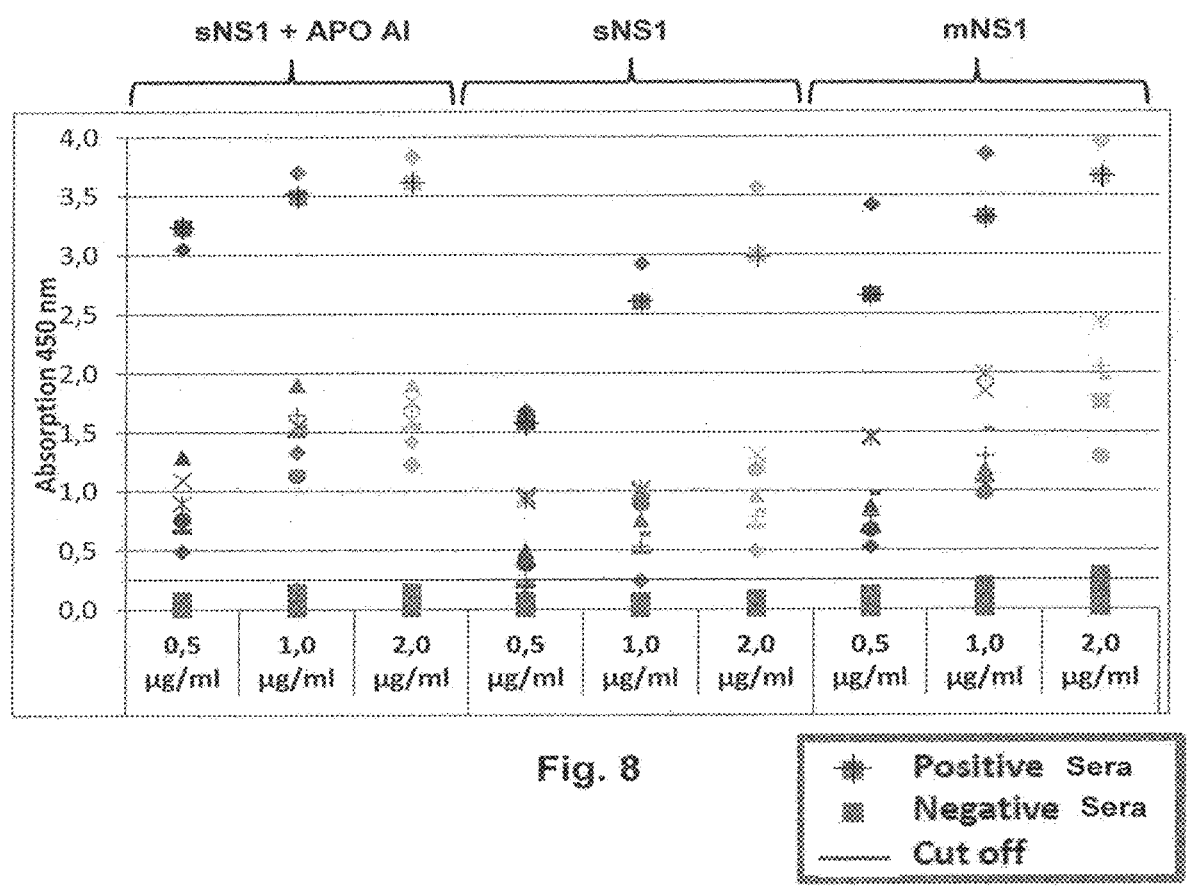
FIG. 8 shows the results of an ELISA to compare the reactivity of various NS1 preparations. A higher reactivity of mNS1 and sNS1+ApoAI compared to sNS1 could be shown.

FIG. 7 shows that mNS1 and sNS1 alone can be partially pelleted after incubation on ice or at room temperature, indicating that 30-50% of total protein amount forms aggregates.

On the other hand, the entirety of sNS1 in complex with bovine apolipoprotein AI remains in the supernatant after centrifugation, indicating a stabilizing effect on sNS1.

Example 6: Comparing Reactivity of Various NS1 Preparations

The following experiment was performed to evaluate the reactivity of different preparations of Zika Virus NS1 antigen in an indirect ELISA for the detection of anti-Zika virus antibodies in human sera. It shows that complexation with a mammalian apolipoprotein increases the reactivity of NS1 and thus the sensitivity of the assay.

Preparation of Coated Microtiter Plates

Three different Zika NS1 preparations were used: sNS1 (soluble NS1 purified from cell culture supernatant), mNS1 (membranous NS1 purified from cells), sNS1+ApoAI (soluble NS1 purified from cell culture supernatant, in complex with bovine ApoAI).

For use in microtiter ELISA these three NS1 preparations were diluted in PBS to final concentrations of 0.5, 1.0 and 2.0 μg/ml, respectively. Microtiter plates were coated with 100 μl antigen dilution per well.

Incubation of Samples:

A set of anti-Zika-NS1 IgM positive or negative human sera was used for evaluation of reactivity of the different antigen preparations. All reagents used during incubation are included in every EUROIMMUN IgM ELISA Test-Kit for infectious diagnostics (e.g. EI 2668-9601 M). Sera were diluted 1:101 in IgM sample buffer containing IgG/RF absorbent and incubated at room temperature for 10 min to absorb rheumatoid factors and IgG. Samples were applied to microtiter plates and incubated as described for commercial EUROIMMUN anti-Zika virus ELISA (IgM) (EI 2668-9601 M). In brief: 60 min at 37° C.; 3 washing steps using EUROIMMUN wash buffer; addition of 100 μl of peroxidase-labelled anti-human IgM conjugate (goat) per well; incubation for 30 min at room temperature; 3 washing steps using EUROIMMUN wash buffer; addition of 100 μl of chromogen/substrate solution (TMB/H2O2) per well; incubation for 15 min at room temperature; addition of 100 μl stop-solution (0.5 M sulfuric acid); measurement of optical density at 450 nm.

Interpretation of Results:

FIG. 8 shows the results, more specifically a higher reactivity of mNS1 and sNS1+ApoAI compared to sNS1. mNS1 and sNS1+ApoAI show comparable reactivity concerning positive sera. With regard to negative sera sNS1+ApoAI shows a lower reactivity compared to mNS1 (even in highest applied coating concentrations) suggesting a higher specificity of the complexed antigen. NS1 could also be shown to form a complex bovine Apolipoprotein B-100 isoform X1, which may also be used for stabilizing the antigen.

Example 7: A Multicohort Study of NS1-Based ELISA Assay Performance Shows Lack of Cross-Reactivity with Dengue Virus Antibodies The diagnostic performance of the assay according to the present invention was examined using sera from returning travellers and patients from ZIKV-endemic areas with laboratory-confirmed ZIKV infection, potentially cross-reactive samples from patients with flaviviral and other infections, as well as control panels from blood donors of different ages and geographical origin.

Methods

Human Sera

The study included serum samples from 27 patients who had tested positive for ZIKV RNA by reverse transcription PCR (RT-PCR); Group 1: travellers returning from endemic areas (n=8); Group 2: residents in ZIKV-endemic areas (n=19). On the basis of direct detection of the pathogen's genome, these cases were referred to as having RT-PCR-confirmed ZIKV infection. Samples from a further 85 patients had been pre-characterised by anti-ZIKV indirect immunofluorescence assay (IIFA; EUROIMMUN, Lübeck, Germany) based on whole virus antigen, showing reactivity for anti-ZIKV IgM and/or IgG; Group 3: travellers returning from endemic areas (n=26); Group 4: residents in ZIKV-endemic areas (n=59). Since false-positive results due to cross-reactivity of this IIFA cannot be excluded, these cases were referred to as having suspected ZIKV infection (Table 1).

Classification into three stages of ZIKV infection was according to the Pan American Health Organization (PAHO)/World Health Organization (WHO) recommendations on ZIKV surveillance in the Americas: ≤5 days post symptom onset, initial stage; 6-20 days post symptom onset, active stage; >20 days post symptom onset, late stage. Samples from travellers returning from endemic areas were provided by the diagnostic institutes (listed in Table 1) to which they had been sent for routine diagnostic testing. Samples from patients residing in Latin America (i.e. Dominican Republic and Colombia) were purchased from Boca Biolistics (Coconut Creek, Florida, United States (United States (US)), Allied Research Society (Miami Lakes, Florida, US) and Biomex GmbH (Heidelberg, Germany). As confirmed by these institutes and companies, written informed consent had been obtained from all patients, and there were no legal or ethical restrictions to using the samples.

To evaluate cross-reactivity, samples were used from 252 patients with either a post-YFV vaccination status (n=12), or with other flaviviral (DENV=93; WNV=34, JEV=25), non-flaviviral (CHIKV=19) and *Plasmodium* spp. (PLAS: n=69) infections. In samples from DENV-infected patients, the confirmation of DENV as the infectious agent was based on NS1 antigen detection. Sera from 1,015 healthy individuals (pregnant women, blood donors and children) living in flavivirus-endemic and non-endemic areas served as negative controls. Pre-characterisation data for all control cohorts are reported in Table 2. To the best of the authors' knowledge, none of these samples were analysed in previous studies.

TABLE 1

Characteristics of patients with RT-PCR-confirmed (n = 27) and suspected (n = 85) Zika virus infection, study evaluating a novel NS1-based ELISA, Germany 2016

| Case ID | Age groups in years | Sex | Country of infection | Current/former residence | Sampling Dpso | Phase of infection[a] | Clinical symptoms[b] | Diagnostic centre/provider of samples | ZIKV-RT-PCR assay/ performed at | ZIKV-RT-PCR result[c] | Virus neutralisation assay titre | IIFA IgM titre[d] | IIFA IgG titre[d] |
|---|---|---|---|---|---|---|---|---|---|---|---|---|---|
| Group 1: RT-PCR-confirmed ZIKV infection, travellers returning from ZIKV-endemic areas (n = 8) |||||||||||||| 
| 1 | 20-29 | M | NA | Non-endemic | 7 | Active | Yes | WHOCC, Hamburg, Germany | RealStar Zika Virus RT-PCR (Altona Diagnostics, Hamburg, Germany)/ WHOCC | Pos | NA | 1:3,200 | 1:3,200 |
| 2 | 30-39 | F | Haiti | Non-endemic | ≥4 | Active | Yes | | | Pos | NA | 1:320 | 1:32,000 |
| 3 | 50-59 | M | NA | Non-endemic | 3 | Initial | No | | | Pos | NA | NA | NA |
| 4 | 50-59 | F | NA | Non-endemic | <4 | Initial | NA | | | Pos | NA | 1:100 | 1:1,000 |
| 5 | 20-29 | F | NA | Non-endemic | 17 | Active | NA | ITM, Antwerp, Belgium | RealStar Zika Virus RT-PCR (Altona Diagnostics, Hamburg, Germany)/ ITM | Pos | >1:640 | NA | NA |
| 6 | 40-49 | M | NA | Non-endemic | 11 | Active | NA | | | Pos | 1:243 | NA | NA |
| 7 | 0-9 | M | NA | Non-endemic | 3 | Initial | NA | | | Pos | 1:788 | NA | NA |
| 8 | 20-29 | F | NA | Non-endemic | 11 | Active | NA | | | Pos | | NA | NA |
| Group 2: RT-PCR-confirmed ZIKV infection, residents in ZIKV-endemic areas (n = 19) |||||||||||||| 
| 1 | 60-69 | F | Suriname | The Netherlands/Suriname[e] | 3 | Initial | NA | AMC, Amsterdam, the Netherlands | In-house Zika RT-PCR/AMC | Pos | NA | NA | NA |
| 2 | 50-59 | M | Suriname | The Netherlands/Suriname[e] | 5 | Initial | NA | | | Pos | NA | NA | NA |
| 3 | 40-49 | F | Suriname | The Netherlands/Suriname[e] | 11 | Active | NA | | | Pos | NA | NA | NA |
| 4 | 40-49 | M | Suriname | The Netherlands/Suriname[e] | 9 | Active | NA | | | Pos | NA | NA | NA |
| 5 | 50-59 | F | Suriname | The Netherlands/Suriname[e] | 6 | Active | NA | | | Pos | NA | NA | NA |
| 6 | 50-59 | F | Suriname | The Netherlands/Suriname[e] | 6 | Active | NA | | | Pos | NA | NA | NA |
| 7 | 50-59 | F | Suriname | The Netherlands/Suriname[e] | 53 | Late | NA | | | Pos | NA | NA | NA |
| 8 | 50-59 | F | Suriname | The Netherlands/Suriname[e] | 17 | Active | NA | | | Pos | NA | NA | NA |
| 9 | 60-69 | F | Suriname | The Netherlands/Suriname[e] | 24 | Late | NA | | | Pos | NA | NA | NA |
| 10 | 70-79 | M | Suriname | The Netherlands/Suriname[e] | 6 | Active | NA | | | Pos | NA | NA | NA |
| 11 | 0-9 | F | Dominican Republic | The Netherlands | 1 | Initial | NA | | | Pos | NA | NA | NA |
| 12 | 50-59 | F | Dominican Republic | Dominican Republic | 20 | Active | Yes | Boca Biolistics, Coconut Creek, Florida, US | Trioplex real-time RT-PCR (CDC, Atlanta, Georgia, US)/CDC | Pos | NA | 0 | 1:32,000 |
| 13 | 50-59 | F | Dominican Republic | Dominican Republic | 31 | Late | Yes | | | Pos | NA | 1:100 | 1:32,000 |
| 14 | 20-29 | M | Colombia | Colombia | 3 | Initial | Yes | Allied Research Society, Miami Lakes, Florida, US | Trioplex real-time RT-PCR (CDC, Atlanta, Georgia, US)/CDC | Pos | NA | 0 | 1:1,000 |
| 15 | 40-49 | F | Colombia | Colombia | 5 | Initial | Yes | | | Pos | NA | 0 | 1:1,000 |
| 16 | 50-59 | F | Colombia | Colombia | 4 | Initial | Yes | | | Pos | NA | 1:10 | 1:3,200 |
| 17 | 10-19 | M | Colombia | Colombia | 3 | Initial | Yes | | | Pos | NA | 0 | 1:3,200 |
| 18 | 20-29 | F | Colombia | Colombia | 6 | Active | Yes | Biomex GmbH, Heidelberg, Germany | RealStar Zika Virus RT-PCR (Altona Diagnostics, Hamburg, Germany) | Pos | NA | 1:3,200 | 1:32,000 |

TABLE 1-continued

Characteristics of patients with RT-PCR-confirmed (n = 27) and suspected (n = 85) Zika virus infection, study evaluating a novel NS1-based ELISA, Germany 2016

| Case ID | Age groups in years | Sex | Country of infection | Current/former residence | Sampling Dpso | Phase of infection[a] | Clinical symptoms[b] | Diagnostic centre/provider of samples | ZIKV-RT-PCR assay/performed at | ZIKV-RT-PCR result[c] | Virus neutralisation assay titre | IIFA IgM titre[d] | IIFA IgG titre[d] |
|---|---|---|---|---|---|---|---|---|---|---|---|---|---|
| 19 | 10-19 | M | Colombia | Colombia/US | 15 | Active | Yes | WHOCC, Hamburg, Germany | Altona Diagnostics Trioplex real-time RT-PCR (CDC, Atlanta, Georgia, US)CDC | Pos | NA | 1:10 | 1:32,000 |

Group 3: Suspected ZIKV infection, travellers returning from ZIKV-endemic areas (n = 26)

| 1 | NA | NA | NA | Non-endemic | NA | NA | NA | | NA | NA | NA | 1:3,200 | 1:10,000 |
| 2 | NA | NA | NA | Non-endemic | NA | NA | NA | | | NA | NA | 1:1,000 | 1:10,000 |
| 3 | NA | NA | NA | Non-endemic | NA | NA | NA | | | NA | NA | 1:3,200 | 1:10,000 |
| 4 | NA | NA | Brazil | Non-endemic | NA | NA | NA | | | NA | NA | 1:1,000 | 1:32,000 |
| 5 | NA | NA | Brazil | Non-endemic | NA | NA | NA | | | NA | NA | 1:1,000 | 1:3,200 |
| 6 | NA | NA | Brazil | Non-endemic | NA | NA | NA | | | NA | NA | 1:3,200 | 1:10,000 |
| 7 | NA | NA | NA | Non-endemic | NA | NA | NA | | | NA | NA | 1:100 | <1:100 |
| 8 | NA | NA | NA | Non-endemic | NA | NA | NA | | | NA | NA | 1:1,000 | 1:100 |
| 9 | NA | NA | NA | Non-endemic | NA | NA | NA | | | NA | NA | 1:320 | 1:10,000 |
| 10 | NA | NA | NA | Non-endemic | NA | NA | NA | | | NA | NA | 1:320 | 1:32,000 |
| 11 | NA | NA | Brazil | Non-endemic | NA | 19 | Active | Yes | | NA | NA | 1:100 | 1:10,000 |
| 12 | NA | NA | Brazil | Non-endemic | NA | NA | NA | | | NA | NA | 1:320 | 1:100,000 |
| 13 | NA | NA | Brazil | Non-endemic | NA | NA | NA | | | NA | NA | 1:1,000 | 1:320 |
| 14 | NA | NA | NA | Non-endemic | NA | NA | NA | | | NA | NA | 1:320 | 1:3,200 |
| 15 | NA | NA | Brazil | Non-endemic | NA | NA | NA | | | NA | NA | 1:320 | 1:1,000 |
| 16 | NA | NA | Brazil | Non-endemic | NA | NA | NA | | | NA | NA | 1:1,000 | 1:10,000 |
| 17 | NA | NA | Brazil | Non-endemic | NA | NA | NA | | | NA | NA | 1:320 | 1:10,000 |
| 18 | NA | NA | NA | Non-endemic | NA | 32 | Late | NA | | NA | NA | 1:100 | 1:32,000 |
| 19 | NA | NA | Colombia | Non-endemic | NA | 45 | Late | NA | | NA | NA | 1:1,000 | 1:3,200 |
| 20 | NA | NA | NA | Non-endemic | NA | NA | NA | | | NA | NA | 1:1,000 | 1:10,000 |
| 21 | NA | NA | Denmark | Non-endemic | NA | NA | NA | | | NA | NA | 1:100 | 1:32,000 |
| 22 | NA | NA | NA | Non-endemic | NA | NA | NA | | | NA | NA | 1:3,200 | 1:32,000 |
| 23 | NA | NA | Colombia | Non-endemic | NA | NA | NA | | | NA | NA | 1:100 | 1:10,000 |
| 24 | NA | NA | Brazil | Non-endemic | NA | NA | NA | | | NA | NA | 1:320 | 1:10,000 |
| 25 | NA | NA | Brazil | Non-endemic | NA | NA | NA | | | NA | NA | 1:320 | 1:32,000 |
| 26 | NA | NA | Colombia | Non-endemic | NA | 15 | Active | NA | | NA | NA | 1:100 | 1:10,000 |

Group 4: Suspected ZIKV infection, residents in ZIKV-endemic areas (n = 59)

| 1 | 30-39 | F | Colombia | Colombia | 6 | Active | Yes | Allied Research Society, Miami Lakes, Florida, US | NA | NA | NA | 1:1,000 | 1:320,000 |
| 2 | 20-29 | M | Colombia | Colombia | 8 | Active | Yes | | | NA | NA | 1:100 | 1:1,000 |
| 3 | 30-39 | F | Colombia | Colombia | 11 | Active | Yes | | | NA | NA | 0 | 1:1,000 |
| 4 | 40-49 | M | Colombia | Colombia | 14 | Active | Yes | | | NA | NA | 1:3,200 | 1:320,000 |
| 5 | 30-39 | F | Colombia | Colombia | 17 | Active | Yes | | | NA | NA | 1:3,200 | 1:320,000 |
| 6 | 80-89 | M | Colombia | Colombia | 20 | Active | Yes | | | NA | NA | 1:320 | 1:320,000 |
| 7 | 50-59 | F | Colombia | Colombia | 23 | Late | Yes | | | NA | NA | 1:320 | 1:10,000 |
| 8 | 30-39 | M | Colombia | Colombia | 30 | Late | Yes | | | NA | NA | 1:3,200 | 1:320,000 |
| 9 | 40-49 | F | Colombia | Colombia | 49 | Late | Yes | | | NA | NA | 1:100 | 1:10,000 |
| 10 | 10-19 | F | Colombia | Colombia | 54 | Late | Yes | | | NA | NA | 1:10 | 1:1,000 |

TABLE 1-continued

Characteristics of patients with RT-PCR-confirmed (n = 27) and suspected (n = 85) Zika virus infection, study evaluating a novel NS1-based ELISA, Germany 2016

| Case ID | Age groups in years | Sex | Country of infection | Current/former residence | Sampling Dpso | Phase of infection[a] | Clinical symptoms[b] | Diagnostic centre/provider of samples | ZIKV-RT-PCR assay/performed at | ZIKV-RT-PCR result[c] | Virus neutralisation assay titre | IIFA IgM titre[d] | IIFA IgG titre[d] |
|---|---|---|---|---|---|---|---|---|---|---|---|---|---|
| 11 | 50-59 | F | Colombia | Colombia | 6 | Active | Yes | | | NA | NA | 0 | 1:3,200 |
| 12 | 40-49 | F | Colombia | Colombia | 4 | Initial | Yes | | | NA | NA | 0 | 1:1,000 |
| 13 | 10-19 | M | Colombia | Colombia | 66 | Late | Yes | | | NA | NA | 0 | 1:32,000 |
| 14 | 40-49 | F | Colombia | Colombia | 68 | Late | Yes | | | NA | NA | 1:10 | 1:32,000 |
| 15 | 50-59 | F | NA | Colombia | 70 | Late | Yes | | | NA | NA | 0 | 1:32,000 |
| 16 | 40-49 | F | NA | Colombia | 2 | Initial | Yes | | | NA | NA | 0 | 1:10,000 |
| 17 | 20-29 | F | Colombia | Colombia | 7 | Active | Yes | | | NA | NA | 1:100 | 1:320,000 |
| 18 | 50-59 | F | NA | Colombia | 4 | Initial | Yes | | | NA | NA | 1:100 | 1:100,000 |
| 19 | 40-49 | M | Colombia | Colombia | 3 | Initial | Yes | | | NA | NA | 1:10,000 | 1:32,000 |
| 20 | 40-49 | F | Colombia | Colombia | 4 | Initial | Yes | | | NA | NA | 1:32 | 1:32,000 |
| 21 | 30-39 | M | Colombia | Colombia | 4 | Initial | Yes | | | NA | NA | 1:32 | 1:32,000 |
| 22 | 40-49 | F | Colombia | Colombia | 4 | Initial | Yes | | | NA | NA | 0 | 1:100,000 |
| 23 | 30-39 | F | Colombia | Colombia | 4 | Initial | Yes | | | NA | NA | 0 | 1:32,000 |
| 24 | 20-29 | F | Colombia | Colombia | 5 | Initial | Yes | | | NA | NA | 1:10 | 1:10,000 |
| 25 | 40-49 | F | Colombia | Colombia | 5 | Initial | Yes | | | NA | NA | 1:1,000 | 1:100,000 |
| 26 | 30-39 | F | Colombia | Colombia | 3 | Initial | Yes | | | NA | NA | 0 | 1:3,200 |
| 27 | 40-49 | F | Colombia | Colombia | 4 | Initial | Yes | | | NA | NA | 0 | 1:32,000 |
| 28 | 20-29 | F | Colombia | Colombia | 3 | Initial | Yes | | | NA | NA | 0 | 1:320 |
| 29 | 50-59 | F | Colombia | Colombia | 4 | Initial | Yes | | | NA | NA | 0 | 1:10,000 |
| 30 | 20-29 | F | Colombia | Colombia | 3 | Initial | Yes | | | NA | NA | 1:32 | 1:10,000 |
| 31 | 30-39 | F | Colombia | Colombia | 3 | Initial | Yes | Biomex GmbH, Heidelberg, Germany | NA | NA | NA | 0 | 1:32,000 |
| 32 | 20-29 | F | Colombia | Colombia | 4 | Initial | Yes | | | NA | NA | 1:100 | 1:32,000 |
| 33 | 10-19 | F | Colombia | Colombia | 9 | Active | Yes | | | NA | NA | 1:100 | 1:10,000 |
| 34 | 20-29 | F | Colombia | Colombia | 12 | Active | Yes | | | NA | NA | 0 | 1:32,000 |
| 35 | 10-19 | F | Colombia | Colombia | 20 | Active | Yes | | | NA | NA | 1:100 | 1:10,000 |
| 36 | 20-29 | F | Colombia | Colombia | 27 | Late | Yes | | | NA | NA | 1:320 | 1:10,000 |
| 37 | 30-39 | F | Colombia | Colombia | 36 | Late | Yes | | | NA | NA | 1:10 | 1:32,000 |
| 38 | 10-19 | F | Colombia | Colombia | 56 | Late | Yes | | | NA | NA | 1:100 | 1:10,000 |
| 39 | 30-39 | F | Colombia | Colombia | 67 | Late | Yes | | | NA | NA | 1:10 | 1:10,000 |
| 40 | 10-19 | F | Colombia | Colombia | 2 | Initial | Yes | Allied Research Society, Miami Lakes, Florida, US | NA | NA | NA | 0 | 1:10,000 |
| 41 | 30-39 | F | Colombia | Colombia | 5 | Initial | Yes | | | NA | NA | 1:320 | 1:10,000 |
| 42 | 20-29 | F | Colombia | Colombia | 6 | Active | Yes | | | NA | NA | 1:100 | 1:32,000 |
| 43 | 20-29 | F | Colombia | Colombia | 8 | Active | Yes | | | NA | NA | 1:100 | 1:10,000 |
| 44 | 30-39 | F | Colombia | Colombia | 15 | Active | Yes | | | NA | NA | 0 | 1:10,000 |
| 45 | 20-29 | F | Colombia | Colombia | 21 | Late | Yes | | | NA | NA | 1:10 | 1:100,000 |
| 46 | 20-29 | F | Colombia | Colombia | 29 | Late | Yes | | | NA | NA | 1:320 | 1:32,000 |
| 47 | 20-29 | F | Colombia | Colombia | 38 | Late | Yes | | | NA | NA | 1:1,000 | 1:320,000 |
| 48 | 10-19 | F | Colombia | Colombia | 50 | Late | Yes | | | NA | NA | 1:10 | 1:10,000 |
| 49 | 20-29 | F | Colombia | Colombia | 88 | Late | Yes | | | NA | NA | 0 | 1:1,000 |
| 50 | 40-49 | M | Colombia | Colombia | 2 | Initial | Yes | | | NA | NA | 0 | 1:3,200 |
| 51 | 20-29 | F | Colombia | Colombia | 5 | Initial | Yes | | | NA | NA | 1:1,000 | 1:32,000 |
| 52 | 30-39 | F | Colombia | Colombia | 6 | Active | Yes | | | NA | NA | 0 | 1:1,000 |
| 53 | 20-29 | M | Colombia | Colombia | 8 | Active | Yes | | | NA | NA | 0 | 1:10,000 |
| 54 | 30-39 | F | Colombia | Colombia | 15 | Active | Yes | | | NA | NA | 1:320 | 1:320,000 |
| 55 | 30-39 | M | Colombia | Colombia | 21 | Late | Yes | | | NA | NA | 1:100 | 1:32,000 |
| 56 | 40-49 | M | Colombia | Colombia | 29 | Late | Yes | | | NA | NA | 1:32,000 | 1:32,000 |
| 57 | 40-49 | F | Colombia | Colombia | 38 | Late | Yes | | | NA | NA | 0 | 1:320 |

TABLE 1-continued

Characteristics of patients with RT-PCR-confirmed (n = 27) and suspected (n = 85) Zika virus infection, study evaluating a novel NS1-based ELISA, Germany 2016

| Case ID | Age groups in years | Sex | Country of infection | Current/former residence | Sampling Dpso | Phase of infection[a] | Clinical symptoms[b] | Diagnostic centre/provider of samples | ZIKV-RT-PCR assay/ performed at | ZIKV-RT-PCR result[c] | Virus neutralisation assay titre | IIFA IgM titre[d] | IIFA IgG titre[d] |
|---|---|---|---|---|---|---|---|---|---|---|---|---|---|
| 58 | 50-59 | F | Colombia | Colombia | 50 | Late | Yes | | | NA | NA | 0 | 1:100,000 |
| 59 | 50-59 | M | Colombia | Colombia | 85 | Late | Yes | | | NA | NA | 0 | 1:32,000 |

AMC: Academic Medical Center; CDC: Centers for Disease Control and Prevention; dpso: days post symptom onset; F: female; IIFA: indirect immunofluorescence assay; ITM: Institute of Tropical Medicine, M: male; NA: not available; NS: non-structural protein; Pos: positive; US: United States; WHOCC: World Health Organization Collaborating Centre (for Arbovirus and Haemorrhagic Fever Reference and Research); ZIKV: Zika virus.
[a]Phase of infection at the time of sample collection: initial phase: ≤5 dpso; active phase: 6 to 20 dpso; late phase: >20 dpso.
[b]Fever, skin rash, joint pain, myalgia, headache, conjunctivitis, eye pain, diarrhoea and malaise.
[c]ZIKV-RT-PCR results can also refer to serum or urine samples taken at an earlier date than the samples used for anti-ZIKV serological testing.
[d]IIFA was performed at EUROIMMUN, Lübeck, Germany, using the Anti-Zika Virus IIFA test kit (EUROIMMUN). Cut-off IgM: ≥1:10; IgG: ≥1:100.
[e]Sera from Dutch residents who were born and raised in Suriname and/or had visited their country of origin occasionally.

TABLE 2

Characteristics of control cohorts, study evaluating a novel NS1-based ELISA, Germany 2016 anonymised to the Institute for Experimental Immunology (affiliated to EUROIMMUN). All sera were stored at −20° C. until assayed. The study was performed according to the recommendations of the Central Ethical Committee of Germany [29].

| Cohort | n | Origin of sample donors | Type | Diagnostic centre (provider of samples) |
|---|---|---|---|---|
| | | | Flavivirus infection or vaccination | |
| DENVa (high IgM) | 47 | Germany, Italy | Returning travellers from endemic areas with DENV infection (contracted e.g. in Brazil, Bali, Thailand, Laos, Philippines, India, Cambodia, Taiwan) | MVZ Diamedes GmbH Bielefeld, Germany; University of Bologna, Bologna, Italy; WHOCC, Hamburg, Germany |
| DENVb (high IgG) | 46 | Germany, Italy | Returning travellers from endemic areas with DENV infection (contracted e.g. in Brazil, Bali, Thailand, Laos, Philippines, India, Cambodia, Taiwan) | MVZ Diamedes GmbH Bielefeld, Germany; University of Bologna, Bologna, Italy |
| YFV | 12 | France | Individuals vaccinated against YFV | Cerba Specimen Services, Saint-Ouen l'Aumône, France |
| WNV | 34 | US | Patients from endemic areas with WNV infection | MAYO Clinic, Scottsdale, Arizona, US |
| JEV | 25 | Vietnam | Patients from endemic areas with JEV infection | National Hospital of Tropical Disease, Hanoi, Vietnam |
| | | | Non-flavivirus infection | |
| CHIKV | 19 | Reunion | Patients from endemic areas with CHIKV infection | Cerba Specimen Services, Saint-Ouen l'Aumône, France |
| | | | Parasite infection | |
| PLAS | 69 | France (including overseas department and region Mayotte), French Guiana, Tunisia, Madagascar, Switzerland | Blood donors living in and travellers returning from *Plasmodium*-endemic areas, acute or past *Plasmodium* infection | TheBindingSite, Schwetzingen, Germany Cerba Specimen Services, Saint-Ouen l'Aumône, France Swiss Red Cross, Bern, Switzerland |
| | | | Healthy controls: pregnant women, blood donors and children | |
| PREG | 100 | Germany | Pregnant women from non-flavivirus endemic areas without clinical symptoms | Laboratory Schottdorf, Augsburg, Germany |
| ZIM | 128 | Zimbabwe | Blood donors from flavivirus and parasite endemic areas without clinical symptoms | National Blood Transfusion Service, Zimbabwe, Africa |
| ARG | 99 | Argentina | Blood donors from flavivirus endemic areas without signs of viral infection (routine samples for parasitology) | IACA Laboratory, Buenos Aires, Argentina |
| US | 100 | US | Blood donors without clinical symptoms (n): Hispanic (25), African American (30), Caucasian (43), Asian (1), Colombian (1) | Serologix, New Hope, Pasadena, US |
| GER | 500 | Germany | Blood donors from non-flavivirus endemic areas without clinical symptoms | University Medical Center Schleswig-Holstein, Campus Lübeck, Lübeck, Germany |

TABLE 2-continued

Characteristics of control cohorts, study evaluating a novel NS1-based ELISA, Germany 2016 anonymised to the Institute for Experimental Immunology (affiliated to EUROIMMUN). All sera were stored at −20° C. until assayed. The study was performed according to the recommendations of the Central Ethical Committee of Germany [29].

| | | | | |
|---|---|---|---|---|
| CHIL | 88 | Germany | Children (≤10 years) form non-flavivirus endemic areas without clinical symptoms | Praxis Dr Fischer-Wassels, Dortmund, Germany |

| Sample receipt | Pre-characterisation |
|---|---|

Flavivirus infection or vaccination

| | |
|---|---|
| 2011-2014 | Panbio or BIO-RAD DENV-NS1 ELISA[a,b]: 47/47 (100%)DENV-NS1 positive<br>DENV-RT-PCR (only 8/47 tested)[b]: n = 4 subtype DENV-1, n = 2 subtype DENV-2, n = 2 subtype DENV-3<br>EUROIMMUN Anti-DENV ELISA (IgM, IgG)[c]: 40/47 (85%) anti-DENV IgM positive, 30/47 (64%) anti-DENV IgG positive, 37/47 (79%) anti-DENV IgM ratio ≥3.0, 10/47 (21%) anti-DENV IgM ratio <3.0, anti-DENV IgM median ratio = 3.9 |
| 2011-2014 | DENV-NS1 ELISA[a,b]: 46/46 (100%) DENV-NS1 positive<br>DENV-RT-PCR (only 1/46 tested)[b]: n = 1 subtype DENV-4<br>EUROIMMUN Anti-DENV ELISA (IgM, IgG)[c]: 35/46 (76%) anti-DENV IgM positive, 40/46 (87%) anti-DENV IgG positive, 37/46 (80%) anti-DENV IgG ratio ≥3.0, 9/46 (20%) anti-DENV IgG ratio <3.0, anti-DENV IgG median ratio = 3.9 |
| 2015 | YFV seroneutralisation test[d]: 12/12 (100%) anti-YFVpositive<br>EUROIMMUN Anti-WNV ELISA (IgM, IgG)[c]: 0/12 (0%) anti-WNV IgM positive, 0/12 (0%) anti-WNV IgG positive<br>EUROIMMUN Anti-CHIKV ELISA (IgM, IgG)[c]: 0/12 (0%) anti-CHIKV IgM positive, 1/12 (8%) anti-CHIKV IgG positive |
| 2014 | WNV PRNT[e]: 34/34 (100%) anti-WNV positive<br>EUROIMMUN Anti-WNV ELISA (IgM, IgG)[c]: 23/34 (68%) anti-WNV IgM positive, 26/34 (76%) anti-WNV IgG positive |
| 2016 | DRG JE IgM capture ELISA[f]: 25/25 (100%) anti-JEV IgMpositive<br>EUROIMMUN Anti-JEV ELISA (IgM, IgG)[c]: 25/25 (100%) anti-JEV IgM positive, 19/25 (76%) anti-JEV IgG positive |

Non-flavivirus infection

| | |
|---|---|
| 2015 | CHIKV VRP neutralisation test[g]: 19/19 (100%) anti-CHIKVpositive<br>EUROIMMUN Anti-CHIKV ELISA (IgM, IgG)[c]: 0/19 (0%) anti-CHIKV IgM positive, 19/19 (100%) anti-CHIKV IgG positive |

Parasite infection

| | |
|---|---|
| 2016 | BioMérieux *Plasmodium* IFA(IgM, IgG)[d,h]: 1/15 (7%) anti-*Plasmodium* IgM positive, 15/15 (100%) anti-*Plasmodium* IgG positive<br>BIO-RAD Malaria ELISA (IgG)[i]: 54/54 (100%) anti-*Plasmodium* positive |

Healthy controls: pregnant women, blood donors andchildren

| | |
|---|---|
| 2007 | EUROIMMUN Anti-DENV ELISA (IgM, IgG)[c]: 2/100 (2%)anti-DENV IgM positive, 7/100 (7%) anti-DENV IgG positive<br>EUROIMMUN Anti-WNV ELISA (IgM, IgG)[c] 3/100 (3%) anti-WNV IgM positive, 4/100 (4%) anti-WNV IgG positive<br>EUROIMMUN Anti-JEV ELISA (IgM, IgG)[c]: 2/100 (2%) anti-JEV IgM positive, 14/100 (14%) anti-JEV IgG positive<br>EUROIMMUN Anti-CHIKV ELISA (IgM, IgG)[c]: 0/100 (0%) anti-CHIKV IgM positive, 0/100 (0%) anti-CHIKV IgG positive |
| 2003 | EUROIMMUN Anti-DENV ELISA (IgG)[c]: 4/128 (3%) anti-DENVIgG positive<br>EUROIMMUN Anti-CHIKV ELISA (IgG)[c]: 3/128 (2%) anti-CHIKV IgG positive<br>EUROIMMUN Anti-*Plasmodium* ELISA (IgG)[c]: 36/128 (28%)anti-*Plasmodium* IgG positive |
| 2014 | EUROIMMUN Anti-DENV ELISA (IgM, IgG)[c]: 2/99 (2%)anti-DENV IgM positive, 4/99 (4%) anti-DENV IgG positive<br>EUROIMMUN Anti-WNV ELISA (IgM, IgG)[c]: 2/99 (2%) anti-WNV IgM positive, 3/99 (3%) anti-WNV IgG positive<br>EUROIMMUN Anti-CHIKV ELISA (IgM, IgG)[c]: 3/99 (3%) anti-CHIKV IgM positive, 1/99 (1%) anti-CHIKV IgG positive<br>EUROIMMUN Anti-*Trypanosoma* ELISA (IgM, IgG)[c]: 2/99 (2%)anti-*Trypanosoma* IgM positive, 1/99 (1%) anti-*Trypanosoma* IgGpositive |

TABLE 2-continued

Characteristics of control cohorts, study evaluating a novel NS1-based ELISA, Germany 2016 anonymised to the Institute for Experimental Immunology (affiliated to EUROIMMUN). All sera were stored at −20° C. until assayed. The study was performed according to the recommendations of the Central Ethical Committee of Germany [29].

| | |
|---|---|
| 2014 | EUROIMMUN Anti-DENV ELISA (IgM, IgG)[c]: 1/100 (1%)anti-DENV IgM positive, 6/100 (6%) anti-DENV IgG positive<br>EUROIMMUN Anti-WNV ELISA (IgM, IgG)[c]: 0/100 (0%) anti-WNV IgM positive, 4/100 (4%) anti-WNV IgG positive<br>EUROIMMUN Anti-CHIKV ELISA (IgM, IgG)[c]: 0/100 (0%) anti-CHIKV IgM positive, 4/100 (4%) anti-CHIKV IgG positive |
| 2012 | NA |
| 2007-2008 | EUROIMMUN Anti-DENV ELISA (IgM, IgG)[c]: 0/100 (0%)anti-DENV IgM positive, 0/100 (0%) anti-DENV IgG positive<br>EUROIMMUN Anti-WNV ELISA (IgM, IgG)[c]: 1/100 (1%) anti-WNV IgM positive, 0/100 (0%) anti-WNV IgG positive<br>EUROIMMUN Anti-JEV ELISA (IgM, IgG)[c]: 0/100 (0%) anti-JEV IgM positive, 0/100 (0%) anti-JEV IgG positive<br>EUROIMMUN Anti-CHIKV ELISA (IgM, IgG)[c]: 0/100 (0%) anti-CHIKV IgM positive, 0/100 (0%) anti-CHIKV IgG positive |

ARG: Argentina; CHIKV: chikungunya virus; CHIL: children; DENV: dengue virus; IFA: immunofluorescence assay; GER: Germany; JEV: Japanese encephalitis virus; IIFA: indirect immunofluorescence assay; NA: not available; PLAS: *Plasmodium*; PREG: pregnant women; PRNT: plaque reduction neutralisation test; RT-PCR: reverse transcription-PCR; US: United States; WHOCC: World Health Organization Collaborating Centre (for Arbovirus and Haemorrhagic Fever Reference and Research); WNV: West Nile virus; YFV: yellow fever virus; ZIKV: Zika virus; ZIM: Zimbabwe.
[a]Performed at MVZ Diamedis GmbH, Bielefeld, Germany.
[b]Performed at the University of Bologna, Italy.
[c]Performed at EUROIMMUN, Lübeck, Germany.
[d]Performed at Cerba Specimen Services, Saint-Ouen l'Aumône, France.
[e]Performed at the University of Leipzig, Germany.
[f]Performed at the National Hospital of Tropical Disease, Hanoi, Vietnam.
[g]Performed at the University of Bonn, Germany.
[h]Performed at TheBindingSite, Schwetzingen, Germany.
[i]Performed at the Swiss Red Cross, Bern, Switzerland.

Enzyme-Linked Immunosorbent Assays

Anti-Zika Virus IgM and IgG ELISA (EUROIMMUN) were used as recommended by the manufacturer. These kit assays are based on standardised reagents and microtiter plates coated with recombinant ZIKV-NS1. Briefly, sera diluted 1:101 in sample buffer were added to the wells and allowed to react for 60 min at 37° C. Before IgM detection, sera were pre-incubated with sample buffer containing IgG/rheumatoid factor (RF) absorbent (EUROIMMUN) to remove class IgG antibodies and class IgM RF from the sample. This step prevents specific IgG from displacing IgM from the antigen (leading to false IgM-negative results) and RF-IgM from reacting with specifically bound IgG (leading to false IgM-positive results). Bound antibodies were detected by applying goat anti-human IgM peroxidase conjugate or rabbit anti-human IgG peroxidase conjugate for 30 min at room temperature, followed by staining with tetramethylbenzidine for 15 min. The enzymatic reaction was stopped by addition of one volume 0.5 mol/L sulphuric acid. A calibrator (chicken-human chimeric ZIKV antibody with a concentration adjusted to give an extinction value defining the upper limit of the reference range of non-infected persons) as well as positive and negative controls were provided with the test kit and assayed with each test run. Colour intensity of the enzymatic reactions was determined photometrically at 450 nm (reference 620 nm), resulting in extinction values. A signal-to-cut-off ratio ($extinction_{sample}/extinction_{calibrator}$) was calculated for each sample.

Receiver-operating characteristics (ROC) analysis based on the initial validation dataset of positive and negative samples was done by the manufacturer to evaluate assay performance at each possible cut-off, demonstrating optimal sensitivity and specificity at ratio values of 0.8 (IgM) and 0.6 (IgG). To ensure high specificity, the borderline range ($\geq 20.8$ to $<1.1$) was established between the highest negative and the lowest positive validation sample, resulting in a positivity cut-off of $\geq 21.1$.

Anti-dengue Virus IgM and IgG ELISA (EUROIMMUN) were used.

Statistics

Statistical analyses were performed using GraphPad Prism 6 (GraphPad Software Inc., La Jolla, California, US) and SigmaPlot 13.0 (SSI, San Jose, California, US). Sensitivity was calculated as the proportion of ZIKV patients (referring to groups 1 to 4 as indicated) identified as positive by the assay. Specificity was calculated as the proportion of negative test results obtained among healthy controls. We calculated 95% confidence intervals (CIs) according to the modified Wald method. The study was performed in compliance with the Standards for Reporting of Diagnostic accuracy (STARD) statement.

Results

Sensitivity of the Enzyme-Linked Immunosorbent Assay

The sensitivity of the novel NS1-based anti-ZIKV ELISA was evaluated in sera from 27 patients with RT-PCR-confirmed ZIKV infection that had been sub-grouped into travellers returning from ZIKV-endemic areas and endemic-area residents. Among eight infected travellers returning from ZIKV-endemic areas (group 1), positive anti-ZIKV IgM and IgG reactivity was found in seven (87.5%) and three (37.5%) cases, respectively. Of 19 infected residents in endemic-areas (group 2), six (31.6%) were positive for anti-ZIKV IgM and 15 (79.0%) for IgG. In addition, sera from 85 patients with suspected ZIKV infection were examined. Here, of 26 infected travellers returning from ZIKV-endemic areas (group 3) 21 (80.8%) were positive for anti-ZIKV IgM and 18 (69.2%) for IgG, while among 59 infected residents in endemic-areas (group 4), six (10.2%) showed positive reactivity for anti-ZIKV IgM and 53 (89.9%) for IgG. For the total of RT-PCR-confirmed and suspected cases, the combined ELISA sensitivity (IgM and/or IgG) amounted to $23/27$ (85.2%) and $78/85$ (91.8%), respectively.

Confining the time point of serological evaluation to the active and late phase of ZIKV infection, i.e. ≥6 days after symptom onset, anti-ZIKV IgM reactivity was observed in 10/17 (58.8%) patients with positive ZIKV-RT-PCR and 3/38 (7.9%) patients with suspected ZIKV infection, while anti-ZIKV IgG was detectable in 15/17 (88.2%) and 34/38 (89.5%) cases, respectively. Thus, the combined sensitivity (IgM and/or IgG) reached 17/17 (100%) among RT-PCR-confirmed cases and 34/38 (89.5%) among suspected cases (Table 3).

TABLE 3

Anti-ZIKV reactivity in patients with RT-PCR-confirmed (n = 27) and suspected (n = 85) ZIKV infection as determined by ELISA for IgM and IgG, study evaluating a novel NS1-based ELISA, Germany 2016

| Group | Characteristics | | Anti-ZIKV ELISA reactivity (≥1 day post symptom onset)[c] | | | | Anti-ZIKV ELISA reactivity (≥6 days post symptom onset)[d,e] | | | |
|---|---|---|---|---|---|---|---|---|---|---|
| | | | n | IgM | IgG | IgM/IgG | n | IgM | IgG | IgM/IgG |
| 1 | RT-PCR-confirmed ZIKV infection, travellers returning from ZIKV-endemic areas | Positive Sensitivity %[b] (95% CI) | 8 — | 7 87.5 (50.8-99.9) | 3 37.5 (13.5-69.6) | 7 87.5 (50.8-99.9) | 5 — | 5 100 (51.1-100) | 3 60.0 (22.9-88.4) | 5 100 (51.1-100) |
| 2 | RT-PCR-confirmed ZIKV infection, residents in ZIKV-endemic areas[a] | Positive Sensitivity %[b] (95% CI) | 19 — | 6 31.6 (15.2-54.2) | 15 78.9 (56.1-92.1) | 16 84.2 (61.6-95.3) | 12 — | 5 41.7 (19.3-68.1) | 12 100 (71.8-100) | 12 100 (71.8-100) |
| Total 1 + 2 | RT-PCR-confirmed ZIKV infection | Positive Sensitivity %[b] (95% CI) | 27 — | 13 48.1 (30.7-66.0) | 18 66.7 (47.7-81.5) | 23 85.2 (66.9-94.7) | 17 — | 10 58.8 (36.0-78.4) | 15 88.2 (64.4-98.0) | 17 100 (78.4-100) |
| 3 | Suspected ZIKV infection, travellers returning from ZIKV-endemic areas | Positive Sensitivity %[b] (95% CI) | 26 — | 21 80.8 (61.7-92.0) | 18 69.2 (49.9-83.7) | 25 96.2 (79.6-100) | | | NA[e] | |
| 4 | Suspected ZIKV infection, residents ZIKV-endemic areas | Positive Sensitivity %[b] (95% CI) | 59 — | 6 10.2 (4.4-20.8) | 53 89.9 (79.2-95.6) | 53 89.9 (79.2-95.6) | 38 — | 3 7.9 (2.0-21.5) | 34 89.5 (75.3-96.4) | 34 89.5 (75.3-96.4) |
| Total 3 + 4 | Suspected ZIKV infection | Positive Sensitivity %[b] (95% CI) | 85 — | 27 31.8 (22.8-42.3) | 71 83.5 (74.1-90.1) | 78 91.8 (83.7-96.2) | 38[e] — | 3 7.9 (2.0-21.5) | 34 89.5 (75.3-96.4) | 34 89.5 (75.3-96.4) |

CI: confidence interval; NA: not available or not applicable; NS: non-structural protein; RT-PCR: reverse transcription-PCR; ZIKV: Zika virus.
[a]This group contains 10 sera from residents of the Netherlands who were born and raised in Suriname and/or had visited their country of origin occasionally.
[b]Referring to the total number of samples in the respective patient group during the indicated sampling period.
[c]Referring to the whole study population of ZIKV-infected patients, i.e. samples (one per patient) taken between day 1 and day 88 post symptom onset, representing the initial (day 1-5 post symptom onset), active (day 6-20) and late phase (>20 days) of infection.
[d]Samples (one per patient) taken between day 6 and day 88 post symptom onset, representing the active (day 6 to 20 post symptom onset) and late phase (>20 days post symptom onset) of infection.
[e]Group 3 is not represented in the sampling period ≥6 days post symptom onset, because the sampling date was available for only four out of a total of 26 samples in this group.

TABLE 4

Anti-ZIKV reactivity in potentially cross-reactive specimens (n = 252) and healthy controls (n = 1,015) as determined by ELISA for IgM and IgG, study evaluating a novel NS1-based ELISA, Germany 2016

| Cohort | Characteristics | | Prevalence % (CI 95%)[c] | | Specificity (CI 95%)[c] | |
|---|---|---|---|---|---|---|
| | | | IgM | IgG | IgM | IgG |
| DENVa | Dengue viris infection (high median anti-DENV IgM)[a] | 47 | 0 (0-9.0) | 0 (0-9.0) | 100 (91.0-100) | 100 (91.0-100) |
| DENVb | Dengue viris infection (high median anti-DENV IgG[b] | 46 | 0 (0-9.2) | 0 (0-9.2) | 100 (90.8-100) | 100 (90.8-100) |
| YFV | Yellow fever virus vaccination | 12 | 0 (0-28.2) | 0 (0-28.2) | 100 (71.8-100) | 100 (71.8-100) |
| WNV | West Nile virus infection | 34 | 2.9 (0-16.2) | 0 (0-12.1) | 97.1 (83.8-100) | 100 (87.9-100) |
| JEV | Japanese encephalitis virus infection | 25 | 0 (0-15.8) | 4.0 (0-21.1) | 100 (84.2-100) | 96.0 (78.9-100) |
| CHIKV | Chikungunya virus infection | 19 | 0 (0-19.8) | 0 (0-19.8) | 100 (80.2-100) | 100 (80.2-100) |
| PLAS | *Plasmodium* spp. Infection | 69 | 1.4 (0-8.5) | 0 (0-6.3) | 98.6 (91.5-100) | 100 (93.7-100) |
| Total | Potentially cross-reactive samples | 252 | 0.8 (0-3.0) | 0.4 (0-24) | 99.2 (97.0-100) | 99.6 (97.6-100) |
| PREG | German pregnant women | 100 | 0 (0-4.4) | 0 (0-14) | 100 (95.6-100) | 100 (95.6-100) |
| ZIM | Zimbabwean blood donors | 128 | 0 (0-3.5) | 0 (0-3.5) | 100 (96.5-100) | 100 (96.5-400) |
| ARG | Argentinian blood donors | 99 | 1.0 (0-6.1) | 0 (0-4.5) | 99.0 (94.0-100) | 100 (95.5-100) |

TABLE 4-continued

Anti-ZIKV reactivity in potentially cross-reactive specimens (n = 252) and healthy controls (n = 1,015) as determined by ELISA for IgM and IgG, study evaluating a novel NS1-based ELISA, Germany 2016

| Cohort | Characteristics | | Prevalence % (CI 95%)[c] | | Specificity (CI 95%)[c] | |
|---|---|---|---|---|---|---|
| | | | IgM | IgG | IgM | IgG |
| US | US-American blood donors | 100 | 0 (0-4.4) | 1.0 (0-6.0) | 100 (95.6-100) | 99.0 (94.0-100) |
| GER | German blood donors | 500 | 0.2 (0-1.2) | 0.2 (0-1.2) | 99.8 (98.8-100) | 99.8 (98.8-400) |
| CHIL | German children | 88 | 0 (0-5.0) | 0 (0-5.0) | 100 (95.0-100) | 100 (95.0-100) |
| Total | Healthy control samples | 1,015 | 0.2 (0-0.8) | 0.2 (0-0.8) | 99.8 (99.2-100) | 99.8 (99.2-100) |

ARG: Argentina; CHIKV: chikungunya virus; CHIL: children; DENV: dengue virus; GER: Germany; JEV: Japanese encephalitis virus; PLAS: *Plasmodium*; PREG: pregnant women; US: United States; WNV: West Nile virus; YFV: yellow fever virus; ZIKV: Zika virus; ZIM: Zimbabwe.
[a]Median anti-DENV IgM ratio 3.9 (79% of samples with anti-DENV IgM ratio ≥3.0), as indicated in the inset of FIG. 9A.
[b]Median anti-DENV IgG ratio 3.9 (80% of samples with anti-DENV IgG ratio ≥3.0), as indicated in the inset of FIG. 9B.
[c]Referring to the total number of samples in the individual cohorts.

Comparing ZIKV-infected travellers returning from endemic areas (groups 1 and 3) with infected residents in these areas (groups 2 and 4), a tendency of distinct ZIKV antibody kinetics could be observed: in most returning travellers, high IgM ratio values (median 5.6; interquartile range (IQR): 4.6-6.9,) and moderate IgG ratios (median 2.2; IQR 0.9-2.8,) were detectable in the active phase of infection (cut-off ratio: 1.1). By contrast, the majority of endemic-area residents had infections with very high IgG ratios (median 4.8; IQR 3.3-5.9) during the active phase, while IgM ratios were variable, but predominantly negative or low (median 0.5; IQR 0.2-1.3) (FIGS. 9A and 9B).

Time course analysis of a German patient who showed clinical symptoms after returning from a stay in Colombia revealed very high anti-ZIKV IgM ratios on first testing (day 10 after symptom onset), while IgG ratios increased to moderate levels during the acute phase of infection and thereafter (FIG. 9C). On the other hand, follow-up samples taken from a Colombian resident with RT-PCR-confirmed ZIKV infection indicated a significant rise in the ZIKV-specific IgG response between days 3 and 15 after symptom onset, followed by a slow decrease, while anti-ZIKV IgM was negative 3 days after symptom onset and remained below detection threshold for 14 weeks (FIG. 9D).

Cross-Reactivity of the Enzyme-Linked Immunosorbent Assay

Cross-reactivity was analysed first in sera from 93 DENV-infected patients whose diagnosis had been secured by positive DENV-NS1 detection. This cohort was divided into one group (DENVa) with high anti-DENV IgM (median ratio 3.9) and another group (DENVb) with high anti-DENV IgG (median ratio 3.9), ensuring the presence of high levels of potentially cross-reactive antibodies. In both groups, anti-ZIKV reactivity was below the threshold, indicating absence of cross-reactivity in these specimens. Further testing, on a supplementary basis, included 159 sera from patients positive for IgM and/or IgG against YFV, WNV, JEV, CHIKV or PLAS. Anti-ZIKV IgM was positive in 1/34 (2.9%) patients infected with WNV and 1/69 (1.4%) patients infected with PLAS. Anti-ZIKV IgG was found in 1/25 (4.0%) patients infected with JEV. For the total of 252 potentially cross-reactive samples, the overall positivity rate amounted to 2/252 (0.8%) for IgM and 1/252 (0.4%) for IgG (Table 4).

Specificity of the Enzyme-Linked Immunosorbent Assay

Assay specificity was assessed by testing 1,015 sera from healthy controls. Only 1/99 (1.0%) Argentinian and 1/500 (0.2%) German blood donors were found anti-ZIKV IgM positive, while all 128 Zimbabwean and 100 US American blood donors as well as 100 German pregnant women and 88 children in Germany were negative. Anti-ZIKV IgG was present in 1/100 (1.0%) US American and 1/500 (0.2%) German blood donors, but absent in the cohorts of Zimbabwean and Argentinian blood donors, pregnant women and children. Thus, overall specificity amounted to 99.8% for either Ig class (Table 4, FIGS. 10A and 10B).

Discussion

The serological diagnosis of ZIKV infections has been challenging due to cross-reactions with other flaviviruses, secondary infections and previous vaccinations, which complicate interpretation, sometimes leading to unreliable or false-positive results. Here, we evaluated a newly-developed ELISA with recombinant ZIKV-NS1 protein as solid-phase antigen. Huzly et al. (2016 Apr. 21; 21(16). doi: 10.2807/1560-7917) recently provided evidence that this assay is highly specific, as demonstrated on a limited number of European patients with DENV, YFV, tick-borne encephalitis virus (TBEV) or hepatitis C virus infection. In the present study, testing on specimens collected ≥6 days after onset of symptoms (i.e. after the viraemic phase) revealed a combined sensitivity (IgM/IgG) of 100% for RT-PCR-confirmed cases of ZIKV infection at 99.8% specificity. Among suspected ZIKV cases, the combined sensitivity amounted to 89.5%. Notably, we included only one serum sample for each of the studied patients in our analysis, except for the time course analysis. For the serological diagnosis of patients, however, the evaluation of follow-up samples is important and recommended to demonstrate seroconversion or a 4-fold increase in antibody titre. In four of 27 RT-PCR-confirmed ZIKV cases, samples were negative for both IgM and IgG against ZIKV-NS1, presumably because all of them were taken only s 4 days after symptom onset, i.e. when antibodies had not yet reached detectable levels. Among 85 suspected ZIKV patients, too early sampling may account for two cases with negative IgM and IgG, while the remaining five double-negative cases could be due to the absence of ZIKV infection (deficits in pre-characterisation) or to false-negative results.

Cross-reactivity with high-level DENV antibodies was not detectable and, according to preliminary analysis with a limited amount of samples, there was no indication for DENV serotype-dependent differences in cross-reactivity (data not shown). To better judge assay performance in endemic areas, samples from endemic residents who experienced multiple DENV (and other flavivirus) infections should be included in further assessments, as these samples have a potential for increased cross-reactivity. Analysis of all potentially cross-reactive specimens resulted in positive rates of 0.8% (IgM) and 0.4% (IgG) caused by one case each with WNV and PLAS with low-level anti-ZIKV IgM and one JEV case with low-level anti-ZIKV IgG. In these cases, however, double infections cannot be excluded, so it remains unclear if ELISA positivity resulted from the presence of ZIKV antibodies due to co-infection with ZIKV (true-positive) or from cross-reactivity (false-positive). In case of PLAS infection, PLAS-induced polyclonal B-cell activation may cause the production of potentially cross-reactive antibodies. Among patients with current PLAS infection, up to 30% false-positive or borderline reactions were reported using the presented NS1-based ELISA, which is in contrast to only 1.4% in the present study and probably explained by the fact that our cohort was comprised mainly of individuals with past PLAS infection status. Possible interferences should thus be considered when applying the assay.

In sera from travellers returning from ZIKV-endemic areas, we observed a tendency of ZIKV-specific IgM to appear at high ratios during the active phase of infection, paralleled by a moderate rise in IgG. In contrast, most residents in endemic areas had high anti-ZIKV IgG and low/negative IgM ratio values, irrespective of whether their samples were taken during the initial, active or late phase of infection. IgM responses in travellers returning from ZIKV-endemic areas tended to be higher compared with residents in such areas, whereas the IgG-positivity rate was higher in the latter subgroup. Such differences in ZIKV antibody kinetics were also illustrated by time course analysis of antibody levels in two representative patients, possibly reflecting that travellers returning from ZIKV-endemic countries predominantly had a primary flavivirus/ZIKV infection, while most residents probably contracted ZIKV as a secondary flavivirus infection. Similar kinetics have been described for primary and secondary infections in the Micronesian ZIKV epidemic and for DENV-infected patients, suggesting that the detection of both specific IgM and IgG is diagnostically important and relevant for differentiating primary from secondary infections. Regarding our comparison of patients residing in endemic countries vs travellers, however, systematic differences in the background of these populations (e.g. genetic, ethnic) cannot be excluded.

Another limitation of our study is that it does not comprise side-by-side testing with additional assays, such as the Zika MAC-ELISA (Centers for Disease Control and Prevention (CDC), Atlanta, Georgia, US) or PRNT, to provide comparative data on these current tests. In addition, the non-deliberate absence of a uniform serological reference standard for the pre-characterisation of all ZIKV samples resulted in a high number of suspected cases of ZIKV infection.

Although ZIKV usually causes rather mild infections, there has been convincing evidence of a causal link to neuronal impairment, such as newborn microcephaly and GBS [37]. Furthermore, there have been studies showing that DENV NS1 antibodies have the potential of inducing autoantibodies in secondary infections, probably mediated by cross-reactive binding of antigens on platelets and endothelial cells, followed by cellular damage and inflammatory activation. Basic research is needed to fully elucidate the causal relations between neuronal disorders and ZIKV infection. Epidemiologic assessment of pregnant women and their babies, and of travellers returning from endemic areas, the surveillance of donated blood and the investigation of ZIKV prevalence in endemic and non-endemic areas may provide crucial information. These studies need reliable, fast, and easy-to-handle diagnostic tests that have low cross-reactivity and allow a definite diagnosis.

In conclusion, our study revealed that the NS1-based anti-ZIKV ELISA is a sensitive and highly specific tool for the serodiagnosis of ZIKV infections, eliminating cross-reactions with antibodies to DENV and other flaviviruses. The assay format is suitable for use in routine laboratories worldwide enabling high-throughput testing in epidemic settings. Serological identification of ZIKV infections is maximised by parallel testing for IgM and IgG. Further studies will be necessary to determine the accuracy of this and other current assays in a larger set of well-defined samples, and to clarify how ZIKV infection triggers GBS, newborn microcephaly and other neurological manifestations.

Example 8: Anti-Zika Virus IgA May Indicate an Acute Infection in Anti-Zika Virus IgM-Negative Patients This example shows that IgA to SEQ ID NO: 1 and related reagents and methods may be used for distinguishing an acute infection from a past and thus a primary from a secondary infection.

Methods

Serum samples were taken at several time points from two Columbians with a background of past flavivirus infections and from two German travellers, all presenting with confirmed ZIKV infections. Titers of anti-ZIKV IgM and IgG were measured using a commercial NS1-based Anti-Zika virus ELISA (Euroimmun AG, Germany). An indirect immunofluorescence test (Arbovirus Fever Mosaic 2, IgM, cut-off ≥1:10, Euroimmun AG, Germany) based on cells infected with ZIKV was used additionally for IgM measurement. For determination of anti-ZIKV IgA, a corresponding ELISA was adapted, applying an anti-human IgA conjugated with peroxidase. In all assays, the cut-off was set to a ratio of 1.1.

Results

In the German travellers, anti-ZIKV IgM was detected at day 9 and day 16, respectively, irrespective of the method. Active infections were subsequently confirmed by anti-ZIKV IgG seroconversion. IgA measurements were above 1.1 in all samples except for one, showing an initial increase and a subsequent decrease (Table 5)

| Patient | Country of origin | Country of infection | Days after symptoms | Anti-ZIKV IgA ratio; pos: >1.1 | Anti-ZIKV IgM ratio; pos: >1.1 | Anti-ZIKV IgG ratio; pos: >1.1 |
|---|---|---|---|---|---|---|
| 1 | Colombia | Colombia | −16 | 0.1 | 0.0 | 0.6 |
|   |          |          | 6   | 0.6 | 0.0 | 2.0 |
|   |          |          | 24  | 3.4 | 0.0 | 4.9 |
|   |          |          | 66  | 0.6 | 0.0 | 3.3 |
| 2 | Colombia | Colombia | 3   | 0.2 | 0.1 | 2.0 |
|   |          |          | 15  | 2.9 | 0.5 | 5.9 |
|   |          |          | 38  | 0.7 | 0.2 | 5.2 |

| Patient | Country of origin | Country of infection | Days after symptoms | Anti-ZIKV IgA ratio; pos: >1.1 | Anti-ZIKV IgM ratio; pos: >1.1 | Anti-ZIKV IgG ratio; pos: >1.1 |
|---|---|---|---|---|---|---|
| | | | 52 | 0.6 | 0.1 | 5.0 |
| | | | 66 | 0.5 | 0.1 | 4.9 |
| | | | 76 | 0.6 | 0.1 | 5.1 |
| | | | 95 | 0.5 | 0.1 | 4.7 |
| 3 | Germany | Martinique | 11 | 4.1 | 1.0 | 0.1 |
| | | | 16 | 9.0 | 2.7 | 1.4 |
| | | | 36 | 1.5 | 1.2 | 2.5 |
| 4 | Germany | Nicaragua | 4 | 0.3 | 0.2 | 0.2 |
| | | | 9 | 7.6 | 2.4 | 1.0 |
| | | | 30 | 2.4 | 0.9 | 3.0 |

In the sequential samples of the two Colombian patients (results shown in FIGS. 11A and 11B), measurements of IgM antibodies against ZIKV-NS1 antigen were persistently below the cut-off. In accordance, testing for IgM against full Zika virus was negative in all but one, weak positive sample (1:10). Anti-ZIKV IgG was positive already within the first week in both patients. IgA, however, showed a titer increase, peaking above the cut-off in week three and four before dropping below the threshold again.

Conclusion

When specific IgM is not detectable neither with NS1— nor full virus-based assays as observed in the Colombian patients, measurement of anti-ZIKV IgA may allow discrimination of acute from past infections.

Example 9: Absence of Specific IgM in Week Six Post Symptom Onset in a Patient with Confirmed Zika Virus Infection This example shows that detecting the presence or absence of both IgG and IgM to SEQ ID NO: 1 and related reagents and methods may be used for increasing the diagnostic reliability of an assay for diagnosing a Zika virus infection compared to assays based on the detection of Ig from one class only.

Introduction

Subsequently to the severe outbreak of Zika virus (ZIKV) infections in the Americas, CDC recommends nucleic acid testing in samples collected within two weeks after symptom onset. Serum samples collected after day 14 and up to day 84 should be tested for anti-ZIKV IgM antibodies assuming that these are present any time from near day four post symptom onset to up to twelve weeks.

However, absence of specific IgM has been frequently reported in patients with secondary Dengue virus (DENV) infections, since DENV and ZIKV are related flaviviruses immunological response may be comparable in ZIKV infections.

Methods

A Colombian woman of 42 years with ZIKV infection as confirmed by RT_PCR five days after appearance of the first symptoms was additionally tested for specific IgM and IgG antibodies. Serum samples taken at day five and day 41 post symptom onset were analysed using ZIKV IgM Capture ELISA, based on the full virus antigen (cut-off ratio 1.8; InBios, USA) and NS1-based Anti-Zika virus ELISA IgM as well as IgG (cut-off ratio 1.1; Euroimmun AG, Germany) according to instructions of the manufacturer.

Results

Results are shown in FIG. 12 and Table 6. The two serum samples revealed negative results in both IgM assays. Ratios in the IgM Capture ELISA ranged from 0.81 (day 5) to 0.12 (day 41), and measurements with the Anti-Zika virus ELISA IgM revealed ratios of 0.1 (day 5) and 0.4 (day 41). In contrast, testing for IgG yielded positive results at day 5 (ratio 1.9) as well as day 41 (ratio 5.6).

Conclusion

Both available serum samples of this patient dated from the suggested anti-ZIKV IgM-positive time frame (12 weeks) but were tested IgM-negative independently of the antigenic substrate used—full virus or NS1.

Instead, the two samples revealed an increasing IgG titer suggesting that parallel testing for anti-ZIKV IgM and IgG in two consecutive serum samples should be performed to detect either seroconversion or a significant IgG titer increase in order to avoid missing patients tested anti-ZIKV IgM-negative.

TABLE 6

| Days | Ratio | | |
|---|---|---|---|
| after onset of symptoms | IgM Capture ELISA Cut-off: 1.8 | NS1-based ELISA IgM Cut-off: 1.1 | NS1-based ELISA IgG Cut-off: 1.1 |
| 5 | 0.81 | 0.1 | 1.9 |
| 41 | 0.12 | 0.4 | 5.6 |

The invention claimed is:

1. A kit for the detection of Zika virus infection in a sample of a subject, comprising:
    a diagnostically useful carrier on which a polypeptide comprising SEQ ID NO: 1 or a variant thereof having at least 95% sequence identity is immobilized; and
    a secondary antibody binding to IgA class antibodies, which is directly or indirectly labeled.

2. The kit according to claim 1, wherein the diagnostically useful carrier is selected from the group consisting of a bead, a test strip, a microtiter plate, a blot, a lateral flow test, a glass surface, a slide, a biochip, a line blot, a microarray, and a membrane.

3. The kit according to claim 1, wherein the label is a fluorescent, enzymatically active, radioactive, chemiluminescent, electro-chemiluminescent label, or a spin label.

4. The kit according to claim 1, further comprising:
    a recombinant antibody binding to SEQ ID NO. 1.

5. The kit according to claim 1, wherein the kit comprises a negative control.

6. A kit for the detection of Zika virus infection in a sample of a subject, comprising
    a diagnostically useful carrier on which a secondary antibody binding to IgA class antibodies is immobilized; and
    a polypeptide comprising SEQ ID NO: 1 or a variant thereof having at least 95% sequence identity, which is directly or indirectly labeled.

7. The kit according to claim 6, wherein the diagnostically useful carrier is selected from the group consisting of a bead, a test strip, a microtiter plate, a blot, a lateral flow test, a glass surface, a slide, a biochip, a line blot, a microarray, and a membrane.

8. The kit according to claim 6, wherein the label is a fluorescent, enzymatically active, radioactive, chemiluminescent, electro-chemiluminescent label, or a spin label.

9. The kit according to claim 6, further comprising:
a recombinant antibody binding to SEQ ID NO: 1.

10. The kit according to claim 6, wherein the kit comprises a negative control.

* * * * *